United States Patent
Klinger

(10) Patent No.: US 9,402,874 B2
(45) Date of Patent: *Aug. 2, 2016

(54) LOW FREQUENCY GLATIRAMER ACETATE THERAPY

(71) Applicant: Yeda Research & Development Co., Ltd., Rehovot (IL)

(72) Inventor: Ety Klinger, Tel Aviv (IL)

(73) Assignee: YEDA RESEARCH & DEVELOPMENT CO., LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/673,257

(22) Filed: Mar. 30, 2015

(65) Prior Publication Data

US 2015/0202247 A1     Jul. 23, 2015

Related U.S. Application Data

(63) Continuation of application No. 14/630,326, filed on Feb. 24, 2015, which is a continuation of application No. 13/770,677, filed on Feb. 19, 2013, now Pat. No. 8,969,302, which is a continuation of application No. 12/806,684, filed on Aug. 19, 2010, now Pat. No. 8,399,413.

(60) Provisional application No. 61/274,687, filed on Aug. 20, 2009, provisional application No. 61/337,612, filed on Feb. 11, 2010.

(51) Int. Cl.
*A61K 38/02*     (2006.01)
*A61K 38/07*     (2006.01)
*A61K 38/16*     (2006.01)
*A61K 9/00*      (2006.01)

(52) U.S. Cl.
CPC .............. *A61K 38/02* (2013.01); *A61K 9/0019* (2013.01); *A61K 38/07* (2013.01); *A61K 38/16* (2013.01)

(58) Field of Classification Search
None
See application file for complete search history.

(56) References Cited

U.S. PATENT DOCUMENTS

| | | | |
|---|---|---|---|
| 3,849,550 A | 11/1974 | Teitelbaum et al. | |
| 4,822,340 A | 4/1989 | Kamstra | |
| 5,800,808 A | 9/1998 | Konfino et al. | |
| 5,981,589 A | 11/1999 | Konfino et al. | |
| 6,048,898 A | 4/2000 | Konfino et al. | |
| 6,054,430 A | 4/2000 | Konfino et al. | |
| 6,214,791 B1 | 4/2001 | Arnon et al. | |
| 6,342,476 B1 | 1/2002 | Konfino et al. | |
| 6,362,161 B1 | 3/2002 | Konfino et al. | |
| 6,448,225 B2 | 9/2002 | O'Connor et al. | |
| 6,454,746 B1 | 9/2002 | Bydlon et al. | |
| 6,514,938 B1 | 2/2003 | Gad et al. | |
| 6,620,847 B2 | 9/2003 | Konfino et al. | |
| 6,800,285 B2 | 10/2004 | Rodriguez et al. | |
| 6,800,287 B2 | 10/2004 | Gad et al. | |
| 6,844,314 B2 | 1/2005 | Eisenbach-Schwartz et al. | |
| 6,939,539 B2 | 9/2005 | Konfino et al. | |
| 7,022,663 B2 | 4/2006 | Gilbert et al. | |
| 7,033,582 B2 | 4/2006 | Yong et al. | |
| 7,074,580 B2 | 7/2006 | Gad et al. | |
| 7,163,802 B2 | 1/2007 | Gad et al. | |
| 7,199,098 B2 | 4/2007 | Konfino et al. | |
| 7,279,172 B2 | 10/2007 | Aharoni et al. | |
| 7,425,332 B2 | 9/2008 | Aharoni et al. | |
| 7,429,374 B2 | 9/2008 | Klinger | |
| 7,495,072 B2 | 2/2009 | Dolitzky | |
| 7,560,100 B2 | 7/2009 | Pinchasi et al. | |
| 7,615,359 B2 | 11/2009 | Gad et al. | |
| 7,625,861 B2 | 12/2009 | Konfino et al. | |
| 7,855,176 B1 | 12/2010 | Altman et al. | |
| 7,923,215 B2 | 4/2011 | Klinger | |
| 7,968,511 B2 | 6/2011 | Vollmer | |
| 8,008,258 B2 | 8/2011 | Aharoni et al. | |
| 8,232,250 B2 | 7/2012 | Klinger | |
| 8,367,605 B2 | 2/2013 | Konfino et al. | |
| 8,389,228 B2 | 3/2013 | Klinger | |
| 8,399,211 B2 | 3/2013 | Gad et al. | |
| 8,399,413 B2 | 3/2013 | Klinger | |
| 8,709,433 B2 | 4/2014 | Kasper | |
| 8,759,302 B2 | 6/2014 | Dhib-Jalbut | |

(Continued)

FOREIGN PATENT DOCUMENTS

WO     WO 95/31990     11/1995
WO     WO 98/30227     7/1998

(Continued)

OTHER PUBLICATIONS

U.S. Appl. No. 14/630,326, filed Feb. 24, 2015 (Klinger).
U.S. Appl. No. 14/520,280, filed Oct. 21, 2014 (Tchelet et al.).
U.S. Appl. No. 11/228,850, filed Sep. 14, 2005 (Schwartz et al.). The specification and claims as originally filed.
U.S. Appl. No. 11/654,374, filed Jan. 16, 2007 (Schwartz et al.). The specification and claims as originally filed.
U.S. Appl. No. 09/359,099, filed Jul. 22, 1999 (Strominger et al.). The specification and claims as originally filed.
Reissue Application in connection with U.S. Appl. No. 13/964,856, filed Aug. 12, 2013 (Konfino et al.).
Request for Ex Parte Re-examination by Third Party in connection with U.S. Control No. 90/013,249, filed May 21, 2014 (Konfino et al.).

(Continued)

*Primary Examiner* — Johann R Richter
*Assistant Examiner* — Katherine Peebles
(74) *Attorney, Agent, or Firm* — John P. White; Gary J. Gershik; Cooper & Dunham LLP

(57) ABSTRACT

A method of alleviating a symptom of relapsing-remitting multiple sclerosis in a human patient suffering from relapsing-remitting multiple sclerosis or a patient who has experienced a first clinical episode and is determined to be at high risk of developing clinically definite multiple sclerosis comprising administering to the human patient three subcutaneous injections of a therapeutically effective dose of glatiramer acetate over a period of seven days with at least one day between every subcutaneous injection so as to thereby alleviate the symptom of the patient.

28 Claims, No Drawings

(56) References Cited

U.S. PATENT DOCUMENTS

| | | | |
|---|---|---|---|
| 8,815,511 | B2 | 8/2014 | Tchelet et al. |
| 8,920,373 | B2 | 12/2014 | Altman et al. |
| 8,969,302 | B2 | 3/2015 | Klinger |
| 2002/0037848 | A1 | 3/2002 | Eisenbach-Schwartz et al. |
| 2002/0077278 | A1 | 6/2002 | Yong et al. |
| 2004/0106554 | A1 | 6/2004 | Konfino et al. |
| 2005/0014694 | A1 | 1/2005 | Yong |
| 2005/0019322 | A1 | 1/2005 | Rodriguez et al. |
| 2005/0170004 | A1 | 8/2005 | Rosenberger et al. |
| 2005/0171286 | A1 | 8/2005 | Konfino et al. |
| 2005/0277885 | A1 | 12/2005 | Scherer |
| 2006/0154862 | A1 | 7/2006 | Ray et al. |
| 2006/0172942 | A1 | 8/2006 | Dolitzky |
| 2006/0189527 | A1 | 8/2006 | Rasmussen et al. |
| 2006/0194725 | A1 | 8/2006 | Rasmussen et al. |
| 2006/0240463 | A1 | 10/2006 | Lancet |
| 2006/0264354 | A1 | 11/2006 | Aharoni et al. |
| 2007/0021324 | A1 | 1/2007 | Dolitzky |
| 2007/0037740 | A1 | 2/2007 | Pinchasi et al. |
| 2007/0048794 | A1 | 3/2007 | Gad et al. |
| 2007/0054857 | A1 | 3/2007 | Pinchasi et al. |
| 2007/0059798 | A1 | 3/2007 | Gad |
| 2007/0161566 | A1 | 7/2007 | Pinchasi |
| 2007/0173442 | A1 | 7/2007 | Vollmer |
| 2007/0244056 | A1 | 10/2007 | Hayardeny et al. |
| 2008/0118553 | A1 | 5/2008 | Frenkel et al. |
| 2008/0207526 | A1 | 8/2008 | Strominger |
| 2008/0261894 | A1 | 10/2008 | Kreitman et al. |
| 2009/0048181 | A1 | 2/2009 | Schipper et al. |
| 2009/0053253 | A1 | 2/2009 | Klinger |
| 2009/0149541 | A1 | 6/2009 | Stark et al. |
| 2010/0160894 | A1 | 6/2010 | Julian et al. |
| 2010/0167983 | A1 | 7/2010 | Kreitman et al. |
| 2010/0210817 | A1 | 8/2010 | Gad et al. |
| 2010/0285600 | A1 | 11/2010 | Lancet et al. |
| 2010/0298227 | A1 | 11/2010 | Aharoni et al. |
| 2010/0305023 | A1 | 12/2010 | Stark et al. |
| 2011/0046065 | A1 | 2/2011 | Klinger |
| 2011/0060279 | A1 | 3/2011 | Altman et al. |
| 2011/0066112 | A1 | 3/2011 | Altman et al. |
| 2012/0027718 | A1 | 2/2012 | Kreitman et al. |
| 2012/0309671 | A1 | 12/2012 | Klinger |
| 2014/0107208 | A1 | 4/2014 | Comabella et al. |
| 2014/0193827 | A1 | 7/2014 | Schwartz et al. |
| 2014/0271532 | A1 | 9/2014 | Kreitman et al. |
| 2014/0271630 | A1 | 9/2014 | Vollmer |
| 2014/0294899 | A1 | 10/2014 | Kasper et al. |
| 2014/0322158 | A1 | 10/2014 | Dhib-Jalbut |
| 2015/0045306 | A1 | 2/2015 | Tchelet et al. |

FOREIGN PATENT DOCUMENTS

| | | |
|---|---|---|
| WO | WO 00/05250 | 2/2000 |
| WO | WO 00/05249 | 3/2000 |
| WO | WO 00/20010 | 4/2000 |
| WO | WO 2000/018794 | 4/2000 |
| WO | WO 00/27417 | 5/2000 |
| WO | WO 01/60392 | 8/2001 |
| WO | WO 01/93828 | 12/2001 |
| WO | WO 01/97846 | 12/2001 |
| WO | WO 03/048735 | 6/2003 |
| WO | WO 2004/103297 | 2/2004 |
| WO | WO 2004/043995 | 5/2004 |
| WO | WO 2004/064717 | 8/2004 |
| WO | WO 2004/091573 | 10/2004 |
| WO | WO 2005/041933 | 5/2005 |
| WO | WO 2005/084377 | 9/2005 |
| WO | WO 2005/120542 | 12/2005 |
| WO | WO 2006/029036 | 3/2006 |
| WO | WO 2006/029393 | 3/2006 |
| WO | WO 2006/029411 | 3/2006 |
| WO | WO 2006/050122 | 5/2006 |
| WO | WO 2006/083608 | 8/2006 |
| WO | WO 2006/089164 | 8/2006 |
| WO | WO 2006/116602 | 11/2006 |
| WO | WO 2007/030573 | 3/2007 |
| WO | WO 2007/081975 | 7/2007 |
| WO | WO 2008/006026 | 1/2008 |
| WO | WO 2009/070298 | 6/2009 |
| WO | WO 2011/008274 | 1/2011 |
| WO | WO 2011/022063 | 2/2011 |
| WO | WO 2012/051106 | 4/2012 |
| WO | WO 2013/055683 | 4/2013 |
| WO | WO 2014/058976 | 4/2014 |
| WO | WO 2014/107533 | 7/2014 |
| WO | WO 2014/165280 | 10/2014 |

OTHER PUBLICATIONS

Oct. 10, 2012 Office Action, issued in connection With U.S. Appl. No. 12/761,367, filed Apr. 15, 2010.

Jul. 3, 2012 Response, filed in connection With U.S. Appl. No. 12/761,367, filed Apr. 15, 2010.

Jun. 4, 2012 Office Action, issued in connection With U.S. Appl. No. 12/761,367, filed Apr. 15, 2010.

Nov. 1, 2010 Notice of Allowance, issued in connection with U.S. Appl. No. 12/785,125, filed May 21, 2010.

Jun. 10, 2014 Office Action, issued in connection with U.S. Appl. No. 12/948,611, filed Nov. 17, 2010.

Oct. 6, 2014 Response, filed in connection with U.S. Appl. No. 12/948,611, filed Nov. 17, 2010.

Dec. 24, 2014 Notice of Allowance, issued in connection with U.S. Appl. No. 12/948,611, filed Nov. 17, 2010.

Dec. 16, 2013 Office Action, issued in connection with U.S. Appl. No. 13/384,021, filed May 225, 2012.

Mar. 14, 2014 Response, filed in connection with U.S. Appl. No. 13/384,021, filed May 225, 2012.

May 8, 2014 Notice of Allowance, issued in connection with U.S. Appl. No. 13/384,021, filed May 25, 2012.

Sep. 3, 2014 Decision to discontinue the opposition proceedings in connection with European Patent No. EP2275086.

Jul. 9, 2013 Office Action Issued in Connection With U.S. Appl. No. 13/770,677 filed Feb. 19, 2013 (Klinger).

Amendment in Response to Jul. 9, 2013 Office Action filed Dec. 9, 2013 in Connection With U.S. Appl. No. 13/770,677 filed Feb. 19, 2013 (Klinger).

Feb. 5, 2014 Office Action Issued in Connection With U.S. Appl. No. 13/770,677 filed Feb. 19, 2013 (Klinger).

Amendment in Response to Feb. 5, 2014 Office Action filed Aug. 5, 2014 in Connection With U.S. Appl. No. 13/770,677 filed Feb. 19, 2013 (Klinger).

Notice of Allowance issued Oct. 24, 2014 issued in Connection With U.S. Appl. No. 13/770,677 filed Feb. 19, 2013 (Klinger).

Notice of Allowance issued Dec. 24, 2014 issued in Connection With U.S. Appl. No. 13/770,677 filed Feb. 19, 2013 (Klinger).

Mar. 20, 2015 Examiner's Report Issued in Connection With Australian Application No. 2013203367 (Klinger).

Gibson (2004) "Selection of Injecting Volume", Pharmaceutical Preformulation and Formulation, p. 332.

Khan et al. (2009) "Glatiramer acetate 20mg subcutaneous twice-weekly versus daily injections: results of a pilot, prospective, randomised, and rater-blinded clinical and MRI 2-year study in relapsing-remitting multiple sclerosis" Immunomodulation-2; Friday, Sep. 11, 2009.

Dec. 1, 2014 Answer to Counterclaims, filed in connection with *Teva Pharmaceuticals USA, Inc., et al., v. Sandoz Inc. and Momenta Pharmaceuticals, Inc.* in the the United States District Court for District of Delaware (Case No. 1:14-cv-01171-GMS).

Mar. 20, 2015 Answer to Amneal's Counterclaims, filed in connection with *Teva Pharmaceuticals USA, Inc., et al., v. Sandoz Inc. and Amneal Pharmaceuticals LLC*, in the the United States District Court for District of Delaware (Case No. 1:14-cv-01171-GMS).

Dec. 1, 2014 Answer to Counterclaims, filed in connection with *Teva Pharmaceuticals USA, Inc., et al., v. Doctor Reddy's Laboratories Ltd. and Doctor Reddy's Laboratories, Inc.* in the United States District Court for the District of Delaware (Case No. 1:14-cv-01172-GMS).

(56) References Cited

OTHER PUBLICATIONS

Nov. 26, 2014 Answer, filed in connection with *Teva Pharmaceuticals USA, Inc., et al.*, v. *Mylan Pharmaceuticals Inc., Mylan Inc. and Natco Pharma Ltd.* in the United States District Court for the Northern District of West Virginia (Case. No. 1:14-cv-00167-IMK).

Jan. 23, 2015 Answer, filed in connection with *Teva Pharmaceuticals USA, Inc., et al.*, v. *Synthon Pharmaceuticals Inc., et al.* in the United States District Court for the District of Delaware (Case. No. 1:14-cv-01419-UNA).

Feb. 17, 2015 Answer to Counterclaims, filed in connection with *Teva Pharmaceuticals USA, Inc., et al.*, v. *Synthon Pharmaceuticals Inc., et al.* in the United States District Court for the District of Delaware (Case. No. 1:14-cv-01419-UNA).

Feb. 12, 2015 Plaintiff's Notice of Voluntary Dismissal, filed in connection with *Teva Pharmaceuticals USA, Inc., et al.*, v. *Synthon Pharmaceuticals Inc., et al.* in the United States District Court for the Middle District of North Carolina (Case. No. 1:14-cv-975).

Feb. 3, 2015 Complaint, filed in connection with *Teva Pharmaceuticals USA, Inc., et al.*, v. *Amneal Pharmaceuticals LLC* in the United States District Court for the District of Delaware (Case. No. 1:15-cv-00124-GMS).

Febraury 24, 2015 Answer, filed in connection with *Teva Pharmaceuticals USA, Inc., et al.*, v. *Amneal Pharmaceuticals LLC* in the United States District Court for the District of Delaware (Case. No. 1:15-cv-00124-GMS).

Sep. 10, 2014 Complaint, filed in connection with *Teva Pharmaceuticals USA, Inc.*, et al., v. *Sandoz Inc. and Momenta Pharmaceuticals, Inc.* in the the United States District Court for District of Delaware (Case No. 1:14-cv-01171-GMS).

Nov. 3, 2014 Answer, filed in connection with *Teva Pharmaceuticals USA, Inc., et al.*, v. *Sandoz Inc. and Momenta Pharmaceuticals, Inc.* in the United States District Court for the District of Delaware (Case No. 1:14-cv-01171-GMS).

Sep. 10, 2014 Complaint, filed in connection with *Teva Pharmaceuticals USA, Inc., et al.*, v. *Doctor Reddy's Laboratories Ltd. and Doctor Reddy's Laboratories, Inc.* in the United States District Court for the District of Delaware (Case No. 1:14-cv-01172-GMS).

Nov. 3, 2014 Answer, filed in connection with *Teva Pharmaceuticals USA, Inc., et al.*, v. *Doctor Reddy's Laboratories Ltd. and Doctor Reddy's Laboratories, Inc.* in the United States District Court for the District of Delaware (Case No. 1:14-cv-01172-GMS).

Sep. 11, 2014 Complaint, filed in connection with *Teva Pharmaceuticals USA, Inc., et al.* v. *Doctor Reddy's Laboratories Ltd., Doctor Reddy's Laboratories, Inc., Sandoz, Inc., and Momenta Pharmaceuticals* in the United States District Court for the District of New Jersey (Case No. 3:14-cv-05672-MAS-TJB).

Nov. 25, 2014 Plaintiff's Notice of Voluntary Dismissal, filed in connection with *Teva Pharmaceuticals USA, Inc., et al.* v. *Doctor Reddy's Laboratories Ltd., Doctor Reddy's Laboratories, Inc., Sandoz, Inc., and Momenta Pharmaceuticals* in the United States District Court for the District of New Jersey (Case No. 3:14-cv-05672-MAS-TJB).

Oct. 6, 2014 Complaint, filed in connection with *Teva Pharmaceuticals USA, Inc., et al.*, v. *Mylan Pharmaceuticals Inc., Mylan Inc. and Natco Pharma Ltd.* in the United States District Court for the District of Delaware (Case No. 1:14-cv-01278-GMS).

Oct. 7, 2014 Complaint, filed in connection with *Teva Pharmaceuticals USA, Inc., et al.*, v. *Mylan Pharmaceuticals Inc., Mylan Inc. and Natco Pharma Ltd.* in the United States District Court for the Northern District of West Virginia (Case. No. 1:14-cv-00167-IMK).

Nov. 18, 2014 Complaint, filed in connection with *Teva Pharmaceuticals USA, Inc., et al.*, v. *Synthon Pharmaceuticals Inc., et al.* in the United States District Court for the District of Delaware (Case. No. 1:14-cv-01419-UNA).

Nov. 19, 2014 Complaint, filed in connection with *Teva Pharmaceuticals USA, Inc., et al.*, v. *Synthon Pharmaceuticals Inc., et al.* in the United States District Court for the Middle District of North Carolina (Case. No. 1:14-cv-975).

Costello, K., et al., 'Recognizing Nonadherence in Patients with Multiple Sclerosis and Maintaining Treatment Adherence in the Long Term,' Medscape J Med., vol. 10(9):225 (2008).

Edgar, C.M., et al., 'Lipoatrophy in Patients with Multiple Sclerosis on Glatiramer Acetate,' Can. J. Neurol. Sci., vol. 31:58-63 (2004).

Ford, CC., et al. 'A Prospective open-label study of glatiramer acetate: over a decade of continuous use in multiple sclerosis patients,' Multiple Sclerosis, vol. 12:309-320 (2006).

Gagnon, L., "Every-Other-Day Dosing of Glatiramer Acetate Reduces Adverse Reactions With Comparable Efficacy to Daily Dosing: Presented at Wctrms," PeerView Press, (Sep. 21, 2008).

Ge, Y., et al. "Glatiramer Acetate (Copaxone) Treatment in Relapsing-Remitting Multiple Sclerosis", Neurology, vol. 54:813-817 (Feb. 2000).

Johnson, K.P., et al., 'Copolymer 1 reduces relapse rate and improves disability in relapsing-remitting multiple sclerosis: Results of a phase III multicenter, double-blind, placebo-controlled trial,' Neurology, vol. 45:1268-1276 (Jul. 1995).

Klauer, T., and Zettl, U.K., 'Compliance, adherence, and the treatment of multiple sclerosis,' J Neurol. vol. 255 (Suppl. 6):87-92 (2008).

Lisak, R.P. and Kira, J., 'Chapter 100, Multiple Sclerosis,' International Neurology, 366-374 (2009).

Manso, P.J., and Sokol, A.L., "Life cycle management of ageing pharmaceutical assets," Pharmaceutical Law Insight, vol. 3(7):16-19 (Jul./Aug. 2007).

A Study to Test the Effectiveness and Safety of a New Higher 40mg Dose of Copaxonee Compared to Copaxone® 20mg, the Currently Approved Dose [online]. ClinicalTrials.gov, 1993 [retrieved on Feb. 13, 2015]. Retrieved from the Internet: <URL:clinicaltrials.gov/show/NCT00202982>.

Copaxone®, Physicians' Desk Reference, 62nd ed. Montvale, NJ, Thomson Healthcare Inc., pp. 3231-3235 (2008).

Rebif® (interferon beta-la), Product Description, 103795.5062PI final 6.7.05 (2005).

This Is MS Multiple Sclerosis Community: Knowledge & Support [online]. ThisIsMS [retrieved on Sep. 3, 2014]. Retrieved from the Internet:<URL:www.thisims.com/forum/copaxonef4/topics5610.html>.

U.S. Appl. No. 12/231,292, filed on Aug. 29, 2008 (Aharoni et al.).
U.S. Appl. No. 13/083,112, filed Apr. 8, 2011 (Klinger).
U.S. Appl. No. 11/651,212, filed Jan. 9, 2007 (Pinchasi).The specification and claims as originally filed.
U.S. Appl. No. 12/861,655, filed Aug. 23, 2010 (Stark et al.).
U.S. Appl. No. 12/761,367, filed Apr. 15, 2010 (Altman et al.).
U.S. Appl. No. 12/785,125, filed May 21, 2010 (Altman et al.).
U.S. Appl. No. 13/384,021, filed Jul. 14, 2010 (Altman et al.).
U.S. Appl. No. 12/806,684, filed Aug. 19, 2010 (Klinger).
Office Action issued Jul. 20, 2009 in connection with U.S. Appl. No. 11/651,212, filed Jan. 9, 2007.
Amendment filed Jul. 1, 2009 in connection with U.S. Appl. No. 11/651,212, filed Jan. 9, 2007.
Office Action issued Apr. 2, 2009 in connection with U.S. Appl. No. 11/651,212, filed Jan. 9, 2007.
Amendment filed Dec. 22, 2008 in connection with U.S. Appl. No. 11/651,212, filed Jan. 9, 2007.
Office Action issued Jun. 20, 2008 in connection with U.S. Appl. No. 11/651,212, filed Jan. 9, 2007.
Written Opinion of the International Searching Authority issued Oct. 5, 2007 in connection with PCT International Application No. PCT/US07/00575, filed Jan. 9, 2007.
International Search Report issued Oct. 5, 2007 in connection with PCT International Application No. PCT/US07/00575, filed Jan. 9, 2007.
Response filed Sep. 23, 2010 in connection with U.S. Appl. No. 12/785,125, filed May 21, 2010.
Office Action issued Aug. 24, 2010 in connection with U.S. Appl. No. 12/785,125, filed May 21, 2010.
Aug. 19, 2013 Reply to Notice of Opposition, filed in connection with European Patent No. EP2275086.
Jul. 15, 2014 Notice of Withdrawal of Opposition, filed in connection with European Patent No. EP2275086.

(56) References Cited

OTHER PUBLICATIONS

Dec. 11, 2012 Notice of Opposition, filed in connection with European Patent No. EP2275086.
Communication issued Jul. 29, 2010 in connection with EPO Application No. 10160099.7.
Response filed Dec. 17, 2010 in connection with European Patent Application No. 10160099.7.
Communication Pursuant to Article 94(3) EPC issued Feb. 11, 2011 in connection with European Patent Application No. 10160099.7.
Response filed Jun. 13, 2011 in connection with European Patent Application No. 10160099.
Written Opinion of the International Searching Authority issued Jun. 9, 2011, in connection with PCT International Application No. PCT/US2010/001972, filed Jul. 14, 2010.
PCT International Search Report issued Jun. 9, 2011 in connection International Application No. PCT/US2010/001972, filed Jul. 14, 2010.
Oct. 10, 2012 Office Action Issued in Connection With U.S. Appl. No. 12/806,684, filed Aug. 19, 2010.
Response to the Oct. 10, 2012 Office Action filed Jan. 10, 2013 in connection with U.S. Appl. No. 12/806,684, filed Aug. 19, 2010.
Jan. 17, 2013 Notice of Allowance issued in connection with U.S. Appl. No. 12/806,684, filed Aug. 19, 2010.
Issue Notification issued Feb. 27, 2013 in connection with U.S. Appl. No. 12/806,684, filed Aug. 19, 2010.
U.S. Appl. No. 13/308,299, filed Nov. 30, 2011 (Klinger).
Feb. 14, 2012 Office Action Issued in Connection With U.S. Appl. No. 13/308,299, filed Nov. 30, 2011 (Klinger).
Amendment in Response to Feb. 14, 2012 Office Action filed May 14, 2012 in connection with U.S. Appl. No. 13/308,299, filed Nov. 30, 2011 (Klinger).
Notice of Allowance issued Jun. 15, 2012 issued in Connection With U.S. Appl. No. 13/308,299, filed Nov. 30, 2011.
Issue Notification issued Jul. 11, 2012 issued in Connection With U.S. Appl. No. 13/308,299, filed Nov. 30, 2011.
International Search Report issued Oct. 4, 2010 in connection with PCT International Application No. PCT/US/10/02283, filed Aug. 19, 2010 (Klinger).
Written Opinion of the International Searching Authority issued Oct. 4, 2010 in connection with PCT International Application No. PCT/US/10/02283, filed Aug. 19, 2010 (Klinger).
Feb. 29, 2012 Official Action Issued in Connection With Canadian Application No. 2,760,802, filed Aug. 19, 2012.
Response to the Feb. 29, 2012 outstanding Examiner's Report filed May 29, 2012 in connection with Canadian Application No. 2,760,802, filed Aug. 19, 2012 (Klinger).
Jul. 24, 2012 Official Action Issued in Connection With Canadian Application No. 2,760,802, filed Aug. 19, 2012 (Klinger).
Response to the Jul. 24, 2012 outstanding Examiner's Report filed Oct. 24, 2012 in connection with Canadian Application No. 2,760,802, filed Aug. 19, 2012 (Klinger).
Official Action issued Nov. 28, 2012 in connection with Eurasian patent application No. 201270292 including English translation thereof.
Supplementary European Search Report issued Jul. 13, 2012 in connection with European Patent Application No. 10810282.3 filed Oct. 11, 2011.
Communication Pursuant to Article 94(3) EPC issued Aug. 8, 2012 in connection with European Patent Application No. 10810282.3, filed Oct. 11, 2011.
Response to Aug. 8, 2012 Communication Pursuant to Article 94(3) EPC filed Sep. 13, 2012 in connection with European Patent Application No. 10810282.3, filed Oct. 11, 2011.
Examination Report issued Nov. 5, 2012 in connection with New Zealand patent application No. 598661.
Anderson, et al. "Injection pain decreases with new 0.5 mL formulation of glatiramer acetate" The Consortium of Multiple Sclerosis Centers 2010 Annual Meeting, Jun. 2-5, 2010, San Antoinio, Texas (Abstract only).

Anderson, et al. (1992) "Revised estimate of the prevalence of multiple sclerosis in the United States". Ann Neurol. 31:333-36.
Arnon and Aharoni (2007) "Neurogenesis and neuroprotection in the CAN -Fundamental elements in the effect of glatiramer acetate on treatment of autoimmune neurological disorders". Mol Neurobiol. 36:245-53.
Bjartmar C, et al. (2002) "Pathological mechanisms and disease progression of multiple sclerosis: therapeutic implications". Drugs of Today. 38:7-29.
Bornstein, et al., "A Placebo-controlled, Double-blind, Randomized Two-center, Pilot Trial of Cop 1 in Chronic Prgressive Multiple Sclerosis," Neurol., 1991, 41, 533-539.
Bornstein et al., "Rationale for Immunomodulating Therapies of Multiple Sclerosis: Clinical Trial Design in Multiple Sclerosis Therapy," Neurol., 1988, vol. 38 (Suppl.2), pp. 80-81 [R].
Bornstein "Clincal Experience: Hopeful Prospects in Multiple Sclerosis," Hospital Practice (Off. Ed.), 1992, vol. 27, No. 5, pp. L135-158, 141-142, 145-158.
Bornstein "Cop 1 may be Beneficial for Patients with Exacerbating-remitting Form of Multiple Sclerosis," Adv. Ther. (USA), 1987, 4, 206 (Abstract).
Bornstein et al., "Treatment of Multiple Sclerosis with Copolymer 1" in Treatment of Multiple Sclerosis: Trial Design, Results and Future Perspectives (Rudick R.A. & Goodkin D.E., eds., Springer Lerlag, London, 1992) 173-198.
Bornstein et al., "A Pilot Trial of Cop 1 in Exacerbating-remitting Multiple Sclerosis," New Eng. J. Med., 1987, 317(7), 408-414.
Bornstein et al., "Clinical Experience with COP-1 in Multiple Sclerosis," Neurol., 1988, 38(Suppl. 2) 66-69.
Bornstein et al., "Clinical Trials of a Synthetic Polypeptide (Copolymer 1) for the treatment of Mutliple Sclerosis" in Gonsett et al., Immunological and Clinical Aspects of Multiple Sclerosis (MTP Press, The Hague, 1984) 144-150.
Bornstein et al., "Clinical Trials of Copolymer 1 in Multiple Sclerosis," Ann. N.Y. Acad. Sci. (USA), 1984, 366-372.
Bornstein et al., "Multiple Sclerosis: Clinical Trials of a Synthetic Polypeptide, Copolymer 1," Neurol., 1985, 35, (Suppl. 1), 103 (Abstract).
Bornstein et al., "Multiple Sclerosis: Trial of a Synthetic Polypeptide," Ann. Neurol., 1982, 11, 317-319.
Bornstein et al., "Pilot Trial of COP-1 in Chronic Progressive Multiple Sclerosis: Preliminary Report," from The International Multiple Sclerosis Conference: An Update on Multiple Sclerosis, Roma (Italy), Sep. 15-17, 1988, in Elsevier Science Publisher, 1989, 225-232.
Bornstein et al., "Treatments of Multiple Sclerosis with a Synthetic Polypeptide: Preliminary Results," Ann. Neurol., 1980, 8, 117 (Abstract).
Bornstein et al., "Treatments of Multiple Sclerosis with a Synthetic Polypeptide: Preliminary Results," Trans. Am. Neurol. Assoc., 1980, 105, 348-350.
Bornstein et. al., "Clinical Trials of Cop 1 in Multiple Sclerosis," in Handbook of Multiple Sclerosis (S.D. Cook Marcel Rekker, ed., 1990) 469-480.
Brazeau GA, et al. (1998) "Current perspectives on pain upon injection of drugs". J Pharmaceutical Sci.(87)6:667-677.
Caon et al. (2009) "Randomized, prospective, rater-blinded, four year pilot study to compare the effect of daily versus every other day glatiramer acetate 20 mg subcutaneous injections in RRMS" Neurology vol. 72, No. 11, p. A317.
Chantelau, et al. (1991) "What make insulin injections painful?" BMJ. 303:26-27.
Comi G. "Treatment with glatiramer acetate delays conversion to clinically definite multiple sclerosis (CDMS) in patients with clinically isolated syndromes (CIS)". Program and abstracts of the American Academy of Neurology 60th Annual Meeting; Apr. 12-19, 2008; Chicago, Illinois. LBS.003.
Comi, et al. (2001) "European/Canadian multicenter, double-blind, randomized, placebo-controlled study of the effects of glatiramer acetate on magnetic resonance imagine-measured disease activity and burden in patients with relapsing multiple sclerosis". Ann Neurol. 49:290-7.

(56) References Cited

OTHER PUBLICATIONS

Comi, et al. (2008) "Results from a phase III, one-year, randomized, double-blind, parallel-group, dose-comparison study with glatiramer acetate in relapsing-remitting multiple sclerosis". Mult Scler. 14(suppl 1):S299.
Dhib-Jalbut S. (2002) "Mechanisms of action of interferons and glatiramer acetate in multiple sclerosis". Neurology. 58(Suppl 4):S3-S9.
Dhib-Jalbut S. (2003) "Glatiramer acetate (Copaxone) therapy for multiple sclerosis". Pharmacol Ther. 98:245-55.
Flechter S. et al. (2002) "Comparison of glatiramer acetate (Copaxone®) and interferon beta-1b (Betaferon®) in multiple sclerosis patients: An open-label 2-year follow up" Journal of the Neurological Sciences vol. 197, No. 1-2 pp. 51-55.
Frenken LA, et al. (1994) "Analysis of the efficacy of measures to reduce pain after subcutaneous administration of epoetin alfa". Nephrol Dial Transplant. 9: 1295-1298.
Guideline of Clinical investigation of medicinal products for the treatment of multiple sclerosis EMEA, London 16 Nov. 2006 CPMP/EWP/561/98 Rev.1, pp. 1-12.
Johnson, et al. (1998) "Extended use of glatiramer acetate (Copaxone) is well tolerated and maintains its clinical effect on multiple sclerosis relapse rate and degree of disability". Neurology. 50:701-8.
Jorgensen J.T. et al. (1996) "Pain assessment of subcutaneous injections" Annals of Pharmacotherapy, Harvey Whitney Books Company, vol. 30. No. 7-8, pp. 729-732.
Kansara, et al. (2009) "Subcutaneous Delivery". Drug Deliv Technol. Jun. 2009; 9(6):38-42.
Khan et al. (2008) "Randomized, prospective, rater-blinded, four-year, pilot study to compare the effect of daily versus every-other-day injections in relapsing -remitting multiple" Mult. Scler. 14 Suppl. 1 S296.
Khan O. et al., (2008) "Randomized, prospective, rater-blinded, four-year, pilot study to compare the effect of daily versus every-other-day glatiramer acetate 20 mg subcutaneous injections in relapsing-remitting multiple sclerosis", Multiple Sclerosis; 14: 5295-5298.
Medical News Today. Jul. 8, 2008. Web. Sep. 9, 2010. http://www.medicalnewstoday.com/articles/114183.php.
Miller D, et al. (2005) "Clinically isolated syndromes suggestive of multiple sclerosis, part I: natural history, pathogenesis, diagnosis, and prognosis". Lancet Neurol. 4(5):281-288.
Miller D, et al. (2005) "Clinically isolated syndromes suggestive of multiple sclerosis, part II: non-conventional MRI, recovery process, and management". Lancet Neurol. 4(6):341-348.
Neuhaus O, et al. (2003) "Immunomodulation in multiple sclerosis: from immunosuppression to neuroprotection". Trends Pharmacol Sci. 24:131-138.
Noseworthy, et al. (2000) "Multiple sclerosis". N Engl J Med. 343:938-52.
Polin. (2003) The Ins and Outs of Prefilled Syringes. Pharmaceutical & Medical Packaging News/Medical Device Link.
Polman, et al. (2005) "Diagnostic Criteria for Multiple Sclerosis: 2005 Revisions to the "McDonald" Criteria". Ann Neurol. 58:840-846.
Product Monograph, Copaxone, Revised Apr. 2, 2010: 1-35.
Ruggiere, et al. (2007) "Glatiramer acetate in multiple sclerosis: A review". CNS Drug Reviews. 13(2):178-91.
Schrempf W, et al. (2007) "Glatiramer acetate: Mechanisms of action in multiple sclerosis". Autoimmunity Reviews 2007. 6:469-475.
Shire, et al. (2004) "Challenges in the Development of High Protein Concentration Formulations". J Pharm Sci. 93(6):1390-1402.
Simpson Dene et al. (2002) "Glatiramer acetate: A review of its use in relapsing-remitting multiple sclerosis" CNS Drugs vol. 16, No. 12 pp. 825-850.
The National MS Society (USA) [cited Feb. 5, 2010]. Available from: http://www.nationalmssociety.org/about-multiple-sclerosis/what-we-know-about-ms/treatments/index.aspx.
Thrower BW. (2007) "Clinically isolated syndromes. Predicting and delaying multiple sclerosis". Neurology. 68 (Suppl 4):S12-S15.
Tselis, et al. (2007) "Glatiramer acetate in the treatment of multiple sclerosis". Neuropsychiatric Dis Treat. 3(2):259-67.
Van Metre TE, et al. (1996) "Pain and dermal reaction caused by injected glycerin in immunotherapy solutions". J Allergy Clin Immunol. 97:1033-9.
Weber, et al. (2007) "Mechanism of action of glatiramer acetate in treatment of multiple sclerosis". Neurotherapeutics. 4(4):647-53.
Wolinsky, et al. (2007) "Glatiramer acetate in primary progressive multiple sclerosis: Results of a multinational, multicenter, double-blind, placebo-controlled trial". Ann Neurol. 61:14-24.
Wolinsky, JS (2006) "The use of glatiramer acetate in the treatment of multiple sclerosis". Adv Neurol. 273-92.
Ziemssen and Schrempf (2007) "Glatiramer acetate: Mechanisms of action in multiple sclerosis". International Rev of Neurobiol. 79:537-70.
Feb. 6, 2015 Petition for Inter Partes Review, filed in connection with *Mylan Pharmaceuticals Inc.* v. *Yeda Research & Development Co. Ltd.* for U.S. Pat. No. 8,232,250 in the United States Patent and Trademark Office Patent Trial and Appeal Board (Case No. IPR2015-00643).
Feb. 7, 2015 Petition for Inter Partes Review, filed in connection with *Mylan Pharmaceuticals Inc.* v. *Yeda Research & Development Co. Ltd.* for U.S. Pat. No. 8,399,413 in the United States Patent and Trademark Office Patent Trial and Appeal Board (Case No. IPR2015-00644).
Mar. 3, 2015 Petition for Inter Partes Review, filed in connection with *Mylan Pharmaceuticals Inc.* v. *Yeda Research & Development Co. Ltd.* for U.S. Pat. No. 8,969,302 in the United States Patent and Trademark Office Patent Trial and Appeal Board (Case No. IPR2015-00830).
Fletcher S, et al., "Copolymer 1 (Glatiramer Acetate) in Relapsing Forms of Multiple Sclerosis: Open Multicenter Study of Alternate-Date Ad1ninistrations" Clinical Neuropharmacology, 2002, 25: 11-15, submitted as Exhibit 1008 in Inter Partes Review Case Nos. IPR2015-00643, IPR2015-00644 and IPR2015-00830.
Miller, The importance of early diagnosis of multiple sclerosis, 10(3) (Suppl. S-b) J.Manag. Care Pharm., S4-11 (2004),submitted as Exhibit 1013 in Inter Partes Review Case Nos. IPR2015-00643, IPR2015-00644 and IPR2015-00830.
Arnon, The Development of Cop 1 (Copaxone®), An Innovative Drug for the Treatment of Multiple Sclerosis: Personal Reflections, 50 Immunology Letters 1-15 (1996), submitted as Exhibit 1020 in Inter Partes Review Case Nos. IPR2015-00643, IPR2015-00644 and IPR2015-00830.
Haines et al., Linkage of the MHC to Familial Multiple Sclerosis Suggests Genetic Heterogeneity. The Multiple Sclerosis Genetics Group, Hum.Mol. Genet. 7:1229-34 (Aug. 1998), submitted as Exhibit 1023 in Inter Partes Review Case Nos. IPR2015-00643, IPR2015-00644 and IPR2015-00830.
U.S. Pat. No. 6,342,476, issued Jan. 29, 2002 (Konfino, et al.), submitted as Exhibit 1024 in Inter Partes Review Case Nos. IPR2015-00643, IPR2015-00644 and IPR2015-00830.
Ge et al., Glatiramer Acetate (Copaxone) Treatment in Relapsing-Remitting MS: Quantitative MR Assessment, 54 Neurology, 813-17 (2000), submitted as Exhibit in Inter Partes Review Case Nos. IPR2015-00643, IPR2015-00644 and IPR2015-00830.
McDonald et al., Recommended Diagnostic Criteria for Multiple Sclerosis: Guidelines from the International Panel on the Diagnosis of Multiple Sclerosis, Ann. Neurol. 50:121-27 (2001), submitted as Exhibit 1027 in Inter Partes Review Case Nos. IPR2015-00643, IPR2015-00644 and IPR2015-00830.
Rich et al., Stepped-care approach to treating MS: A managed care treatment algorithm, J. Managed Care Pharm. 10:S26-S32 (Jun. 2004), submitted as Exhibit 1028 in Inter Partes Review Case Nos. IPR2015-00643, IPR2015-00644 and IPR2015-00830.
Ziemssen et al., Effects of GLatiramer Acetate on Fatigue and Days of Absence from Work in First-Time Treated Relapsing-Remitting Multiple Sclerosis, Hlth. &Qual. Life Outcomes 6:67 (2008), submitted as Exhibit 1031 in Inter Partes Review Case Nos. IPR2015-00643, IPR2015-00644 and IPR2015-00830.
Stuart, Clinical Management of Multiple Sclerosis: The Treatment Paradigm and Issues of Patient Management, J. Managed Care Phar-

(56) References Cited

OTHER PUBLICATIONS macy 10:S19-S25 (Jun. 2004), submitted as Exhibit 1032 in Inter Partes Review Case Nos. IPR2015-00643, IPR2015-00644 and IPR2015-00830.
Bakshi et al., Imaging of Multiple Sclerosis: Role in Neurotherapeutics, 2(2) Neurorx, 277-303 (2005), submitted as Exhibit 1033 in Inter Partes Review Case Nos. IPR2015-00643, IPR2015-00644 and IPR2015-00830.
Frohman, Multiple Sclerosis—The Plaque and its Pathogenesis, New England J.Med. 354:842-55 (2006), submitted as Exhibit 1039 in Inter Partes Review Case Nos. IPR2015-00643, IPR2015-00644 and IPR2015-00830.
Kragt et al., How Similar are Commonly Combined Criteria for EDSS Progression in Multiple Sclerosis?, 12(6) Multople Sclerosis 782-786 (2006), submitted as Exhibit 1040 in Inter Partes Review Case Nos. IPR2015-00643, IPR2015-00644 and IPR2015-00830.
Pelidou et al., Multiple Sclerosis Presented as Clinically Isolated Syndrome: The Need for Early Diagnosis and Treatment, Ther. Clin. Riskmanagement 4:627-30 (Jun. 2008), submitted as Exhibit 1044 in Inter Partes Review Case Nos. IPR2015-00643, IPR2015-00644 and IPR2015-00830.
Jacobs et al., Intramuscular interferon beta-1a therapy intitiated during a first demyelinating event in multiple sclerosis, New Engl. J.Med. 343:898-904 (2008), submitted as Exhibit 1045 in Inter Partes Review Case Nos. IPR2015-00643, IPR2015-00644 and IPR2015-00830.
Copaxone®, Food and Drug Administration Approved Labeling, 2001 (NDA 20-622/S-015/S-015) submitted as Exhibit 1047 in Inter Partes Review Case Nos. IPR2015-00643, IPR2015-00644 and IPR2015-00830.
Betaseron® Interferon beta-1b, Product Label, 2003 (10004938), submitted as Exhibit 1048 in Inter Partes Review Case Nos. IPR2015-00643, IPR2015-00644 and IPR2015-00830.
Rebif® (interferon beta-1a), Product Label, 2003, submitted as Exhibit 1049 in Inter Partes Review Case Nos. IPR2015-00643, IPR2015-00644 and IPR2015-00830.
Avonex® (interferon beta-1a) IM Injection, Product Label, 2006, submitted as Exhibit 1050 in Inter Partes Review Case Nos. IPR2015-00643, IPR2015-00644 and IPR2015-00830.
Tysabri®, Product Label, 2008, submitted as Exhibit 1051 in Inter Partes Review Case Nos. IPR2015-00643, IPR2015-00644 and IPR2015-00830.
Copaxone®, Food and Drug Administration Approved Labeling, Feb. 2009, submitted as Exhibit 1052 in Inter Partes Review Case Nos. IPR2015-00643, IPR2015-00644 and IPR2015-00830.
Rebif® (interferon beta-1a), Product Label, Jun. 2005, submitted as Exhibit 1059 in IPR2015-00643, Exhibit 1060 in Inter Partes Review Case No. IPR2015-00644 and Exhibit 1054 in Inter Partes Review Case No. IPR2015-00830.
Jacobs et al., (2000) "Intramuscular interferon beta-1a therapy initiated during a first demyelinating . . . " The New England Journal of Medicine, vol. 343, No. 13, pp. 898-904, submitted as Exhibit 1054 in Inter Partes Review Case Nos. IPR2015-00643 and IPR2015-00644.
Stedman's Medical Dictionary for Health Professionals and Nursing, sixth edition (2008), submitted as Exhibit 1055 in Inter Partes Review Case Nos. IPR2015-00643 and IPR2015-00644.
U.S. Pat. No. 3,849,550, issued Nov. 19, 1974 (Teitelbaum et al.), submitted as Exhibit 1055 in Inter Partes Review Case Nos. IPR2015-00643 and IPR2015-00644.
U.S. Patent Application Publication No. US 2009-0149541 A1, published Jun. 11, 2009 (Stark et al.), submitted as Exhibit 1056 in Inter Partes Review Case Nos. IPR2015-00643, IPR2015-00644 and IPR2015-00830.
DiPiro et al., Concepts in clinical pharmacokinetics, Fifth Edition, in Introduction to Pharmacokinetics and Pharmacodynamics, American Society of Health-System Pharmacists® (2010), submitted as Exhibit 1062 in Inter Partes Review Case Nos. IPR2015-00643, IPR2015-00644 and IPR2015-00830.

M. Tintore et al., Baseline MRI predicts future attacks and disability in clinically isolated syndromes, 67 Neurology 968-972, (2006), submitted as Exhibit 1058 in Inter Partes Review Case No. IPR2015-00644.
U.S. Patent Application Publication No. US 2013-0165387 A1, published Jun. 27, 2013 (Klinger), submitted as Exhibit 1060 in Inter Partes Review Case Nos. IPR2015-00830.
Orange Book: Approved Drug Products with Therapeutic Equivalence Evaluations [online], accessdata.fda.gov [retrieved on Jan. 29, 2015]. Retrieved from the Internet: <URL://www.accessdata.fda.gov/scripts/cder/ob/docs/patexclnew.cfm?Appl_No=020622& Product_No=003&table1=OB_Rx>, submitted as Exhibit 1060 in Inter Partes Review Case No. IPR2015-00643 and Exhibit 1061 in Inter Partes Review Case No. IPR2015-00644.
P.M. Rothwell et al. Doctors and Patients don't agree: cross sectional study of patients' and doctors ' perceptions and assessments of disability in multiple sclerosis 314 The BMJ 1580 (May 31, 1997), submitted as Exhibit 1061 in Inter Partes Review Case No. IPR2015-00643.
Amendment in Response to Feb. 14, 2012 Office Action and Summary of May 8, 2012 Examiner Interview Pursuant to 37 C.F.R. § 1.133(b), filed in connection with U.S. Appl. No. 13/308,299, submitted as Exhibit 1064 in Inter Partes Review Case No. IPR2015-00643.
Feb. 6, 2014 Opposition in connection with European Application Number 10810282.3; Patentee: *Yeda Research and Development Co., Ltd*. vs. Opponent: *Synthon BV*.
Feb. 7, 2014 Opposition in connection with European Application Number 10810282.3; Patentee: *Yeda Research and Development Co., Ltd*. vs. Opponent: *Actavis Group ehf*.
Feb. 6, 2012 Office Action Issued in Connection With U.S. Appl. No. 12/806,684, filed Aug. 19, 2010 (Klinger).
Jun. 27, 2014 Summons to attend oral proceedings pursuant to Rule 115 (1) EPC in connection with European Patent Application No. 10160099.7.
Nov. 25, 2011 Examiner's Report Issued in Connection With Australian Application No. 2010284666, filed Aug. 19, 2012 (Klinger).
Response to the Nov. 25, 2011 Examiner's Report filed Oct. 15, 2012 in Connection With Australian Application No. 2010284666, filed Aug. 19, 2012 (Klinger).
Jul. 10, 2013 Official Action Issued in Connection With Canadian Application No. 2,760,802, filed Aug. 19, 2012 (Klinger).
Response to the Jul. 10, 2013 outstanding Examiner's Report filed Oct. 10, 2013 in connection with Canadian Application No. 2,760,802, filed Aug. 19, 2012 (Klinger).
Jan. 8, 2014 Official Action Issued in Connection With Canadian Application No. 2,760,802, filed Aug. 19, 2012.
Response to the Jan. 8, 2014 outstanding Examiner's Report filed Apr. 8, 2014 in connection with Canadian Application No. 2,760,802, filed Aug. 19, 2012 (Klinger).
Apr. 1, 2013 Official Action Issued in Connection With Chinese Application No. 201080036966.0, filed Feb. 20, 2012 (Klinger) and English Translation thereof.
Response to the Apr. 1, 2013 outstanding Official Action filed Jun. 28, 2013 in Connection With Chinese Application No. 201080036966.0, Feb. 20, 2012 (Klinger).
Aug. 9, 2013 Official Action Issued in Connection With Chinese Application No. 201080036966.0, filed Feb. 20, 2012 (Klinger) and English Translation thereof.
Response to the Aug. 9, 2013 outstanding Official Action filed Oct. 24, 2013 in Connection With Chinese Application No. 201080036966.0, Feb. 20, 2012 (Klinger).
Decision of Rejection Issued in Connection With Chinese Application No. 201080036966.0, issued Feb. 8, 2014 (Klinger) and English Translation thereof.
Response to the Nov. 28, 2012 outstanding Official Action in connection with Eurasian patent application No. 201270292 (Klinger).
Response to the Mar. 18, 2013 outstanding Official Action in connection with Eurasian patent application No. 201270292 (Klinger).
Jul. 1, 2009 Response to Final Office action in connection with U.S. Appl. No. 11/651,212.
Sep. 13, 2012 Response to Communication under Art 94 (3) EPC in connection with European Application No. 10810282.3.

(56) References Cited

OTHER PUBLICATIONS

Communication Pursuant to Rule 69 EPC issued Sep. 2, 2013 in connection with European Patent Application No. 13166080.5.
Extended European Search Report issued Jul. 30, 2013 in connection with European Patent Application No. 13166080.5.
Feb. 26, 2014 Response to Extended European Search Report issued Jul. 30, 2013 in connection with European Patent Application No. 13166080.5.
Jan. 7, 2014 Official Action Issued in Connection With Japanese Application No. 2012-525530, filed Feb. 20, 2012 including English translation thereof.
Sep. 17, 2013 Official Action Issued in Connection with Korean Application No. 10-2012-7007115.
Feb. 5, 2014 Decision of Rejection issued in Connection with Korean Application No. 10-2012-7007115.
Feb. 26, 2014 Office action Issued in Connection With Taiwanese Application No. 099128023, filed Aug. 20, 2010 including English translation thereof.
Preliminary Conclusion of Substantive Examination issued Nov. 8, 2012 in connection with Ukrainian patent application No. 2012 03259 including English translation thereof.
U.S. Pat. No. 7,928,131, issued Apr. 19, 2011 (Buzard).
Flechter S, et al. (2002) "Copolymer 1 (Glatiramer Acetate) in Relapsing Forms of Multiple Sclerosis: Open Multicenter Study of Alternate-Day Ad1ninistration". Clinical Neuropharmacology, 25: 11-15.
Khan O. et al., "A phase 3 trial to assess the efficacy and safety of glatiramer acetate injections 40mg administered 3 times a week compared to placebo" Oct. 13, 2012; European Committee for Treatment and Research in Multiple Sclerosis.
Cohen et al. (2007) "Randomized, double-blind, dose comparison study of glatiramer acetate in relapsing-remitting MS". Neurology, 68: 939-944.
Endo et al. (2004) "How to proceed with therapy of multiple sclerosis". Modern Physician, 24: 1896-1901 including English translation thereof.
Copaxone 20 mg/ml, Solution for Injection, Pre-Filled Syringe, Summary of Product Characteristics updated on Apr. 17, 2009.
Copaxone 20 mg/ml or Copaxone 40 mg/ml, NDA 020622/S-089 FDA Approved Labeling Text dated Jan. 28, 2014.
Notice of Opposition to a European patent together with the Statement of Grounds for Opposition filed Feb. 10, 2014 in connection with European Patent EP 2405749 B1; Patentee: *Yeda Research and Development Co., Ltd.* vs. Opponent *Generics [UK] Limited (trading as Mylan)*.
Mar. 18, 2013 Official Action issued in connection with Eurasian Patent Application No. 201270292, filed Mar. 19, 2012 (Klinger) together with an English Translation thereof.
Aug. 14, 2013 Official Action issued in connection with Eurasian Patent Application No. 201270292, filed Mar. 19, 2012 (Klinger) and redacted English language summary thereof.
Claims as filed on Sep. 19, 2013 in connection with Eurasian Patent Application No. 201270292, filed Mar. 19, 2012 (Klinger) and English Translation thereof.
Immunological Responses to Different Doses of Glatiramer Acetate in MS: Analyses from the Forte Trial, Yong W. V., et al., abstract for poster session dated Apr. 28, 2009, presented at the 61st Annual American Academy of Neurology meeting in Seattle, Washington U.S.A.
"Teva to Present Positive Data for Glatiramer Acetate 40 mg/1ml Given Three Times Weekly for Relapsing-Remitting MS" [online] Teva Pharmaceutical Industries Ltd. Oct. 10, 2012 [retrieved on Apr. 2, 2013]. Retrieved from the Internet: <URL: www.tevapharm.com/Media/News/Pages/2012/1743500.aspx?year=2012& page>.
Teva Provides Update on Forte Trial, published on Jul. 7, 2008 at Jerusalem, Israel by Teva Pharmaceutical Industries Ltd.
A Study to Test the Effectiveness and Safety of a New Higher 40mg Dose of Copaxone® Compared to Copaxone® 20mg, the Currently Approved Dose [online]. ClinicalTrials.gov [retrieved on Sep. 3, 2014]. Retrieved from the Internet: <URL:clinicaltrials.gov/show/NCT00202982>.
Declaration of Stephen J. Peroutka, M.D., Ph.D., filed on Feb. 6, 2015 as Exhibit 1003 in connection with *Mylan Pharmaceuticals Inc.* v. *Yeda Research & Development Co. Ltd.* for U.S. Pat. No. 8,232,250 in the United States Patent and Trademark Office Patent Trial and Appeal Board (Case No. IPR2015-00643).
Expert Declaration of an Green, M.D. In Support of Petition for Inter Partes Review of U.S. Pat. No. 8,232,250, filed on Feb. 6, 2015 as Exhibit 1004 in connection with *Mylan Pharmaceuticals Inc.* v. *Yeda Research & Development Co. Ltd.* for U.S. Pat. No. 8,232,250 in the United States Patent and Trademark Office Patent Trial and Appeal Board (Case No. IPR2015-00643).
Declaration of Stephen J. Peroutka, M.D., Ph.D., filed on Feb. 6, 2015 as Exhibit 1003 in connection with *Mylan Pharmaceuticals Inc.* v. *Yeda Research & Development Co. Ltd.* for U.S. Pat. No. 8,399,413 in the United States Patent and Trademark Office Patent Trial and Appeal Board (Case No. IPR2015-00644).
Expert Declaration of an Green, M.D. In Support of Petition for Inter Partes Review of U.S. Pat. No. 8,399,413, filed on Feb. 6, 2015 as Exhibit 1004 in connection with *Mylan Pharmaceuticals Inc.* v. *Yeda Research & Development Co. Ltd.* for U.S. Pat. No. 8,399,413 in the United States Patent and Trademark Office Patent Trial and Appeal Board (Case No. IPR2015-00644).
Declaration of Stephen J. Peroutka, M.D., Ph.D., filed on Mar. 3, 2015 as Exhibit 1003 in connection with *Mylan Pharmaceuticals Inc.* v. *Yeda Research & Development Co. Ltd.* for U.S. Pat. No. 8,969,302 in the United States Patent and Trademark Office Patent Trial and Appeal Board (Case No. IPR2015-00830).
Expert Declaration of Ari Green, M.D. in Support of Petition for Inter Partes Review of U.S. Pat. No. 8,969,302, filed on Mar. 3, 2015 as Exhibit 1004 in connection with *Mylan Pharmaceuticals Inc.* v. *Yeda Research & Development Co. Ltd.* for U.S. Pat. No. 8,969,302 in the United States Patent and Trademark Office Patent Trial and Appeal Board (Case No. IPR2015-00830).
Affidavit of Marlene S. Bobka dated Dec. 9, 2014 together with Exhibit A, submitted as Exhibit 1007 in Inter Partes Review Case Nos. IPR2015-00643, IPR2015-00644 and IPR2015-00830.
International Application Publication No. WO 2007/081975, published Jul. 19, 2007 (Pinchasi), submitted as Exhibit 1005 in Inter Partes Review Case Nos. IPR2015-00643, IPR2015-00644 and IPR2015-00830.
Cohen et al., "Randomized, double-blind, dose comparison study of glatiramer acetate in relapsing remitting MS". Neurology, 2007, 68: 939-944, submitted as Exhibit 1006 in Inter Partes Review Case Nos. IPR2015-00643, IPR2015-00644 and IPR2015-00830.
Zeev Meiner et al., "Copolymer 1 in relapsing-remitting multiple sclerosis: a multi-centre trial" in: Abramsky et al., *Frontiers in Multiple Sclerosis: Clinical Research and Therapy* (London, Martin Dunitz, 1997), pp. 213-221, submitted as Exhibit 1009 in Inter Partes Review Case Nos. IPR2015-00643, IPR2015-00644 and IPR2015-00830.
Khan et al., "Randomized, prospective, rater-blinded, four-year, pilot study to compare the effect of daily versus every-other-day injections in relapsing-remitting multiple sclerosis" Mult. Scler. 2008, 14 Suppl. 1 5296, submitted as Exhibit 1010 in Inter Partes Review Case Nos. IPR2015-00643, IPR2015-00644 and IPR2015-00830.
Caon et al., "Randomized, prospective, rater-blinded, four year pilot study to compare the effect of daily versus every other day glatiramer acetate 20 mg subcutaneous injections in RRMS" Neurology, 2009, vol. 72, No. 11, p. A317,submitted as Exhibit 1011 in Inter Partes Review Case Nos. IPR2015-00643, IPR2015-00644 and IPR2015-00830.
Flechter et al., Comparison of glatiramer acetate sclerosis patients: an open-label 2-year follow up, 197 Journal of the Neurological Sciences, 51-55 (2002), submitted as Exhibit 1012 in Inter Partes Review Case Nos. IPR2015-00643, IPR2015-00644 and IPR2015-00830.
Bornstein, Multiple Sclerosis: Trial of a Synthetic Polypeptide, 11:3 Annals of Neurology, 317-19 (1982), submitted as Exhibit 1014 in Inter Partes Review Case Nos. IPR2015-00643, IPR2015-00644 and IPR2015-00830.

(56) References Cited

OTHER PUBLICATIONS

Bornstein et al., Clinical Trial of Copolymer I in Multiple Sclerosis, 436 Annals New York Academy of Sciences, 366-372 (1984), submitted as Exhibit 1015 in Inter Partes Review Case Nos. IPR2015-00643, 1PR2015-00644 and IPR2015-00830.

Bornstein et al., A Pilot Trial of COP 1 in Exacerbating- Remitting Multiple Sclerosis, 317:7 The New England Journal Ofmedicine, 408-14 (1987), submitted as Exhibit 1016 in Inter Partes Review Case Nos. IPR2015-00643, IPR2013-00644 and IPR2015-00830.

Food and Drug Administration, *Guideline for Industry: Dose-Response Information to Support Drug Registration*, Federal Register vol. 59 (Nov. 9, 1994), pp. 55972-55976, submitted as Exhibit 1017 in Inter Partes Review Case Nos. IPR2015-00643, IPR2015-00644 and IPR2015-00830.

Johnson et al., Copolymer 1 reduces relapse rate and improves disability in relapsing-remitting multiple sclerosis, 43 Neurology, 1268-1276 (1995), submitted as Exhibit 1018 in Inter Partes Review Case Nos. IPR2015-00643, IPR2015-00644 and IPR2015-00830.

Affidavit of Marlene S. Bobka dated Jan. 5, 2015 together with Exhibit A, submitted as Exhibit 1019 in Inter Partes Review Case Nos. IPR2015-00643, IPR2015-00644 and IPR2015-00830.

Benet et al., "Pharmacokinetics: The Dynamics of Drug Absorption, Distribution, and Elimination" in: Goodman & Gilman, *The Pharmacological Basis of Therapeutics* (New York, McGraw-Hill, 1995), pp. 3-27, submitted as Exhibit 1021 in Inter Partes Review Case Nos. IPR2015-00643, IPR2015-00644 and IPR2015-00830.

Lobel et al., "Copolymer-1", 21(2) Drugs of the Future, 131-134 (1996), submitted as Exhibit 1022 in Inter Partes Review Case Nos. IPR2015-00643, IPR2015-00644 and IPR2015-00830.

Comi et al. (2001) "European/Canadian multicenter, double-blind, randomized, placebo-controlled study of the effects of glatiramer acetate on magnetic resonance imagine-measured disease activity and burden in patients with relapsing multiple sclerosis". Ann Neurol. 49:290-7, submitted as Exhibit 1026 in Inter Partes Review Case Nos. IPR2015-00643, IPR2015-00644 and IPR2015-00830.

Jean-Pierre Boissel et al. "Using pharmacokinetic-pharmacodynamic relationships to predict the effect of poor compliance," Clin. Pharmacol. 41:1-6 (2002), submitted as Exhibit 1027 in Inter Partes Review Case Nos. IPR2015-00643 and IPR2015-00643.

McBride, "Nonadherence to Immunomodulation in Multiple Sclerosis," abstract for Second International Multiple Sclerosis Week Multiple Sclerosis: A World View, a conference held on Jun. 5-9, 2002 at Chicago, Illinois, submitted as Exhibit 1028 in Inter Partes Review Case Nos. IPR2015-00643, IPR2015-00644 and IPR2015-00830.

Simpson et al., Adis Drug Evaluation—Glatiramer Acetate A Review of its use in Relapsing-Remitting Multiple Sclerosis, 16:12 CNS Drugs, 825-50, 834 (2002), submitted as Exhibit 1029 in Inter Partes Review Case Nos. IPR2015-00643, IPR2015-00644 and IPR2015-00830.

Edgar, et al., "Lipoatrophy in Patients with Multiple Sclerosis on Glatiramer Acetate", 31 Can. J. Nenrol. Sci., 58-63 (2004), submitted as Exhibit 1030 in Inter Partes Review Case Nos. IPR2015-00643, IPR2015-00644 and IPR2015-00830.

Beringer at al., "Clinical Pharmacokinetics and Pharmacodynamics", in *Remington: The Science and Practice of Pharmacy* (Philadelphia, Lippincott Williams & Wilkins, 2005), pp. 1191-1205, submitted as Exhibit 1034 in Inter Partes Review Case Nos. IPR2015-00643, IPR2015-00644 and IPR2015-00830.

Franklin at al., "Drug Absorption, Action, and Disposition", in *Remington: The Science and Practice of Pharmacy* (Philadelphia, Lippincott Williams & Wilkins, 2005), 1142-1170, submitted as Exhibit 1035 in Inter Partes Review Case Nos. IPR2015-00643, IPR2015-00644 and IPR2015-00830.

International Application Publication No. WO 2005/120542, published Dec. 22, 2005 (Rasmussen), submitted as Exhibit 1036 in Inter Partes Review Case Nos. IPR2015-00643, IPR2015-00644 and IPR2015-00830.

Devonshire et al., "The Global Adherence Project—A Multicentre Observational Study on Adherence to Disease-Modifying Therapies in Patients Suffering from Relapsing-Remitting Multiple Sclerosis", Multiple Sclerosis 12:S1 (P316), 2006 (abstract)[online], [retrieved on Nov. 18, 2014]. Retreived from the Internet <URL: msj.sagepub.com/content/12/1_suppl/S1.citation> submitted as Exhibit 1037 in Inter Partes Review Case Nos. IPR2015-00643, IPR2015-00644 and IPR2015-00830.

Ford et al., "A Prospective Open-Label Study of Glatiramer Acetate: Over a Decade of Continuous Use in Multiple Sclerosis Patients", 12 Multiple Sclerosis, 309-320 (2006), submitted as Exhibit 1038 in Inter Partes Review Case Nos. IPR2015-00643, IPR2015-00644 and IPR2015-00830.

Manso et al., "Life Cycle Management of Ageing Pharmaceutical Assets", 3:7 Pharmaceutical Law Insight, (2006), submitted as Exhibit 1041 in Inter Partes Review Case Nos. IPR2015-00643, IPR2015-00644 and IPR2015-00830.

Almeida et al., "Localized Panniculitis Secondary to Subcutaneous Glatiramer Acetate Injections for the Treatment of Multiple Sclerosis: A Clinicopathologic and Immunohistcchemical Study", J. Am. Acad. Dermatol 55:968-74 (2006), submitted as Exhibit 1042 in Inter Partes Review Case Nos. IPR2015-00643, IPR2015-00644 and IPR2015-00830.

Klauer and Zettl, "Compliance, Adherence and the Treatment of Multiple Sclerosis", J. Neurol. 255 [Suppl.6]:87-92 (2008), submitted as Exhibit 1043 in Inter Partes Review Case Nos. IPR2015-00643, IPR2015-00644 and IPR2015-00830.

Teva Provides Update on Forte Trial, published on Jul. 7, 2008 at Jerusalem, Israel by Teva Pharmaceutical Industries Ltd. submitted as Exhibit 1046 in Inter Partes Review Case Nos. IPR2015-00643, IPR2015-00644 and IPR2015-00830.

Interferon Beta 1b (Extavia®), Abbreviated National Drug Monograph, published Sep. 2010 by VA Pharmacy Benefits Management Services, Medical Advisory Panel and VISN Pharmacist Executives, submitted as Exhibit 1053 in Inter Partes Review Case Nos. IPR2015-00643, IPR2015-00644 and IPR2015-00830.

Copaxone®, Food and Drug Administration Approved Labeling, Jan. 2014, submitted as Exhibit 1057 in Inter Partes Review Case No. IPR2015-00643.

Thixia, "Copaxone". In Multiple Sclerosis All about MS [online], Apr. 11, 2008 [retrieved on Feb. 5, 2015]. Retrieved from the Internet: <URL:scamparoo.wordpress.com/2008/04/11/ms-therapies-copaxone/>, submitted as Exhibit 1058 in Inter Partes Review Case No. IPR2015-00643, and Exhibit 1062 in Inter Partes Review Case Nos. IPR2015-00644.

Guidance for Industry Population Pharmacokinetics [online]. Food and Drug Administration, Feb. 1999 [retrieved on Jun. 23, 2015]. Retrieved from the Internet: <URL:www.fds.gov/downloads/Drugs/Guidances/UCM072137.pdf>, submitted at Exhibit 1063 in IPR2015-00643 and Exhibit 1059 in Inter Partes Review Case Nos. IPR2015-00644 and IPR2015-00830.

Mar. 25, 2013 Office Action, issued in connection with Taiwanese Patent Application No. 100103482 together with an English language translation thereof.

Sep. 25, 2013 Communication in Response to Mar. 25, 2013 Office Action, filed in connection with Taiwanese Patent Application No. 100103482 together with an English language translation thereof.

Feb. 25, 2014 Office Action, issued in connection with Mexican Patent Application No. Mx/a/2012/000687 together with an English language summary thereof.

Jun. 25, 2014 Amendment in Response to Feb. 25, 2014 Office Action, filed in connection with Mexican Patent Application No. Mx/a/2012/000687 together with an English language translation thereof.

Oct. 10, 2014 Office Action, issued in connection with Mexican Patent Application No. Mx/a/2012/000687 together with an English language summary thereof.

Dec. 19, 2014 Amendment in Response to Oct. 20, 2014 Office Action, filed in connection with Mexican Patent Application No. Mx/a/2012/000687 together with an English language translation thereof.

Mar. 4, 2015 Office Action, issued in connection with Mexican Patent Application No. Mx/a/2012/000687 together with an English language summary thereof.

(56) References Cited

OTHER PUBLICATIONS

Dec. 11, 2014 Amendment in Response to Aug. 11, 2014 Official Action, filed in connection with Eurasian Patent Application No. 201270167 together with an English language translation thereof.
Aug. 11, 2014 Office Action, issued in connection with Eurasian Patent Application No. 201270167 together with an English language translation thereof.
Mar. 21, 2014 Office Action, issued in connection with Eurasian Patent Application No. 201270167 together with an English language translation thereof.
Jul. 21, 2014 Amendment in Response to Mar. 21, 2014 Official Action, filed in connection with Eurasian Patent Application No. 201270167 together with an English language translation thereof.
Feb. 14, 2014 Amendment in Response to Oct. 16, 2013 Office Action, filed in connection with Eurasian Patent Application No. 201270167 together with an English language translation thereof.
Oct. 16, 2013 Office Action, issued in connection with Eurasian Patent Application No. 201270167 together with an English language translation thereof.
Aug. 19, 2014 Office Action, issued in connection with Japanese Patent Application No. 2012-520598 together with an English language translation thereof.
Dec. 19, 2014 Amendment in Response to Aug. 19, 2014 Office Action, filed in connection with Japanese Patent Application No. 2012-520598 together with an English language translation thereof.
Jul. 18, 2013 Application to Amend a Complete Specification, filed in connection with South African Application No. 2012/00586 (Klinger).
Jan. 15, 2015 Official Action Issued in Connection With Canadian Application No. 2,760,802, filed Aug. 19, 2012 (Klinger).
Sep. 23, 2014 Reply to Oppositions filed against EP2405739B in the name of Yeda Research Development Co Ltd. By Activis Group PTC ehf and others in connection with European Application No. 10810282.3 (Klinger).
Jun. 4, 2015 Amendment in Response to Jan. 7, 2014 Official Action filed in Connection With Japanese Application No. 2012-525530, filed Feb. 20, 2012 (Klinger) together with an English translation thereof.
May 26, 2015 Yeda's Patent Owner Preliminary Response filed in connection with *Mylan Pharmaceuticals Inc.* v. *Yeda Research & Development Co. Ltd.* for U.S. Pat. No. 8,232,250 in the United States Patent and Trademark Office Patent Trial and Appeal Board (Case No. IPR2015-00643).
May 26, 2015 Yeda's Patent Owner Preliminary Response filed in connection with *Mylan Pharmaceuticals Inc.* v. *Yeda Research & Development Co. Ltd.* for U.S. Pat. No. 8,399,413 in the United States Patent and Trademark Office Patent Trial and Appeal Board (Case No. IPR2015-00644).
Jun. 19, 2015 Yeda's Patent Owner Preliminary Response filed in connection with *Mylan Pharmaceuticals Inc.* v. *Yeda Research & Development Co. Ltd.* for U.S. Pat. No. 8,969,302 in the United States Patent and Trademark Office Patent Trial and Appeal Board (Case No. IPR2015-00830).
Teva Provides Update on Forte Trial, published on Jul. 7, 2008 at Jerusalem, Israel by Teva Pharmaceutical Industries Ltd., submitted as Exhibit 2001 in Inter Partes Review Case Nos. IPR2015-00643 and IPR2015-00644 and IPR2015-00830.
Franscisco J. Quintana et al., "Systems Biology Approaches for the Study of Multiple Sclerosis", 12 J. Cell. Mol. Med. 4, 1087-93 (2008), submitted as Exhibit 2002 in Inter Partes Review Case Nos. IPR2015-00643 and IPR2015-00644 and IPR2015-00830.
David J. Virley, "Developing Therapeutics for the treatment of multiple sclerosis", 2 The Journal of the American Society for Experimental NeuroTherapeutics, 638-49 (Oct. 2005), submitted as Exhibit 2003 in Inter Partes Review Case Nos. IPR2015-00643 and IPR2015-00644 and IPR2015-00830.
Manuel A. Friese et al., "The value of animal models for drug development in multiple sclerosis", 129 Brain, 1940-52 (2006), submitted as Exhibit 2004 in Inter Partes Review Case Nos. IPR2015-00643 and IPR2105-00644 and IPR2015-00830.

Copaxone®, Food and Drug Administration Approved Labeling, Jan. 2014, submitted as Exhibit 2005 in Inter Partes Review Case Nos. IPR2015-00643 and IPR2015-00644 and IPR2015-00830.
Dvora Teitelbaum et al., "Suppression of experimental allergic encephalomyelitis by a synthetic polypeptide", 1 Eur. J. Immunol., 242-248 (Aug. 1971), submitted as Exhibit 2006 in Inter Partes Review Case Nos. IPR2015-00643 and IPR2015-00644 and IPR2015-00830.
Jill Conner, "Glatiramer acetate and therapeutic peptide vaccines for multiple sclerosis", 1 J. Autoimmunity and Cell Responses 3 (2014), submitted as Exhibit 2007 in Inter Partes Review Case Nos. IPR2015-00643 and IPR2015-00644 and IPR2015-00830.
Copaxone®, Physicians' Desk Reference, 62nd ed. Montvale, NJ, Thomson Healthcare Inc., pp. 3231-3235 (2008), submitted as Exhibit 2008 in Inter Partes Review Case Nos. IPR2015-00643 and IPR2015-00644 and IPR2015-00830.
Wiebke Schrempf and Tjalf Ziemssen, "Glatiramer acetate: Mechanisms of action in multiple sclerosis", 6 Autoimmunity Reviews, 469-475 (2007), submitted as Exhibit 2009 in Inter Partes Review Case Nos. IPR2015-00643 and IPR2015-00644 and IPR2015-00830.
V. Wee Yong, "Differential mechanisms of action of interferon-β and glatiramer acetate in MS", 59 Neurology, 802-8 (Apr. 2002), submitted as Exhibit 2010 in Inter Partes Review Case Nos. IPR2015-00643 and IPR2015-00644 and IPR2015-00830.
Suhayl Dhib-Jalbut, "Mechanisms of action of interferons and glatiramer acetate in multiple sclerosis", 58 Neurology (8 Suppl 4), S3-9 (2002), submitted as Exhibit 2011 in Inter Partes Review Case Nos. IPR2015-00643 and IPR2015-00644 and IPR2015-00830.
Oliver Neuhaus et al., "Pharmacokinetics and pharmacodynamics of the interferon-betas, glatiramer acetate, and mitoxantrone in multiple sclerosis", 259 Journal of the Neurological Sciences, 27-37 (2007), submitted as Exhibit 2012 in Inter Partes Review Case Nos. IPR2015-00643 and IPR2015-00644 and IPR2015-00830.
Oded Abramsky et al., "Effect of a Synthetic Polypeptide (COP 1) on Patients With Multiple Sclerosis and With Acute Disseminated Encephalomyelitis. Preliminary Report", 31 Journal of the Neurological Sciences, 433-38 (1977), submitted as Exhibit 2013 in Inter Partes Review Case Nos. IPR2015-0C643 and IPR2015-00644 and IPR2015-00830.
Murry B. Bornstein et al., "Treatment of Multiple Sclerosis with a Synthetic Polypeptide: Preliminary Results", in *Transactions of the American Neurological Association*, 1980, vol. 105 (New York, Springer Publishing Company), pp. 348-50, submitted as Exhibit 2014 in Inter Partes Review Case Nos. IPR2015-00643 and IPR2015-00644 and IPR2015-00830.
Murry B. Bornstein et al., "Treatment Multiple Sclerosis: Trial of a Synthetic Polypeptide", 11 Ann. Neurol., 317-19 (Mar. 1982), submitted as Exhibit 2015 in Inter Partes Review Case Nos. IPR2015-00643 and IPR2015-00644 and IPR2015-00830.
Murry B. Bornstein et al., "A Pilot Trial of COP 1 in Exacerbating-Remitting Multiple Sclerosis", 13 N. Engl. J. Med., 408-14 (Aug. 13, 1987), submitted as Exhibit 2016 in Inter Partes Review Case Nos. IPR2015-00643 and IPR2015-00644 and IPR2015-00830.
Table of Contents—Sep. 2008; 14(1 suppl) [online]. Sage Journals [retrieved May 22, 2015]. Retrieved from the Internet: <URL msj.sagepub.com/content/14/1_suppl.toc>, submitted as Exhibit 2017 in Inter Partes Review Case Nos. IPR2015-00643 and IPR2015-00644 and IPR2015-00830.
Massimo Filippi et al., "Effects of oral glatiramer acetate on clinical and MRI monitored disease activity in patients with relapsing multiple sclerosis: a multicentre, double-blind, randomised, placebo-controlled study", Lancet Neurol. Jan. 20, 2006 [online], Retrieved from the Internet <URL:neurology.thelancet.com> <DOI:10.1016/S1474-4422(06)70327-1>, submitted as Exhibit 2018 in Inter Partes Review Case Nos. IPR2015-00643 and IPR2015-00644 and IPR2015-00830.
Yuval Ramot et al., "Comparative Long-Term Preclinical Safety Evaluation of Two Glatiramoid Compounds (Glatiramer Acetate, Copaxonel, and TV- 5010, Protiramer) in Rats and Monkeys", 40 Toxicol. Path., 40-54 (2012), submitted as Exhibit 2019 in Inter Partes Review Case Nos. IPR2015-00643 and IPR2015-00644 and IPR2015-00830.

(56) References Cited

OTHER PUBLICATIONS

U.S. Patent Application No. 2007/0161566 A1 ("Pinchasi"), submitted as Exhibit 2020 in inter Partes Review Case Nos. IPR2015-00643 and IPR2015-00644 and IPR2015-00830.

Tjalf Ziemssen et al., "Risk-Benefit Assessment of Glatiramer Acetate in Multiple Sclerosis", 24 Drug Safety, 13, 979-90 (2001), submitted as Exhibit 2021 in Inter Partes Review Case Nos. IPR2015-00643 and IPR2015-00644 and IPR2015-00830.

"News Release, Phase III Data Published in Annals of Neurology Show That a Higher Concentration Dose of Glatiramer Acetate Given Three Times a Week Reduced Annualized Relapse Rates in the Treatment of Relapsing-Remitting Multiple Sclerosis" [online] Teva Pharmaceutical Industries Ltd. Jul. 1, 2013 [retrieved on May 22, 2015]. Retrieved from the Internet: <URL:ir.tevapharm.com/phoenix.zbtml?c=73925&p=irol-newsArticle Print&ID= 1834170>, submitted as Exhibit 2022 in Inter Partes Review Case Nos. IPR2015-00643 and IPR2015-00644 and IPR2015-00830.

Omar Khan et al., "Three Times Weekly Glatiramer Acetate in Relapsing-Remitting Multiple Sclerosis", 73 Ann. Neurol., 705-13 (2013), submitted as Exhibit 2023 in Inter Partes Review Case Nos. IPR2015-00643 and IPR2C15-00644 and IPR2015-00830.

"Teva Reports First Quarter 2015 Results"; Apr. 30, 2015, Jerusalem, Teva Press Release, submitted as Exhibit 2024 in Inter Partes Review Case Nos. IPR2015-00643 and IPR2015-00644 and IPR2015-00830.

Kate McKeage, "Glatiramer Acetate 40 mg/mL in Relapsing-Remitting Multiple Sclerosis: A Review", CNS Drugs, Apr. 24, 2015, submitted as Exhibit 2025 in Inter Partes Review Case Nos. IPR2015-00643 and IPR2015-00644 and IPR2015-00830.

K.P. Johnson et al., "Copolymer 1 reduces relapse rate and improves disability in relapsing-remitting multiple sclerosis: Results of a phase I11 multicenter, double- blind, placebo- controlled trial", 45 Neurology, 1268-76 (1995), submitted as Exhibit 2026 in Inter Partes Review Case Nos. IPR2015-00643 and IPR2015-00644 and IPR2015-00830.

*Webster's Ninth New Collegiate Dictionary*, Merriam-Webster, Inc., 1985, p. 872, submitted as Exhibit 2027 in Inter Partes Review Case No. IPR2015-00830.

Decision rejecting the opposition (Art. 101(2) EPC) issued by the European Patent Office on Jan. 19, 2016 in connection with Opposition filed against EP2405749B.

Dec. 7, 2015 Information on Oral Proceedings issued by the European Patent Office in connection with Opposition filed against EP2405749B.

Apr. 23, 2015 Summons to attend oral proceedings pursuant to Rule 115(1) EPC and Communication accompanied by Summons (EPO form 2906) issued by the European Patent Office in connection with Opposition filed against EP2405749B.

Oct. 7, 2015 Letter accompanied by Comments in advance to Oral Proceedings scheduled for 7th Dec. 2015 filed by Yeda Research Development Co., Ltd. with the European Patent Office in connection with Opposition filed against EP2405749B.

Nov. 9, 2015 Reply, filed by Synthon B.V. with the European Patent Office in connection with Opposition filed against EP2405749B.

Patent Application Publication No. 2007-0161566, published Jul. 12, 2007 (Pinchasi), submitted as Exhibit D1 of Opposition filed against EP2405749B.

Fletcher et al., "Comparison of glatiramer acetate (Copaxone®) and interferon β-1b (Betaferon ®) in multiple sclerosis patients: an open-label 2-year follow-up" J. Neural Sci vol. 197, pp. 51-55, submitted as Exhibit D2 of Opposition filed against EP2405749B.

Fletcher et al., "Copolymer 1 (Glatiranler Acetate) in Relapsing Forms of Multiple Sclerosis: Open Multicenter Study of Alternate-Day Adn1inistration" Clin Neuropharm 2002, vol. 25(1), pp. 11-15, submitted as Exhibit D3 of Opposition filed against EP2405749B.

Khan et al., Randomized, prospective, rater-blinded, four-year, pilot study to compare the effect of daily versus every-other-day glatiramer acetate 20 mg subcutaneous injections in relapsing-remitting multiple sclerosis Multiple Sclerosis 2008, vol. 14, 5295, submitted as Exhibit D4 of Opposition filed against EP2405749B.

Caon et al., "Randomized, Prospective, Rater-Blinded, Four Year Pilot Study to Compare the Effect of Daily Versus Every Other Day Glatiramer Acetate 20 mg Subcutaneous Injections in Rrms" Neurobiology 2008, vol. 68 (12), Suppl 3, submitted as Exhibit D5 of Opposition filed against EP2405749B.

Cohen et al. "Randomized, double-blind, dose-comparision study of glatiramer acetate relapsing-remitting MS", Neurology 2007, vol. 68 (12), pp. 939-944, submitted as Exhibit D6 of Opposition filed against EP2405749B.

Simpson et al., "Glatiramer Acetate: A review of its Use in relapsing-Remitting Multiple Sclerosis" Adis Drug Evaluation, Glatiramer Acetate, 2002, submitted as Exhibit D7 of Opposition filed against EP2405749B.

Teva Provides Update on Forte Trial, published on Jul. 7, 2008 at Jerusalem, Israel by Teva Pharmaceutical Industries Ltd., submitted as Exhibit D8 of Opposition filed against EP2405749B.

"News Release, Teva to Present Positive Data for Glatiramer Acetate 40 mg/lml Given Three Times Weekly for Relapsing-Remitting MS" [online] Teva Pharmaceutical Industries Ltd. Oct. 10, 2012 [retrieved on Apr. 2, 2013]. Retrieved from the Internet: <URL://www.tevapharm.com/Media/News/Pages/2012/1743500.aspx?year=2012 &page . . . >, submitted as Exhibit D9 of Opposition filed against EP2405749B.

Kahn et al, "Late Breaking News II: A phase 3 trial to assess the efficacy and Safety of glatiramer acetate injections 40mg administered 3 times a week compared to placebo", abstract presented on Oct. 13, 2012 at the 28th Congress of the European Committee for Treatment and Research in Multiple Sclerosis held at Lyon France on Oct. 10-13, 2012, submitted as Exhibit D10 of Opposition filed against EP2405749B.

"Copaxone 20mg/ml, Solution for Injection, Pre-filled Syringe" [online] Teva Pharmaceutical Ltd., Feb. 3, 2009 [retrieved on Jan. 27, 2013]. Retrieved from the Internet: <URL://www.medicines.org.uk/EMC/printfriendlydocument.aspx?documentid=17516>>, submitted as Exhibit D11 of Opposition filed against EP2405749B.

PCT International Application Publication No. WO 2005/00120542, Published Dec. 22, 2005 (Rasmussen at al.), submitted as Exhibit D12 of Opposition filed against EP2405749B.

US Application Publication No. 2005-0014696, published Jan. 20, 2005 (Yong et al.), submitted as Exhibit D13 of Opposition filed against EP2405749B.

US Application Publication No. 2009-0149541, published Jun. 11, 2009 (Stark et al.), submitted as Exhibit D14 of Opposition filed against EP2405749B.

Yong et al. "Immunological response to different doses of GA in MS: Analyses from the FORTE trial" dated Apr. 28 2009, Abstract only, submitted as Exhibit D15 of Opposition filed against EP2405749B.

Jul. 1, 2009 Response to Apr. 2, 2009 Final Office Action filed with the U.S. Patent and Trademark Office in connection with U.S Appl. No. 11/651,212, submitted as Exhibit D16 of Opposition filed against EP2405749B.

International Application Publication No. WO 00/18794, published Apr. 6, 2000 (Gad et al.), submitted as Exhibit D17 of Opposition filed against EP2405749B.

Sep. 13, 2012 Response to Aug. 8, 2015 Communication pursuant to Article 94(3) EPC filed with the European Patent Office in connection with European Patent Application No. 10810282.3, submitted as Exhibit D18 of Opposition filed against EP2405749B.

Comi et al. "Results from a phase II, 1-year, Randomized, Double-blind, Parallel-Group, Dose Comparison Study with Glatiramer Acetate in Relapsing-remitting Multiple Sclerosis", abstract at the World Congress on Treatment and Research in Multiple Sclerosis—Montreal 2008, presented on Sep. 20, 2008, [online] [retrieved on Aug. 21, 2015]. Retrieved from the Internet: <URL://www.multiwebcast.com/wctrims/2008/msmontreal/2448/chair.giancarlo.comi.r . . . >submitted as Exhibit D19 of Opposition filed against EP2405749B.

Slides of G. Comi, Forte: Results from a phase II, 1-year, Randomized, Double-blind, Parallel-Group, Dose Comparison Study with Glatiramer Acetate in Relapsing-remitting Multiple Sclerosis, Presented at World Congress on Treatment and Research in Multiple Sclerosis: 2008 Joint Meeting of the American, European, and Latin America Committees on Treatment and Research in Multiple Scle-

(56) References Cited

OTHER PUBLICATIONS rosis, San Raffaele, Italy (ACTRIMS, ECTRIMS, LACTRIMS) (2008), submitted as Exhibit D19a of Opposition filed against EP2405749B.
Oct. 2, 2015 Expert Report of Dr Simon Day, submitted as Exhibit D20 of Opposition filed against EP2405749B.
"News Release: Teva Initiates Phase III Study to Confirm Increased Efficacy of Higher Dose of Glatiramer Acetate for the Treatment of Relapsing-Remitting Multiple Sclerosis" [online] Teva Pharmaceutical Industries Ltd., Jul. 27, 2006 [retrieved on Apr. 6, 2015]. Retrieved from the Internet: <URL://ir.tevapharm.com/phoenix.zhtml?c=73925&p=irol-newsArticle&ID=1557343>, submitted as Exhibit D21 of Opposition filed against EP2405749B.
"News Release: Data Published in Neurology Showed That Higher Dose of Copaxone® Increased Efficacy in Relapsing-Remitting Multiple Sclerosis (Rrms)" [online] Teva Pharmaceutical Industries Ltd., Apr. 17, 2007 [retrieved on Apr. 6, 2015]. Retrieved from the Internet: <URL://ir.tevapharm.com/phoenix.zhtml?c=73925&p=irol-newsArticle&ID=1554611>, submitted as Exhibit D22 of Opposition filed against EP2405749B.
"Medscape Medical News: Doubling the Dose of Glatiramer Acetate Does Not Increase Efficacy" [online] Medscape, Sep. 22, 2008, [retrieved on Jan. 6, 2015]. Retrieved from the Internet: <URL://www.medscape.com/viewartice/580865>, submitted as Exhibit D23 of Opposition filed against EP2405749B.
"Daily News: High-dosage Copaxone trial results are bad news for Teva" [online] PharmaTimes, Jul. 7, 2008, [retrieved on Nov. 6, 2015]. Retrieved from the Internet: <URL://http://www.pharmatimes.com/article/08-07-07/High-dosage_Copaxone_trial_results . . . >, submitted as Exhibit D24 of Opposition filed against EP2405749B.
Committee for Medicinal Products for Human Use (CHMP) "Guidelines on Clinical Investigation of Medicinal Products for the Treatment of Multiple Sclerosis", European Medicines Agency, Nov. 16, 2006, submitted as Exhibit D25 of Opposition filed against EP2405749B.
Varkoni et al. "The glatiramoid class of immunomodulator Drugs" Expert Opinion on Pharmacotherapy 2009 10(4) 657-668, submitted as Exhibit D26 of Opposition filed against EP2405749B.
Meiner et al. in "Frontiers in Multiple Sclerosis: Clinical research and Therapy" Eds Abramsky & Ovadia (1997) 213-221, submitted as Exhibit D27 of Opposition filed against EP2405749B.
McKeage "Glatiramer Acetate 40 mg/mL in Relapsing-Remitting Multiple Sclerosis: A Review" ADIS Drug Evaluation, Apr. 2015, submitted as Exhibit D28 of Opposition filed against EP2405749B.
Wolinsky "Reduced frequency severity of injection site reactions with glatiramer acetate 40mg/mL three times weekly dosing" ECTRIMS/ECTRIMS Conference, Sep. 10-13, 2014, poster, submitted as Exhibit D29 of Opposition filed against EP2405749B.
Wolinsky et al. "Reduced frequency severity of injection site reactions with glatiramer acetate 40mg/mL three times weekly dosing", poster presented at the Joint Americas Committee for Treatment and Research in Multiple Sclerosis (ECTRIMS) Meeting, held on Sep. 10-13, 2014 at Boston MA, submitted as Exhibit D30 of Opposition filed against EP2405749B.
Oct. 5, 2015 Expert Report of Professor Wolfgang Bruck, submitted as Exhibit D31 of Opposition filed against EP2405749B.
Multiple Sclerosis Society of Canada "Talking About Clinically Isolated Syndrome or CIS" published by Communications and Services, Multiple Sclerosis Society of Canada, Quebec Division, dated 2009, submitted as Exhibit D32 of Opposition filed against EP2405749B.
Affidavit of Marlene S. Bobka dated Nov. 10, 2014, submitted as Exhibit D35 of Opposition filed against EP2405749B.
Aug. 25, 2015 Decision on Institution of Inter Partes Review, entered in connection with *Mylan Pharmaceuticals Inc.* v. *Yeda Research & Development Co., Ltd.* for U.S. Pat. No. 9,232,250 in the United States Patent and Trademark Office Patent Trial and Appeal Board (Case No. IPR2015-00643).
Aug. 25, 2015 Decision on Institution of Inter Partes Review, entered in connection with *Mylan Pharmaceuticals Inc.* v. *Yeda Research &* *Development Co., Ltd.* for U.S. Pat. No. 8,399,413 in the United States Patent and Trademark Office Patent Trial and Appeal Board (Case No. IPR2015-00644).
Sep. 1, 2015 Decision on Institution of Inter Partes Review, entered in connection with *Mylan Pharmaceuticals Inc.* v. *Yeda Research & Development Co., Ltd.* for U.S. Pat. No. 8,969,302 in the United States Patent and Trademark Office Patent Trial and Appeal Board (Case No. IPR2015-00830).
Nov. 20, 2015 Yeda's Patent Owner Response filed in connection with *Mylan Pharmaceuticals Inc.* v. *Yeda Research & Development Co. Ltd.* for U.S. Pat. No. 8,232,250 in the United States Patent and Trademark Office Patent Trial and Appeal Board (Case No. IPR2015-00643).
Nov. 20, 2015 Yeda's Patent Owner Response filed in connection with *Mylan Pharmaceuticals Inc.* v. *Yeda Research & Development Co. Ltd.* for U.S. Pat. No. 8,399,413 in the United States Patent and Trademark Office Patent Trial and Appeal Board (Case No. IPR2015-00644).
Nov. 25, 2015 Yeda's Patent Owner Response filed in connection with *Mylan Pharmaceuticals Inc.* v. *Yeda Research & Development Co. Ltd.* for U.S. Pat. No. 8,969,302 in the United States Patent and Trademark Office Patent Trial and Appeal Board (Case No. IPR2015-00830).
Declaration of Edward J. Fox, Md., PhD in Support of Patent Owner Yeda's Response to Institution of Inter Partes Review filed on Nov. 20, 2015, submitted as Exhibit 2129 in Inter Partes Review Case No. IPR2015-00643.
Declaration of Edward J. Fox, Md., PhD in Support of Patent Owner Yeda's Response to Institution of Inter Partes Review filed on Nov. 20, 2015, submitted as Exhibit 2129 in Inter Partes Review Case No. IPR2015-00644.
Declaration of Edward J. Fox, Md., PhD in Support of Patent Owner Yeda's Response to Institution of Inter Partes Review filed on Nov. 25, 2015, submitted as Exhibit 2129 in Inter Partes Review Case No. IPR2015-00830.
Declaration of Henry G. Grabowski, Ph.D. in Support of Patent Owner Yeda's Response to Institution of Inter Partes Review filed on Nov. 20, 2015, submitted as Exhibit 2133 in Inter Partes Review Case No. IPR2015-00643.
Declaration of Henry G. Grabowski, Ph.D. in Support of Patent Owner Yeda's Response to Institution of Inter Partes Review filed on Nov. 20, 2015, submitted as Exhibit 2133 in Inter Partes Review Case No. IPR2015-00644.
Declaration of Henry G. Grabowski, Ph.D. in Support of Patent Owner Yeda's Response to Institution of Inter Partes Review filed on Nov. 25, 2015, submitted as Exhibit 2133 in Inter Partes Review Case No. IPR2015-00830.
Declaration of Robert William Gristwood, Ph.D. in Support of Patent Owner Yeda's Response to Institution of Inter Partes Review filed on Nov. 20, 2015, submitted as Exhibit 2134 in Inter Partes Review Case No. IPR2015-00643.
Declaration of Robert William Gristwood, Ph.D. in Support of Patent Owner Yeda's Response to Institution of Inter Partes Review filed on Nov. 20, 2015, submitted as Exhibit 2134 in Inter Partes Review Case No. IPR2015-00644.
Declaration of Robert William Gristwood, Ph.D. in Support of Patent Owner Yeda's Response to Institution of Inter Partes Review filed on Nov. 25, 2015, submitted as Exhibit 2134 in Inter Partes Review Case No. IPR2015-00830.
Declaration of Tjalf Ziemssen, M.D., Ph.D in Support of Patent Owner Yeda's Response to Institution of Inter Partes Review filed on Nov. 20, 2015, submitted as Exhibit 2135 in Inter Partes Review Case No. IPR2015-00643.
Declaration of Tjalf Ziemssen, M.D., Ph.D in Support of Patent Owner Yeda's Response to Institution of Inter Partes Review filed on Nov. 20, 2015, submitted as Exhibit 2135 in Inter Partes Review Case No. IPR2015-00644.
Declaration of Tjalf Ziemssen, M.D., Ph.D in Support of Patent Owner Yeda's Response to Institution of Inter Partes Review filed on Nov. 25, 2015, submitted as Exhibit 2135 in Inter Partes Review Case No. IPR2015-00830.
Deposition of Stephen J. Peroutka, M.D., Ph.D., taken on behalf of the Patent Owner Yeda, at 901 New York Avenue, Washington, D.C.,

(56) References Cited

OTHER PUBLICATIONS beginning at 9:30 a.m. on Oct. 29, 2015, before Michele E. Eddy, RPR, CRR, CLR, and Notary Public for the District of Columbia, submitted as Exhibit 1066 in Inter Partes Review Case Nos. IPR2015-00643, IPR2015-00644 and IPR2015-00830 on Nov. 18, 2015.

Slides of G. Comi, Forte: Results from a phase II, 1-year, Randomized, Double-blind, Parallel-Group, Dose Comparison Study with Glatiramer Acetate in Relapsing-remitting Multiple Sclerosis, Presented at World Congress on Treatment and Research in Multiple Sclerosis: 2008 Joint Meeting of the American, European, and Latin America Committees on Treatment and Research in Multiple Sclerosis, San Raffaele, Italy (ACTRIMS, ECTRIMS, LACTRIMS) (2008), submitted as Exhibit 2028 in Inter Partes Review Case Nos. IPR2015-00643, IPR2015-00644 and IPR2015-00830.

Jerry S. Wolinsky et al., "GLACIER: An open-label, randomized, multicenter study to assess the safety and tolerability of glatiramer acetate 40 mg three times weekly versus 20 mg daily in patients with relapsing-remitting multiple sclerosis", 4 Multiple Sclerosis and Related Disorders 370 (2015), submitted as Exhibit 2029 in Inter Partes Review Case Nos. IPR2015-00643, IPR2015-00644 and IPR2015-00830.

C. Farina et al., "Treatment of multiple sclerosis with Copaxone (COP): Elispot assay detects COP-induced interleukin-4 and interferon-gamma response in blood cells." 124 Brain 705 (2001), submitted as Exhibit 2030 in Inter Partes Review Case Nos. IPR2015-00643, IPR2015-00644 and IPR2015-00830.

PRA, Multiple Sclerosis: Transform Your Clinical Trial with PRA (2012), submitted as Exhibit 2031 in Inter Partes Review Case Nos. IPR2015-00643, IPR2015-00644 and IPR2015-00830.

Opinion, *Endo Pharmaceuticals, Inc.* v. *Mylan Pharmaceuticals, Inc.*, No. 11-cv-00717, Document 226 (Jan. 28, 2014), submitted as Exhibit 2032 in Inter Partes Review Case Nos. IPR2015-00643, IPR2015-00644 and IPR2015-00830.

Donna Oksenberg et al., "A single amino acid difference confers major pharmacological variation between human and rodent 5-HT-1B receptors", 360 Nature 161 (1992), submitted as Exhibit 2033 in Inter Partes Review Case Nos. IPR2015-00643, IPR2015-00644 and IPR2015-00830.

Shalit et al., "Copolymer-1 (Copaxone®) induces in non-immunologic activation of connective tissue type mast cells", 97(1) J. Allergy and Clinical Immunology 345 (1996), submitted as Exhibit 2034 in Inter Partes Review Case Nos. IPR2015-00643, IPR2015-00644 and IPR2015-00830.

Order, *Endo Pharmaceuticals, Inc.* v. *Mylan Pharmaceuticals, Inc.*, No. 11-cv-00717, Document 310 (Apr. 8, 2014), submitted as Exhibit 2035 in Inter Partes Review Case Nos. IPR2015-00643, IPR2015-00644 and IPR2015-00830.

M. Fridkis-Hareli et al., "Binding motifs of copolymer 1 to multiple sclerosis-and rheumatoid arthritis-associated HLA-DR molecules." 15;162(8):4697-704. (Apr. 1999), submitted as Exhibit 2036 in Inter Partes Review Case Nos. IPR2015-00643, IPR2015-00644 and IPR2015-00830.

Notice of Abandonment issued Mar. 9, 2010 for U.S. Appl. No. 11/651,212, submitted as Exhibit 2037 in Inter Partes Review Case Nos. IPR2015-00643, IPR2015-00644 and IPR2015-00830.

B. Meibohm et al., "Basic concepts of pharmacokinetic/pharmacodynamic (PK/PD) modelling." 35(10), 401-413 (1997), submitted as Exhibit 2038 in Inter Partes Review Case Nos. IPR2015-00643, IPR2015-00644 and IPR2015-00830.

P.H. Lambert et al., "Intradermal vaccine delivery: will new delivery systems transform vaccine administration?" 26(26) Vaccine, 3197-208 (2008); submitted as Exhibit 2039 in Inter Partes Review Case Nos. IPR2015-00643, IPR2015-00644 and IPR2015-00830.

G. Glenn et al., "Transcutaneous immunization and immunostimulant strategies", 23(4) Immunology and Allergy Clinics of N. Am., 787-813 (2003), submitted as Exhibit 2040 in Inter Partes Review Case Nos. IPR2015-00643, IPR2015-00644 and IPR2015-00830.

C.D. Partidos et al., "Immunity under the skin: potential application for topical delivery of vaccines", 21 Vaccine 776 (2003), submitted as Exhibit 2041 in Inter Partes Review Case Nos. IPR2015-00643, IPR2015-00644 and IPR2015-00830.

C. Ghose et al., "Transcutaneous immunization with Clostridium difficile toxoid a induces systemic and mucosal immune responses and toxin A-neutralizing antibodies in mice", 75 Infection & Immunity 2326 (2007), submitted as Exhibit 2042 in Inter Partes Review Case Nos. IPR2015-00643, IPR2015-00644 and IPR2015-00830.

G. Glenn et al., "Transcutaneous immunization with cholera toxin protects mice against lethal mucosal toxin challenge", 161(7) J. Immunology 3211 (1998), submitted as Exhibit 2043 in Inter Partes Review Case Nos. IPR2015-00643, IPR2015-00644 and IPR2015-00830.

R. Aharoni et al., "Specific Th2 cells accumulate in the central nervous system of mice protected against experimental autoimmune encephalomyelitis by copolymer 1", vol. 97 No. 21, Proc. Nat'l Acad. Sci. U.S.A., 11472 (2000), submitted as Exhibit 2044 in Inter Partes Review Case Nos. IPR2015-00643, IPR2015-00644 and IPR2015-00830.

R. Arnon et al., "Mechanism of action of glatiramer acetate in multiple sclerosis and its potential for the development of new applications" vol. 101 Supp. 2, Proc. Nat'l Acad. Sci U.S.A., 14593 (2004), submitted as Exhibit 2045 in Inter Partes Review Case Nos. IPR2015-00643, IPR2015-00644 and IPR2015-00830.

H. Varkony et al., "The Glatiramoid Class of Immunomodulator Drugs", 10 Expert Opinion Pharmacotherapy 656 (2009), submitted as Exhibit 2046 in Inter Partes Review Case Nos. IPR2015-00643, IPR2015-00641 and IPR2015-00830.

G. Comi et al., "Glatiramer acetate", 17 Neurologia 244 (2002), submitted as Exhibit 2047 in Inter Partes Review Case Nos. IPR2015-00643, IPR2015-00644 and IPR2015-00830.

Chabot et al., "Cytokine production in T lymphocyte-microglia interaction is attenuated by glatiramer acetate: a mechanism for therapeutic efficacy in multiple sclerosis", 8 Multiple Sclerosis 299 (2002), submitted as Exhibit 2048 in Inter Partes Review Case Nos. IPR2015-00643, IPR2015-00644 and IPR2015-00830.

T. Ziemssen, "Neuroprotection and glatiramer acetate: the possible role in the treatment of multiple sclerosis", 541 Advanced Experimental Med. Biology 111 (2004), submitted as Exhibit 2049 in Inter Partes Review Case Nos. IPR2015-00643, IPR2015-00644 and IPR2015-00830.

Schmeisser et al., "Radioiodination of human interferon-alpha2 interferes with binding of C-terminal specific antibodies." 238 J. Immunological Methods 81 (2000), submitted as Exhibit 2050 in Inter Partes Review Case Nos. IPR2015-00643, IPR2015-00644 and IPR2015-00830.

Efimova et al., "Changes in the secondary structure of proteins labeled with 125I: CD spectroscopy and enzymatic activity studies", 264 J. of Radioanalytical and Nuclear Chemistry, 91- 96 (2005), submitted as Exhibit 2051 in Inter Partes Review Case Nos. IPR2015-00643, IPR2015-00644 and IPR2015-00830.

Toutain P.L. et al., "Plasma terminal half-life", 27 J. Veterinary Pharmacological Therapy 427 (2004), submitted as Exhibit 2052 in Inter Partes Review Case Nos. IPR2015-00643, IPR2015-00644 and IPR2015-00830.

G.B. Ryan et al., Acute inflammation. A review, 86(1) Am. J. Pathology 183 (1977) submitted as Exhibit 2053 in Inter Partes Review Case Nos. IPR2015-00643, IPR2015-00644 and IPR2015-00830.

Shalit et al., "Copolymer-1 (Copaxone®) induces in non-immunologic activation of connective tissue type mast cells", abstract 650, J. Allergy & Clinical Immunology, 345 (1996), submitted as Exhibit 2054 in Inter Partes Review Case Nos. IPR2015-00643, IPR2015-00644 and IPR2015-00830.

Imming et al., "Drugs, their targets and the nature and No. of drug targets", 5 Nature Revs. Drug Discov. 821 (2006), submitted as Exhibit 2055 in Inter Partes Review Case Nos. IPR2015-00643, IPR2015-00644 and IPR2015-00830.

C.B. Pert et al., "Properties of opiate-receptor binding in rat brain", 70 Proc. Natl. Acad. Sci. U.S.A. 2243 (1973), submitted as Exhibit 2056 in Inter Partes Review Case Nos. IPR2015-00643, IPR2015-00644 and IPR2015-00830.

(56) References Cited

OTHER PUBLICATIONS

B. Petty et al., "The effect of systemically administered recombinant human nerve growth factor in healthy human subjects." 36 Annals Neurol. 244 (1994), submitted as Exhibit 2057 in Inter Partes Review Case Nos. IPR2015-00643, IPR2015-00644 and IPR2015-00830.

S.J. Peroutka, "Antimigraine drug interactions with serotonin receptor subtypes in human brain." 23 Annals Neurol. 500 (1988), submitted as Exhibit 2058 in Inter Partes Review Case Nos. IPR2015-00643, IPR2015-00644 and IPR2015-00830.

ALK Hestvik et al., "Multiple sclerosis: glatiramer acetate induces anti-inflammatory T cells in the cerebrospinal fluid", 14 Multiple Sclerosis 749 (2008), submitted as Exhibit 2059 in Inter Partes Review Case Nos. IPR2015-00643, IPR2015-00644 and IPR2015-00830.

R. Aharoni, "The mechanism of action of glatiramer acetate in multiple sclerosis and beyond." 12 Autoimmun Rev. 543 (2013), submitted as Exhibit 2060 in Inter Partes Review Case Nos. IPR2015-00643, IPR2015-00644 and IPR2015-00830.

D. Burger et al., "Glatiramer acetate increases IL-1 receptor antagonist but decreases T cell-induced IL-Ibeta in human monocytes and multiple sclerosis." 106 Proc. Natl. Acad. Sci. U.S.A. 4355 (2009), submitted as Exhibit 2061 in Inter Partes Review Case Nos. IPR2015-00643, IPR2015-00644 and IPR2015-00830.

A. Mendes et al., "Classical immunomodulatory therapy in multiple sclerosis: how it acts, how it works", 69 Arq. Neuropsiquiatr. 536 (2011), submitted as Exhibit 2062 in Inter Partes Review Case Nos. IPR2015-00643, IPR2015-00644 and IPR2015-00830.

R. Aharoni et al., "Copolymer 1 induces T cells of the T helper type 2 that crossreact with myelin basic protein and suppress experimental autoimmune encephalomyelitis." 94 Proc. Natl. Acad. Sci. U.S.A. 10821 (1997), submitted as Exhibit 2063 in Inter Partes Review Case Nos. IPR2015-00643, IPR2015-00644 and IPR2015-00830.

R. Aharoni et al., "Bystander suppression of experimental autoimmune encephalomyelitis by T cell lines and clones of the Th2 type induced by copolymer 1." 91 J. Neuroimmunol. 135 (1998), submitted as Exhibit 2064 in Inter Partes Review Case Nos. IPR2015-00643, IPR2015-00644 and IPR2015-00830.

O. Neuhaus et al., "Mechanisms of action of glatiramer acetate in multiple sclerosis." 56 Neurology 702 (2001), submitted as Exhibit 2065 in Inter Partes Review Case Nos. IPR2015-00643, IPR2015-00644 and IPR2015-00830.

T. Ziemssen et al., "Glatiramer acetate-specific T-helper 1- and 2-type cell lines produce BDNF: implications for multiple sclerosis therapy." 125 Brain 2381 (2002), submitted as Exhibit 2066 in Inter Partes Review Case Nos. IPR2015-00643, IPR2015-00644 and IPR2015-00830.

Miller et al., "Treatment of multiple sclerosis with copolymer-1 (Copaxone): implicating mechanisms of Th1 to Th2/Th3 immune-deviation." 92 J. Neuroimmunol. 113 (1998), submitted as Exhibit 2067 in Inter Partes Review Case Nos. IPR2015-00643, IPR2015-00644 and IPR2015-00830.

Neuhaus et al., "Multiple sclerosis: comparison of copolymer-1-reactive T cell lines from treated and untreated subjects reveals cytokine shift from T helper 1 to T helper 2 cells." 97 Proc. Natl. Acad. Sci. U.S.A. 7452 (2000), submitted as Exhibit 2068 in Inter Partes Review Case Nos. IPR2015-00643, IPR2015-00644 and IPR2015-00830.

Duda et al., "Glatiramer acetate (Copaxone) induces degenerate, Th2-polarized immune responses in patients with multiple sclerosis." 105 J. Clin. Invest. 967 (2000), submitted as Exhibit 2069 in Inter Partes Review Case Nos. IPR2015-00643, IPR2015-00644 and IPR2015-00830.

Hori et al., "Control of regulatory T cell development by the transcription factor Foxp3." 299 Science 1057 (2003), submitted as Exhibit 2070 in Inter Partes Review Case Nos. IPR2015-00643, IPR2015-00644 and IPR2015-00830.

Brunkow et al., "Disruption of a new forkhead/winged-helix protein, scurfin, results in the fatal lymphoproliferative disorder of the scurfy mouse", 27 Nature Genet. 68 (2001), submitted as Exhibit 2071 in Inter Partes Review Case Nos. IPR2015-00643, IPR2015-00644 and IPR2015-00830.

Viglietta et al., Loss of functional suppression by CD1+CD25+ regulatory T cells in patients with multiple sclerosis. 199 J. Exp. Med. 971 (2005), submitted as Exhibit 2072 in Inter Partes Review Case Nos. IPR2015-00643, IPR2015-00644 and IPR2015-00830.

Hong et al., "Induction of CD4+CD25+ regulatory T cells by copolymer-I through activation of transcription factor Foxp3", 102 Proc. Natl. Acad. Sci. U.S. A. 6449 (2005), submitted as Exhibit 2073 in Inter Partes Review Case Nos. IPR2015-00643, IPR2015-00644 and IPR2015-00830.

Wekerle et al., "Cellular immune reactivity within the CNS." Trends Neurosci. 9 TINS 271-277 (1986), submitted as Exhibit 2074 in Inter Partes Review Case Nos. IPR2015-00643, IPR2015-00644 and IPR2015-00830.

W.F. Hickey, "Migration of hematogenous cells through the blood-brain barrier and the initiation of CNS inflammation." 1 Brain Pathol. 97 (1999), submitted as Exhibit 2075 in Inter Partes Review Case Nos. IPR2015-00643, IPR2015-00644 and IPR2015-00830.

Weber et al., "Multiple sclerosis: glatiramer acetate inhibits monocyte reactivity in vitro and in vivo." 127 Brain 1370 (2004), submitted as Exhibit 2076 in Inter Partes Review Case Nos. IPR2015-00643, IPR2015-00644 and IPR2015-00830.

Menge et al., "Disease-modifying agents for multiple sclerosis: recent advances and future prospects", 68 Drugs 2445 (2008), submitted as Exhibit 2077 in Inter Partes Review Case Nos. IPR2015-00643, IPR2015-00644 and IPR2015-00830.

Sodoyez et al., "125I-insulin: kinetics of interaction with its receptors and rate of degradation in vivo." 239 Am. J. Physiol. E3-8. (1980), submitted as Exhibit 2078 in Inter Partes Review Case Nos. IPR2015-00643, IPR2015-00644 and IPR2015-00830.

Wroblewski VJ. "Mechanism of deiodination of 125I-human growth hormone in vivo. Relevance to the study of protein disposition", 42 Biochem. Pharmacol. 889 (1991), submitted as Exhibit 2079 in Inter Partes Review Case Nos. IPR2015-00643, IPR2015-00614 and IPR2015-00830.

Alastair Monro, "The paradoxical lack of interspecies correlation between plasma concentrations and chemical carcinogenicity", 18 Regulatory Toxicology & Pharmacology 115 (1993), submitted as Exhibit 2080 in Inter Partes Review Case Nos. IPR2015-00643, IPR2015-00644 and IPR2015-00830.

Robert T. O'Neill, "Secondary endpoints cannot be validly analyzed if the primary endpoint does not demonstrate clear statistical significance", 18 Controlled Clinical Trials 550 (1997), submitted as Exhibit 2081 in Inter Partes Review Case Nos. IPR2015-00643, IPR2015-00644 and IPR2015-00830.

Karsten Beer et al., "The prevalence of injection-site reactions with disease-modifying therapies and their effect on adherence in patients with multiple sclerosis: an observational study", 11 BMC Neurology 144 (2011), submitted as Exhibit 2082 in Inter Partes Review Case Nos. IPR2015-00643, IPR2015-00644 and IPR2015-00830.

Tjalf Ziemssen et al., "Glatiramer acetate: mechanisms of action in multiple sclerosis", 79 Int'l Rev. Neurobiology 537 (2007), submitted as Exhibit 2083 in Inter Partes Review Case Nos. IPR2015-00643, IPR2015-00644 and IPR2015-00830.

Tjalf Ziemssen, "Modulating processes within the central nervous system is central to therapeutic control of multiple sclerosis", 252 J. Neurology Suppl. 5 V/38-V.45 (2005), submitted as Exhibit 2084 in Inter Partes Review Case Nos. IPR2015-00643, IPR2015-00644 and IPR2015-00830.

Tjalf Ziemssen et al., "Presence of glatiramer acetate-specific TH2 cells in the cerebrospinal fluid of patients with multiple sclerosis 12 months after the start of therapy with glatiramer acetate." 1 J. Neurodegeneration & Regeneration 1 (Sep. 9, 2008), submitted as Exhibit 2085 in Inter Partes Review Case Nos. IPR2015-00643, IPR2015-00644 and IPR2015-00830.

H.P. Rang et. al., "8. Drug Elimination and Pharmacokinetics" in: H.P. Rang et. al., *Pharmacology* (Elsevier 2005, 5th ed., 1987), pp. 106-119, submitted as Exhibit 2086 in Inter Partes Review Case Nos. IPR2015-00643, IPR2015-00644 and IPR2015-00830.

Donald W. Paty, "The Interferon-β1b Clinical Trial and Its Implications for Other Trials", 36 Annals Neurology 5113 (Supp. 1994),

(56) References Cited

OTHER PUBLICATIONS submitted as Exhibit 2087 in Inter Partes Review Case Nos. IPR2015-00643, IPR2015-00644 and IPR2015-00830.
Leonora K. Fisniku, "Gray Matter Atrophy Is Related to Long-Term Disability in Multiple Sclerosis", 64 Annals Neurology 247 (2008), submitted as Exhibit 2088 in Inter Partes Review Case Nos. IPR2015-00643, IPR2015-00644 and IPR2015-00830.
Omar Kahn et al., "Three Times Weekly Glatiramer Acetate in Relapsing-Remitting Multiple Sclerosis", 73 Annals of Neurology 705 (2013), submitted as Exhibit 2089 in Inter Partes Review Case Nos. IPR2015-00643, IPR2015-00644 and IPR2015-00830.
Phillip D. Rumrill Jr., "Multiple sclerosis: Medical and psychosocial aspects, etiology, incidence, and prevalence", 31 J. Vocational Rehabilitation 75 (2009), submitted as Exhibit 2090 in Inter Partes Review Case Nos. IPR2015-00643, IPR2015-00644 and IPR2015-00830.
H.T. Katz et al., "Successful desensitization to glatiramer acetate (Copaxone) in two patients with multiple sclerosis" in: Abstract Book of 2003 Annual Meeting, American College of Allergy, Asthma & Immunology, New Orleans, LA (vol. 92, Jan. 2004), submitted as Exhibit 2091 in Inter Partes Review Case Nos. IPR2015-00643, IPR2015-00644 and IPR2015-00830.
Maria Zellner et al., "Quantitative validation of different protein precipitation methods in proteome analysis of blood platelets", 26 Electrophoresis 2481 (2005), submitted as Exhibit 2092 in Inter Partes Review Case Nos. IPR2015-00643, IPR2015-00644 and IPR2015-00830.
Mariana Castells, "Rapid Desensitization for Hypersensitivity Reactions to Medications", 29 Immunology and Allergy Clinics of North America 585 (2009), submitted as Exhibit 2093 in Inter Partes Review Case Nos. IPR2015-00643, IPR2015-00644 and IPR2015-00830.
Robert Zivadinov et al., Poster titled "MRI Indicators of Brain Tissue Loss: 3-Year Results of the Glatiramer Acetate Low-Frequency Administration (GALA) Open-Label Extension Study in Relapsing-Remitting Multiple Sclerosis", Presented at the American Academy of Neurology 2015 Annual Meeting, Washington, DC (Apr. 18-25, 2015), submitted as Exhibit 2094 in Inter Partes Review Case Nos. IPR2015-00643, IPR2015-00644 and IPR2015-00830.
E. Rubinchik et al., "Responsiveness of human skin mast cells to repeated activation: an in vitro study", 53 Allergy 14 (1998), submitted as Exhibit 2095 in Inter Partes Review Case Nos. IPR2015-00643, IPR2015-00644 and IPR2015-00830.
Daniel Wynn et.al., Poster titled "Patient Experience with Glatiramer Acetate 40mg/1 ml Three-Times Weekly Treatment for Relapsing-Remitting Multiple Sclerosis: Results from the Glacier Extension Study", Presented at The 8th Congress of the Pan-Asian Committee for Treatment and Research in Multiple Sclerosis, Seoul, Republic of Korea (Nov. 19-21, 2015), submitted as Exhibit 2096 in Inter Partes Review Case Nos. IPR2015-00643, IPR2015-00644 and IPR2015-00830.
Avonex® (Inferon beta-1a) IM Injection, published 2008 by Biogen Idec Inc., submitted as Exhibit 2097 in Inter Partes Review Case Nos. IPR2015-00643, IPR2015-00644 and IPR2015-00830.
Rebif Prescribing Information, published 2009 by Pfizer, submitted as Exhibit 2098 in Inter Partes Review Case Nos. IPR2015-00643, IPR2015-00644 and IPR2015-00830.
Extavia Highlights of Prescribing Information, published Aug. 2009 by Novartis, submitted as Exhibit 2099 in Inter Partes Review Case Nos. IPR2015-00643, IPR2015-00644 and IPR2015-00830.
Curriculum Vitae of Edward J. Fox. Md., PhD., FAAN, submitted as Exhibit 2100 in Inter Partes Review Case Nos. IPR2015-00643 and IPR2015-00644 on Nov. 20, 2015 and in IPR2015-00830 on Nov. 25, 2015.
Soelberg Sorensen et al., "Clinical Importance of neutralizing antibodies against interferon beta in patients with rerlapsing-remitting multiple sclerosis", 362 The Lancet 1184 (Oct. 11, 2003), submitted as Exhibit 2101 in Inter Partes Review Case Nos. IPR2015-00643, IPR2015-00644 and IPR2015-00830.
Jan J.M. de Vijlder, "Primary congenital hypothyroidism: defects in iodine pathway", 149 Eur. J. Endocrinology 247 (2003), submitted as Exhibit 2102 in Inter Partes Review Case Nos. IPR2015-00643, IPR2015-00644 and IPR2015-00830.
C.S. Randall, "5. Approaches to the Analysis of Peptides" in: Vincent H. L. Lee ed. *Peptide and Protein Drug Delivery*, New York, Marcel Dekker, Inc. 1991, pp. 203-246, submitted as Exhibit 2103 in Inter Partes Review Case Nos. IPR2015-00643, IPR2015-00644 and IPR2015-00830.
Curriculum Vitae of Dr. Henry George Grabowski, submitted as Exhibit 2104 in Inter Partes Review Case Nos. IPR2015-00643 and IPR2015-00644 on Nov. 20, 2015 and in IPR2015-00830 on Nov. 25, 2015.
List of Testimony of Henry G. Grabowski, submitted as Exhibit 2105 in Inter Partes Review Case Nos. IPR2015-00643 and IPR2015-00644 on Nov. 20, 2015 and in IPR2015-00830 on Nov. 25, 2015.
Documents Relied Upon by Grabowski, submitted as Exhibit 2106 in Inter Partes Review Case Nos. IPR2015-00643 and IPR2015-00644 on Nov. 20, 2015 and in IPR2015-00830 on Nov. 25, 2015.
Table: Approval Timeline, Multiple Sclerosis Drugs, submitted as Exhibit 2107 in Inter Partes Review Case Nos. IPR2015-00643 and IPR2015-00644 on Nov. 20, 2015 and in IPR2015-00830 on Nov. 25, 2015.
Redacted Figure: Copaxone® 40mg/mL Wholesale Dollar Sales (Q1 2014- Q3 2015), submitted as Exhibit 2108 in Inter Partes Review Case Nos. IPR2015-00643 and IPR2015-00644 on Nov. 20, 2015 and in IPR2015-00830 on Nov. 25, 2015.
Redacted Figure: Copaxone® 40mg/mL Extended Units (Q1 2014- Q3 2015), submitted as Exhibit 2109 in Inter Partes Review Case Nos. IPR2015-00643 and IPR2015-00644 on Nov. 20, 2015 and in IPR2015-00830 on Nov. 25, 2015.
Redacted Figure: Copaxone® 40mg/mL Total Prescriptions (Q1 2014- Q3 2015), submitted as Exhibit 2110 in Inter Partes Review Case Nos. IPR2015-00643 and IPR2015-00644 on Nov. 20, 2015 and in IPR2015-00830 on Nov. 25, 2015.
Redacted Figure: Copaxone® 40mg/mL New Prescriptions (Q1 2014- Q3 2015), submitted as Exhibit 2111 in Inter Partes Review Case Nos. IPR2015-00643 and IPR2015-00644 on Nov. 20, 2015 and in IPR2015-00830 on Nov. 25, 2015.
Redacted Figure: Multiple Sclerosis Drugs Share of Wholesale Dollar Sales (Q4 2009- Q3 2015), submitted as Exhibit 2112 in Inter Partes Review Case Nos. IPR2015-00643 and IPR2015-00644 on Nov. 20, 2015 and in IPR2015-00830 on Nov. 25, 2015.
Redacted Figure: Multiple Sclerosis Drugs Share of Total Prescriptions (Q4 2009- Q3 2015), submitted as Exhibit 2113 in Inter Partes Review Case Nos. IPR2015-00643 and IPR2015-00644 on Nov. 20, 2015 and in IPR2015-00830 on Nov. 25, 2015.
Redacted Figure: Multiple Sclerosis Drugs Share of New Prescriptions (Q4 2009- Q3 2015), submitted as Exhibit 2114 in Inter Partes Review Case Nos. IPR2015-00643 and IPR2015-00644 on Nov. 20, 2015 and in IPR2015-00830 on Nov. 25, 2015.
Figure: Rationale for Requesting Copaxone, submitted as Exhibit 2115 in Inter Partes Review Case Nos. IPR2015-00643 and IPR2015-00644 on Nov. 20, 2015 and in IPR2015-00830 on Nov. 25, 2015.
Figure: Perception of 3-times-a-week Copaxone 40mg compared to Daily Copaxone 20mg, submitted as Exhibit 2116 in Inter Partes Review Case Nos. IPR2015-00643 and IPR2015-00644 on Nov. 20, 2015 and in IPR2015-00830 on Nov. 25, 2015.
Figure: Rationale for Discussing 20mg and 40mg for First Line Patients, submitted as Exhibit 2117 in Inter Partes Review Case Nos. IPR2015-00643 and IPR2015-00644 on Nov. 20, 2015 and in IPR2015-00830 on Nov. 25, 2015.
Figure: Perceptions of Copaxone® 40mg compared to Daily Generic GA, submitted as Exhibit 2118 in Inter Partes Review Case Nos. IPR2015-00643 and IPR2015-00644 on Nov. 20, 2015 and in IPR2015-00830 on Nov. 25, 2015.
Figure: Perceptions of Copaxone® 40mg vs. 20mg, submitted as Exhibit 2119 in Inter Partes Review Case Nos. IPR2015-00643 and IPR2015-00644 on Nov. 20, 2015 and in IPR2015-00830 on Nov. 25, 2015.
Redacted Figure: Copaxone® Total Prescriptions (Q4 2009- Q3 2015), submitted as Exhibit 2120 in Inter Partes Review Case Nos. IPR2015-00643 and IPR2015-00644 on Nov. 20, 2015 and in IPR2015-00830 on Nov. 25, 2015.

(56) References Cited

OTHER PUBLICATIONS

Redacted Figure: Copaxone® 20 mg/mL, Copaxone® 40 mg/mL, and GlatopaTM Net Prescriptions Flow (10/26/12-10/9/15), submitted as Exhibit 2121 in Inter Partes Review Case Nos. IPR2015-00643 and IPR2015-00644 on Nov. 20, 2015 and in IPR2015-00830 on Nov. 25, 2015.
Table: Total Promotional Spending to Sales Ratio, submitted as Exhibit 2122 in Inter Partes Review Case Nos. IPR2015-00643 and IPR2015-00644 on Nov. 20, 2015 and in IPR2015-00830 on Nov. 25, 2015.
G. Comi et al., "Early Treatment with glatiramer acetate is efficacious in delaying conversion to clinically definite multiple sclerosis in patients presenting with clinically isolated syndrome and brain lesions detected by MRI", 374 Lancet 1503 (Oct. 31, 2009), submitted as Exhibit 2123 in Inter Partes Review Case Nos. IPR2015-00643, IPR2015-00644 and IPR2015-00830.
R.M. Valenzuela et al., "Clinical response to glatiramer acetate correlates with modulation of IFN-γ and IL-4 expression in multiple sclerosis", 13 Multiple Sclerosis 754 (2007), submitted as Exhibit 2124 in Inter Partes Review Case Nos. IPR2015-00643, IPR2015-00644 and IPR2015-00830.
Y. Blanco et al., "Effect of glatiramer acetate (Copaxone®) on the immunophenotypic and cytokine profile and BDNF production in multiple sclerosis: a longitudinal study", 406 Neuroscience Letters 270 (2006), submitted as Exhibit 2125 in Inter Partes Review Case Nos. IPR2015-00643, IPR2015-00644 and IPR2015-00830.
M. Chen et al., "Sustained immunological effects of Glatiramer acetate in patients with multiple sclerosis treated for over 6 years", 201 J. of Neurological Sciences 71 (2002), submitted as Exhibit 2126 in Inter Partes Review Case Nos. IPR2015-00643, IPR2015-00644 and IPR2015-00830.
Zhao Rong Chen et al., "MU Receptor Binding of Some Commonly Used Opioids and Their Metabolites", 48 Life Sciences 2165 (1991), submitted as Exhibit 2127 in Inter Partes Review Case Nos. IPR2015-00643, IPR2015-00644 and IPR2015-00830.
Alison Palkhivala, "Doubling the Dose of Glatiramer Acetate Does Not Increase Efficacy", Medscape Medical News (Sep. 22, 2008), submitted as Exhibit 2128 in Inter Partes Review Case Nos. IPR2015-00643, IPR2015-00644 and IPR2015-00830.
Curriculum Vitae of Robert William Gristwood PhD, submitted as Exhibit 2130 in Inter Partes Review Case Nos. IPR2015-00643 and IPR2015-00644 on Nov. 20, 2015 and in IPR2015-00830 on Nov. 25, 2015.
Curriculum Vitae of Tjalf Ziemssen, submitted as Exhibit 2131 in Inter Partes Review Case No. IPR2015-00643 and IPR2015-00644 on Nov. 20, 2015 and in IPR2015-00830 on Nov. 25, 2015.
Ziemssen's MS clinical trials, submitted as Exhibit 2132 in Inter Partes Review Case Nos. IPR2015-00643 and IPR2015-00644 on Nov. 20, 2015 and in IPR2015-00830 on Nov. 25, 2015.
Deposition of Stephen J. Peroutka, taken at Washington, D.C., on Oct. 29, 2015, submitted as Exhibit 1066 in Inter Partes Review Case Nos. IPR2015-00643, IPR2015-00644 and IPR2015-00830 on Nov. 18, 2015.
Aug. 25, 2015 Decision on Institution of Inter Partes Review, entered in connection with *Mylan Pharmaceuticals Inc.* v. *Yeda Research & Development Co. Ltd.* for U.S. Pat. No. 8,232,250 in the United States Patent and Trademark Office Patent Trial and Appeal Board (Case No. IPR2015-00643).
Aug. 25, 2015 Decision on Institution of Inter Partes Review, entered in connection with *Mylan Pharmaceuticals Inc.* v. *Yeda Research & Development Co. Ltd.* for U.S. Pat. No. 8,399,413 in the United States Patent and Trademark Office Patent Trial and Appeal Board (Case No. IPR2015-00644).
Sep. 1, 2015 Decision on Institution of Inter Partes Review, entered in connection with *Mylan Pharmaceuticals Inc.* v. *Yeda Research & Development Co. Ltd.* for U.S. Pat. No. 8,969,302 in the United States Patent and Trademark Office Patent Trial and Appeal Board (Case No. IPR2015-00830).

Oliver Neuhaus, et al., Pharmacokinetics and pharmacodynamics of the interferon-bets, glatiramer acetate, and mitoxantrone in multiple sclerosis, 259 J. Neurol. Sci., 2007.
O. Khan, et al., Randomized, prospective, rater-blinded, four-year, pilot study to compare the effect of daily versus every-other-day [GA] 20 mg subcutaneous injections in relapsing-remitting multiple sclerosis, S295 Multiple Sclerosis, 902 (2008).
S. Fletcher et al., Copolymer 1 (Glatiramer Acetate) in Relapsing Forms of Multiple Sclerosis: Open Multicenter Study of Alternate-Day Administration, 25(1) Clin. Neuropharmacology, 11-15 (2002).
Teva Provides Upate on FORTE Trial (Jul. 7, 2008).
J.A. Cohen et al., Randomized, double-blind, dose-comparison study of glatiramer acetate in relapsing-remitting MS, 68:12 Neurology, 939-44 (2007).
Teva Press Release, *Phase III Data Published in Annals of Neurology Show That a Higher Concentration Dose of Glatiramer Acetate Given Three Times a Week Reduced Annualized Relapse Rates in the Treatment of Relapsing-Remitting Multiple Sclerosis* dated Jul. 1, 2013.
Omar Khan et al., *Three Times Weekly Glatiramer Acetate in Relapsing-Remitting Multiple Sclerosis*, 73 Ann. Neurol., 705-13 (2013).
Kate McKeage, *Glatiramer Acetate 40 mg/mL in Relapsing-Remitting Multiple Sclerosis: A Revies*, CNS Drugs (Apr. 24, 2015).
Feb. 16, 2016 Petition for Post Grant Review of U.S. Pat. No. 9,155,776 in the United States Patent and Trademark Office Patent Trial and Appeal Board (Case No. PGR2016-00010).
Expert Declaration of Ari Green, M.D. in Support of Petition for Post-Grant Review of U.S. Pat. No. 9,155,776, dated Feb. 7, 2016, submitted as Exhibit 1003 in Post Grant Review Case No. PGR2016-00010.
A Study in Subjects with Relapsing-Remitting Multiple Sclerosis (RRMS) to Assess the Efficacy, Safety and Tolerability of Glatiramer Acetate (GA) Injection 40 mg Administered Three Times a Week Compared to Placebo (GALA), NCT01067521 [online]. ClinicalTrials.gov [retrieved on Feb. 5, 2016]. Retrieved from the Internet: <URL:clinicaltrials.gov/ct2/show/NCT01067521>, submitted as Exhibit 1004 in Post Grant Review Case No. PGR2016-00010.
Safety and Tolerability of Glatiramer Acetate (GLACIER), NCT01874145 [online]. ClinicalTrials.gov [retrieved on Feb. 5, 2016]. Retrieved from the Internet: <URL:clinicaltrials.gov/ct2/show/NCT01874145, submitted as Exhibit 1005 in Post Grant Review Case No. PGR2016-00010.
Plaintiffs' Supplemental Opening Claim Construction Brief, In re Copaxone 40 mg Consolidated Cases, No. 1:14-cv-01171-GMS (D.Del), dated Dec. 18, 2015, submitted as Exhibit 1006 in Post Grant Review Case No. PGR2016-00010.
Citizen Petition Requesting That FDA Refrain from Approving any Abbreviated New Drug Application Referencing Copaxone® (glatiramer acetate injection) Until Certain Conditions Are Met, dated Jul. 2, 2014, filed with U.S. Food and Drug Administration, submitted as Exhibit 1009 in Post Grant Review Case No. PGR2016-00010.
Citizen Petition Requesting That FDA Consider New Scientific Information and Refrain from Approving Any Abbreviated New Drug Information and Refrain from Approving Any Abbreviated New Drug Application Referencing Copaxone ® (glatiramer acetate injection) Until Certain Conditions Are Met, dated Mar. 31, 2015, filed with U.S. Food and Drug Administration, submitted as Exhibit 1010 in Post Grant Review Case No. PGR2016-00010.
Kate McKeage, "Glatiramer Acetate 40 mg/mL in Relapsing-Remitting Multiple Sclerosis: A Review", CNS Drugs, Apr. 24, 2015, submitted as Exhibit 1011 in Post Grant Review Case No. PGR2016-00010.
Copaxone®, Food and Drug Administration Approved Labeling, Jan. 2014, submitted as Exhibit 1012 in Post Grant Review Case No. PGR2016-00010.
Defendant's Opening Claim Construction Brief Regarding U.S. Pat. No. 9,155,776, dated Dec. 18, 2015, in re Copaxone 40 mg Consolidated Cases, No. 1:14-cv-01171-GMS (D.Del.), submitted as Exhibit 1013 in Post Grant Review Case No. PGR2016-00010.

(56) References Cited

OTHER PUBLICATIONS

Plaintiff's Opening Claim Construction Brief, dated Sep. 11, 2015, in re Copaxone 40 mg Consolidated Cases, No. 1:14-cv-01171-GMS (D.Del.), submitted as Exhibit 1014 in Post Grant Review Case No. PGR2016-00010.
Yeda's Preliminary Patent Owner Response, dated May 26, 2015, for Case No. IPR2015-00643, submitted as Exhibit 1015 in Post Grant Review Case No. PGR2016-00010.
Deposition of Tjalf Ziemssen, dated Feb. 2, 2016, submitted as Exhibit 1016 in Post Grant Review Case No. PGR2016-00010.
Giancarlo Comi, et al., Phase III Dose-Comparison Study of Glatiramer Acetate for Multiple Sclerosis, Ann. Neurol. 2011; 69:75-82 (2011), submitted as Exhibit 1017 in Post Grant Review Case No. PGR2016-00010.
Teva Announces Top-line Results from GALA Phase III Trial Evaluating a New Dosage for Glatiramer Acetate Given Three Times Weekly for Relapsing-Remitting Multiple Sclerosis, [online]. [retrieved on Feb. 5, 2016]. Retrieved from the Internet: <URL:www.tevapharm.com/news/teva_announces_top_line_results_from_gala_phase_iii_trial_evaluating_a_new_dosage_for_glatiramer_acetate_given_three_times_weekly_for_relapsing_remitting_multipie_sclerosis_06_12.aspx>, submitted as Exhibit 1018 in Post Grant Review Case No. PGR2016-00010.
Wolinsky et al. "Reduced frequency severity of injection site reactions with glatiramer acetate 40mg/mL three times weekly dosing" presented at the Jount Americas Committee for Treatment and Reseasrch in Multiple Sclerosis (ACTRIMS) European Committee for Treatment of Research in Multiple Sclerosis (ECTRIMS), Boston, MA, Sep. 10-13, 2014, poster, submitted as Exhibit 1019 in Post Grant Review Case No. PGR2016-00010.
Deposition of Edward J. Fox, M.D., dated Jan. 26, 2016, submitted as Exhibit 1020 in Post Grant Review Case No. PGR2016-00010.
Stipulation, in re Copaxone 40 mg Consolidated Cases, No. 1:14-cv-01171-GMS (D. Del.) (ECF No. 190), dated Feb. 10, 2016, submitted as Exhibit 1021 in Post Grant Review Case No. PGR2016-00010.
Plaintiffs' Opening Claim Construction Brief, In re Copaxone 40 mg Consolidated Cases, No. 1:14-cv-01171-GMS (D. Del.) (ECF No. 91), dated Sep. 11, 2015, submitted as Exhibit 1023 in Post Grant Review Case No. PGR2016-00010.
Yeda's Patent Owner Response, dated Nov. 20, 2015, for IPR2015-00643, submitted as Exhibit 1024 in Post Grant Review Case No. PGR2016-00010.
Yeda's Patent Owner Response, dated Nov. 20, 2015, for IPR2015-00644, submitted as Exhibit 1025 in Post Grant Review Case No. PGR2016-00010.
Yeda's Patent Owner Response, dated Nov. 25, 2015, for IPR2015-00830, submitted as Exhibit 1026 in Post Grant Review Case No. PGR2016-00010.
Miller, The Importance of Early Diagnosis of Multiple Sclerosis, J.Managed Care Pharmacy 10:S4-S11 (Jun. 2004), submitted as Exhibit 1027 in Post Grant Review Case No. PGR2016-00010.
Thomas M. Stewart, Injectable Multiple Sclerosis Medications: A Patient Survey of Factors Associated with Injection-Site Reactions, 14 Int'l J. MS Care 46, 48 (2012), submitted as Exhibit 1028 in Post Grant Review Case No. PGR2016-00010.
Pelidou et al., Multiple sclerosis presented as clinically isolated syndrome: the need for early diagnosis and treatment, Ther. Clin. Risk Management 4:627-30 (Jun. 2008), submitted as Exhibit 1029 in Post Grant Review Case No. PGR2016-00010.
Lynn McEwan et al., Best Practices in Skin Care for the Multiple Sclerosis Patient Receiving Injectable Therapies, 12 Int'l J. MS Care 177, 187 (2010), submitted as Exhibit 1030 in Post Grant Review Case No. PGR2016-00010.
Barry Singer et al., Comparative Injection-site Pain and Tolerability of Subcutaneous Serum-free Formulation of Interferonβ-1a Versus Subcutaneous interferonβ-1b: Results of the Randomized, Multicenter, Phase IIIb Reforms Study, 12 BMC Neurology, Dec. 2012, submitted as Exhibit 1031 in Post Grant Review Case No. PGR2016-00010.

U.S. Department of Health and Human Services, Common Terminology Criteria for Adverse Events (CTCAE) Version 4.0, published May 28, 2009, submitted as Exhibit 1032 in Post Grant Review Case No. PGR2016-00010.
Frohman, Multiple Sclerosis—The Plaque and its Pathogenesis, New England J.Med. 354:942-55 (2006), submitted as Exhibit 1033 in Post Grant Review Case No. PGR2016-00010.
Haines et al., Linkage of the MHC to familial multiple sclerosis suggests genetic heterogeneity. The multiple sclerosis genetics group, HUM.MOL. GENET. 7:1229-34 (1998), submitted as Exhibit 1034 in Post Grant Review Case No. PGR2016-00010.
Comi et al., European/Canadian multicenter, double-blind, randomized, placebo-controlled study of the effects of glatiramer acetate on magnetic resonance imaging measured disease activity and burden in patients with relapsing multiple sclerosis, Annals Neurol. 49:290-297 (2001) submitted as Exhibit 1035 in Post Grant Review Case No. PGR2016-00010.
Ge et al., Glatiramer acetate (Copaxone) treatment in relapsing-remitting MS, Quantitative MR assessment, Neurol. 54:813-17 (Feb. 2000), submitted as Exhibit 1036 in Post Grant Review Case No. PGR2016-00010.
Soares et al., Localized panniculitis secondary to subcutaneous glatiramer acetate injections for the treatment of multiple sclerosis: a clinicopathologic and immunohistochemical study, J. Am. Acad. Derm. 55:968-74 (2006), submitted as Exhibit 1037 in Post Grant Review Case No. PGR2016-00010.
Jerry S. Wolinsky et al., GLACIER: An Open-Label, Randomized, Multicenter Study to Assess the Safety and Tolerability of Glatiramer Acetate 40 MG Three-Times Weekly Versus 20 MG Daily in Patients with Relapsing-Remitting Multiple Sclerosis, 4 Multiple Sclerosis & Related Disorders 370, 371 (2015), submitted as Exhibit 1038 in Post Grant Review Case No. PGR2016-00010.
Rich et al., Stepped-care approach to treating MS: A managed care treatment algorithm, J.Managed Care Pharm. 10(3) (Suppl. S-b):S26-S32 (Jun. 2004), submitted as Exhibit 1039 in Post Grant Review Case No. PGR2016-00010.
Bakshi et al., Imaging of multiple sclerosis: Role in neurotherapeutics, J. Am. Soc. Exper. Neurotherapeutics 2:277-303 (Apr. 2005), submitted as Exhibit 1040 in Post Grant Review Case No. PGR2016-00010.
Stuart, Clinical management of multiple sclerosis: The treatment paradigm and issues of patient management, J. Managed Care Pharmacy 10(3)(Suppl. S-b):S19-S25 (Jun. 2004), submitted as Exhibit 1041 in Post Grant Review Case No. PGR2016-00010.
Edgar et al., Lipoatrophy in patients with multiple sclerosis on glatiramer acetate, Canadian J. Neurol. Sci. 31:58-63 (2004), submitted as Exhibit 1042 in Post Grant Review Case No. PGR2016-00010.
Johnson et al., Copolymer 1 reduces relapse rate and improves disability in relapsing-remitting multiple sclerosis, Neurology 45:1268-76 (1995), submitted as Exhibit 1043 in Post Grant Review Case No. PGR2016-00010.
Betaseron® Product Label (Oct. 2003), Berlex Laboratories, submitted as Exhibit 1044 in Post Grant Review Case No. PGR2016-00010.
Rebif® (interferon beta-1a) Product Label, Jun. 2015, Pfizer Inc., submitted as Exhibit 1045 in Post Grant Review Case No. PGR2016-00010.
Avonex® (Interferon beta-1a) Product Label, Feb. 2007, Biogen Idec Inc., submitted as Exhibit 1046 in Post Grant Review Case No. PGR2016-00010.
Interferon Beta 1b (Extavia®), Abbreviated National Drug Monograph, published Sep. 2010 by VA Pharmacy Benefits Management Services, Medical Advisory Panel and VISB Pharmacist Executives, submitted as Exhibit 1047 in Post Grant Review Case No. PGR2016-00010.
Tysabri® Product Label (Oct. 2008), Biogen Idec Inc., submitted as Exhibit 1048 in Post Grant Review Case No. PGR2016-00010.
U.S. Pat. No. 3,849,550, submitted as Exhibit 1007 in Post Grant Review Case No. PGR2016-00010 issue date: Nov. 19, 1974.
File wrapper of NDA 20-622, cited as D34 in opposition procedure against EP2405749 [online]. European Patent Register, submitted Nov. 9, 2015 [retrieved on Dec. 16, 2015]. Retrieved from the

(56) References Cited

OTHER PUBLICATIONS

Internet: <URL://register.ep.org/application?documentId=EX8Q9F3Q8243DSU&number=EP10810282&lng=en&npl=true>. Mar. 9; 2015 Mylan's Reply to Yeda's Patent Owner Response filed in connection with *Mylan Pharmaceuticals Inc.* v. *Yeda Research & Development Co. Ltd*, for U.S. Pat. No. 8,232,250 in the United States Patent and Trademark Office Patent Trial and Appeal Board (Case No. IPR2015-00643).

Mar. 9, 2015 Mylan's Reply to Yeda's Patent Owner Response filed in connection with *Mylan Pharmaceuticals Inc.* v. *Yeda Research & Development Co. Ltd*, for U.S. Pat. No. 8,399,413 in the United States Patent and Trademark Office Patent Trial and Appeal Board (Case No. IPR2015-00644).

Mar. 9, 2015 Mylan's Reply to Yeda's Patent Owner Response filed in connection with *Mylan Pharmaceuticals Inc.* v. *Yeda Research & Development Co. Ltd.* for U.S. Patent No, 3,969,302 in the United States Patent and Trademark Office Patent Trial and Appeal Board (Case No. IPR2015-00830).

Expert Declaration of Ari Green, M.D. in Support of Petitioner's Reply to Patent Owner's Response, dated Mar. 9, 2016, submitted as Exhibit 1085 on Mar. 8, 2016 in Inter Partes Review Case Nos. IPR2015-00643, IPR2015-00644 and IPR2015-00830.

Declaration of Prof. Joel W. Hay (public version), dated Mar. 9, 2016, submitted as Exhibit 1099 on Mar. 22, 2016 in Inter Partes Review Case Nos. IPR2015-00643, IPR2015-00644 and IPR2015-00830.

Deposition Transcript of Joel W. Hay, Ph.D., which deposition took place on Apr. 4, 2016, submitted as Exhibit 1141 on Apr. 12, 2016 in Inter Partes Review Case Nos. IPR2015-00643, IPR2015-00644 and IPR2015-00830.

Deposition Transcript of an Green, M.D., which deposition took place on Apr. 4, 2016, submitted as Exhibit 1142 on Apr. 12, 2016 in Inter Partes Review Case Nos. IPR2015-00643; IPR2015-00644 and IPR2015-00830.

Deposition Transcript of Dr. Jerry S. Wolinsky (public version) taken in In re Copaxone 40 mg Consolidated Cases, No. 14-1171 (D. Del), which deposition took place on Feb. 15, 2016, submitted as Exhibit 1140 on Apr. 12, 2016 in Inter Partes Review Case Nos. IPR2015-00643, IPR2015-00644 and IPR2015-00830.

Deposition Transcript of Robert W. Gristwood, Ph.D., which deposition took place on Jan. 13, 2016, submitted as Exhibit 2145 on Mar. 1, 2016 in Inter Partes Review Case Nos. IPR2015-00643, IPR2015-00644 and IPR2015-00830.

Deposition Transcript of Edward J. Fox, M.D., which deposition took place on Jan. 26, 2016, submitted as Exhibit 2146 on Mar. 1, 2016 in Inter Partes Review Case Nos. IPR2015-00643, IPR2015-00644 and IPR2015-00830.

Deposition Transcript of Tjalf Ziemssen, which deposition took place on Feb. 2, 2016, submitted as Exhibit 2147 on Mar. 1, 2016 in Inter Partes Review Case Nos. IPR2015-00643, IPR2015-00644 and IPR2015-00830.

Deposition Transcript of Henry G. Grabowski, Ph. D., which deposition took place on Feb. 10, 2016, submitted as Exhibit 2148 on Mar. 7, 2016 in Inter Partes Review Case Nos. IPR2015-00643, IPR2015-00644 and IPR2016-00830.

O. Khan, et al., Glatiramer acetate 20mg subcutaneous twice-weekly versus daily injections: results of a pilot, prospective, randomised, and rater-blinded clinical and MRI 2-year study in relapsing-remitting multiple sclerosis, Multiple Sclerosis 2009; 15:S151-S269, S249-S250 (2009), submitted as Exhibit 1068 on Mar. 8, 2016 in Inter Partes Review Case Nos. IPR2015-00643, IPR2015-00644 and IPR2015-00830.

G. Pardo, et al., Impact of an oral antihistamine on local injection site reactions with glatiramer acetate, Multiple Sclerosis, 2007; 13:S7-S2753, S134 (2007), submitted as Exhibit 1069 on Mar. 8, 2016 in Inter Partes Review Cases Nos. IPR2015-00643, IPR2015-00644 and IPR2015-00830.

S. Rains, et al., Glatiramer acetate: successful desensitazation for treatment of multiple sclerosis, Annals of Allergy, Asthma & Immunology, 2010;104:321-325, submitted as Exhibit 1070 on Mar. 8, 2016 in Inter Partes Review Case Nos. IPR2015-00643, IPR2015-00644 and IPR2015-00830.

E. Fisher, et al., Gray Matter Atrophy in Multiple Sclerosis: A Longitudinal Study, Annals of Neurology, 2008;64:255-265, submitted as Exhibit 1071 on Mar. 8, 2016 in Inter Partes Review Case Nos. IPR2015-00643, IPR2015-00644 and IPR2018-00830.

Fourth Declaration of Edward J. Fox, M.D., Ph.D., In re Copaxone 40 mg Consolidated Cases, Civil Action No. 1:14-cv-001171, ECF No. 158 (D. Del.) dated. Jan. 8, 2016 together with Exhibits A-C, submitted as Exhibit 1072 on Mar. 8, 2016 in Inter Partes Review Case Nos. IPR2015-00643, IPR2015-00644 and IPR2015-00830.

G. Anderson, et al., Tolerability and safety of novel half milliliter formulate of glatiramer acetate for subcutaneous injection: An open-label, multicenter, randomized comparative study, Journal of Neurology (2010) 257:1917-1923, submitted as Exhibit 1073 on Mar. 8, 2016 in Inter Partes Review Case Nos. IPR2015-00643, IPR2015-00644 and IPR2015-00830.

G. Shaw, Exorbitant Drug Costs May Price. Out Patients, The Washington Diplomat (Apr. 27, 2011) submitted as Exhibit 1074 on Mar. 8, 2016 in Inter Partes Review Case Nos. IPR2015-00643, IPR2015-00644 and IPR2015-00830.

T. Ziemssen, et al., A 2-year observational study of patients with relapsing-remitting multiple sclerosis converting to glatiramer acetate from other disease--modifying therapies: the Coptimize trial, Journal of Neurology (2014) 261:2101-2111, submitted as Exhibit 1079 on Mar. 8, 2016 in Inter Partes Review Case Nos. IPR2015-00643, IPR2015-00644 and IPR2015-00830.

T. Ziemssen, et al., Sub-analysis of geographical variations in the 2-year observational Coptimize trial of patients with relapsing-remitting-multiple sclerosis converting to glatiramer acetate, BMC Neurology (2015) 15:189, submitted as Exhibit 1080 on Mar. 8, 2016 in Inter Partes Review Case Nos. IPR2015-00643, IPR2015-00644 and IPR2015-00830.

T. Ziemssen, et al., QualiCOP: An Open-Label, Prospective, Observational Study of Glatiramer Acetate in Patients with Relapsing-Remitting Multiple Sclerosis, submitted as Exhibit 1081 on Mar. 8, 2016 in Inter Partes Review Case Nos. IPR2015-00643, IPR2015-00044 and IPR2015-00830.

N. Kleiner, et al., Immunological Response to Glatiramer Acetate in MS Patients after Different Pretreatments—The CopImmunoNet Study, P06.178, A554 Neurology 74, Suppl 2 (Mar. 2, 2010), submitted as Exhibit 1082 on Mar. 8, 2016 in Inter Partes Review Case Nos. IPR2015-00643, IPR2015-00644 and IPR2015-00830.

Teva News Release, New Study Demonstrated Significant Reduction in Annualized Relapse Rate and Halting of Disability Progression in MS Patients Switching to Copaxone® (Apr. 14, 2011), submitted as Exhibit 1083 on Mar. 8, 2016 in Inter Partes Review Case Nos. IPR2015-00643, IPR2015-00644 and IPR2015-00830.

R. Aharoni, et al., Glatiramer acetate-specific T cells in the brain express T helper 2/3 cytokines and brain-derived neurotrophic factor in situ, PNAS 100(24):14157-14102 (Nov. 25, 2003), submitted as Exhibit 1084 on Mar. 8, 2016 in Inter Partes Review Case Nos. IPR2015-00643, IPR2015-00644 and IPR2015-00830.

Teva's Shared Solutions® How to Prepare for Your Injection, "Preparation" [online]. Teva Neuroscience [retrieved on Mar. 7, 2016]. Retrieved from the internet: <URL://www.copaxone.com/injection-assistance/preparing-your-injection.html>, submitted as Exhibit 1086 on Mar. 9, 2016 in Inter Partes Review Case Nos. IPR2015-00643, IPR2015-00644 and IPR2015-00830.

Louise Gagnon, "Every-Other-Day Dosing of Glatiramer Acetate Reduces Adverse Reactions with Comparable Efficacy to Daily Dosing: Presented at WCTRMS" [online]. PeerView Press, Sep. 21, 2008 [retrieved on Mar. 8, 2016]. Retrieved from the internet: <URL://peerviewpress.com/every-other-day-dosing-flatiramer-acetate-reduces-adverse-reactions-comparable-efficacy-daily-dosing-presented-wctrms>, submitted as Exhibit 1087 on Mar. 9, 2016 in Inter Partes Review Case Nos. IPR2015-00643, IPR2015-00644 and IPR2015-00830.

J. Wolinsky, Glatiramer acetate for the treatment of multiple sclerosis, Expert Opinion on Pharmacotherapy, 5(4):875-891 (2004), submitted as Exhibit 1088 on Mar. 9, 2016 in Inter Partes Review Case Nos. IPR2015-00643, IPR2015-00644 and IPR2015-00830.

(56) References Cited

OTHER PUBLICATIONS

O. Khan et al., Glatiramer acetate 20mg subcutaneous twice-weekly versus daily injections: results of a pilot, prospective, randomised, and rater-blinded clinical and MRI 2-year study in relapsing-remitting multiple sclerosis, Multiple Sclerosis, 15(S151-S269 (2009), submitted as Exhibit 1089 on Mar. 9, 2016 in Inter Partes Review Case Nos. IPR2015-00643, IPR2015-00644 and IPR2015-00830.
M.S. Weber et al. , Mechanism of Action of Glatiramer Acetate in Treatment of Multiple Sclerosis, Neurotherapeutics, 4(4):647-653 (2007), submitted as Exhibit 1090 on Mar. 9, 2016 in Inter Partes Review Case Nos. IPR2015-00643, IPR2015-00644 and IPR2015-00830.
W. F. Hickey et al. , T-Lymphocyte Entry Into the Central Nervous. System, J. of Neuroscience Research, 28(2):254-260 (1991), submitted as Exhibit 1091 on Mar. 9, 2016 in Inter Partes Review Case Nos. IPR2015-00643, IPR2015-00644 and IPR2015-00830.
T.M. Stewart et al., Injectable Multiple Sclerosis medications: A Patient Survey of Factors Associated with injection-Site Reactions, Int'l J. MS Care, 14(1):46-53 (2012), submitted as Exhibit 1092 on Mar. 9, 2016 in Inter Partes Review-Case Nos. IPR2015-00643, IPR2015-00644 and IPR2015-00830.
U.S. Dep't Health & Human Services., Common Terminology Criteria for Adverse Events (CTCAE) (Version 4.03 Jun. 14, 2010), published May 28, 2009, submitted as Exhibit 1093 on Mar. 9, 2016 in Inter Partes Review Case Nos. IPR2015-00643, IPR2015-00644 and IPR2015-00830.
B. Singer et al., Comparative injection-site pain and tolerability of subcutaneous serum-free formulation of interferonβ-1a verus subcutaneous interferonβ-1b: results of the randomized, multicenter, Phase IIIb REFORMS study, BMC Neurology, 12:154 (2012), submitted as Exhibit 1094 on Mar. 9, 2016 in Inter Partes Review Case Nos. IPR2015-00643, IPR2015-00644 and IPR2015-00830.
L. McEwan et al., Best Practices in Skin Care for the Multiple Sclerosis Patient Receiving Injectable Therapies, Int'l J. MS Care, 12:177-189 (2010), submitted as Exhibit 1095 on Mar. 9, 2016 in Inter Partes Review Case Nos. IPR2015-00643, IPR2015-00644, IPR2015-00830.
R. Bermel et al., The measurement and clinical relevance of brain atrophy in multiple sclerosis, Lancer Neurol., 5(2):158-70 (2006), submitted as Exhibit 1096 on Mar. 9, 2016 in Inter Partes Review Cases Nos. IPR2015-00643, IPR2015-00644 and IPR2015-00830.
E. Fisher et al., Gray Matter Atrophy in Multiple Sclerosis: A Longitudinal Study, Ann. Neurol., 4:255-265 (2008), submitted as Exhibit 1097 on Mar. 9, 2016 in Inter Partes Review Case Nos. IPR2015-00643, IPR2015-00644 and IPR2015-00830.
Lauren LeBano, Gray Matter Atrophy May Serve as an Effective Outcome measure for MS Clinical Trials [online] Neurol. Reviews, 20(2):8 (2012) [retrieved on Mar. 8, 2016]. Retrieved from the internet: <URL://www.neurologyreviews.com/specialty-focus/multiple-sclerosis-ms/article/gray-matter-atrophy-mayserve-as-an-effective-outcome-measure-for-ms-clinical-trials/5f1c2ba2adde725b8a583502b5c332e1.html?trendmd-shared=1>, submitted as Exhibit 1098 on Mar. 9, 2016 in Inter Partes Review Case Nos. IPR2015-00643, IPR2015-00644 and IPR2015-00830.
Xinke Zhang et al., Cost Effectivesness of Fingolimod, Teriflunomide, Dimethyl Fumarate and Intramuscular Interferon-β1a in Relapsing-Remitting Multiple Sclerosis 29(1) CNS Dugs 71 (2015), submitted as Exhibit 1100 on Mar. 9, 2016 in Inter Partes Review Case Nos. IPR2015-00643, IPR2015-00644 and IPR2015-00830.
Carly Helfand, Why is Novartis' Copaxone copy lagging? It'all about coverage, analyst explains[online]Fierce Pharma Sep. 11, 2015, [retrieved on Dec. 28, 2015]. Retrieved from the internet: <URL://www.fiercepharma.com/story/why-novartis-copaxone-copy-lagging-its-all-about-coverage-analyst-explains/2015-09-11>, submitted as Exhibit 1105 on Mar. 9, 2016 in Inter Partes Review Case Nos. IPR2015-00643, IPR2015-00644 and IPR2015-00830.
Biogen Press Release, Biogen 2015 Revenues Increase 11% to $10.8 Billion [online] BioGen.com, Jan. 27, 2016, Retrieved from the internet: <URL://media.biogen.com/press-release/investor-relations/biogen-2015-revenues-increase-11-108-billion>, submitted as Exhibit 1107 on Mar. 9, 2016 in Inter Partes Review Case Nos. IPR2015-00643, IPR2015-00644 and IPR2015-00830.
A to Z of MS Alemtuzumab (Lemtrada), Multiple Sclerosis Trust—information, education, research and support [online] Multiple Sclerosis Trust, Dec. 16, 2014 [retrieved on Jun. 2, 2015]. Retrieved from the Internet: URL://www.mstrust.org.uk/atoz/alemtuzumab-lemtrada.jsp>, submitted as Exhibit 1108 on Mar. 9, 2016 in Inter Partes Review Case Nos. IPR2015-00643, IPR2015-00644 and IPR2015-00830.
R. Osborne, Buzz around Campath proof-of-concept trial, in MS, 27(1) Nature Biotechnology 6 (2009), submitted as Exhibit 1109 on Mar. 9, 2016 in Inter Partes Review Case Nos. IPR2015-00643, IPR2015-00644 and IPR2015- 00830.
J. A. Cohen et al., Alemtuzumab versus interferon beta la as first-line treatment for patients with relapsing-remitting multiple sclerosis: a randomized controlled phase 3 trial, 380 LANCET, 3801519 (2012), submitted as Exhibit 1110 on Mar. 9, 2016 in Inter Partes Review Case Nos. IPR2015-00643, IPR2015-00644 and IPR2015-00830.
IMS Institute for Health Informatics, Medicine Use and Shifting Costs of Healthcare, Chart Notes, Apr. 2014, submitted as Exhibit 1111 on Mar. 9, 2015 in Inter Partes Review Case Nos. IPR2015-00543, IPR2015-00644 and IPR2015-00830.
IMS institute for Health Informatics, Declining Medicine Use and Costs: For Better or Worse, May 2013, submitted as Exhibit 1112 on Mar. 9, 2016 in Inter Partes Review Case Nos. IPR2015-00643, IPR2015-00644 and IPR2015-00830.
Valeant Pharms. Int'l, Inc., Transcript of Jun. 17, 2014 Investor Presentation [online] SEC.gov [retrieved on May 26, 2015]. Retrieved from the internet: URL://www.sec.gov/Archives/edgar/data/850693/000119312614239987/d745316d425.htm>, submitted as Exhibit 1113 on Mar. 9, 2016 in Inter Partes Review Case Nos. IPR2015-00643, IPR2015-00644 and IPR2015-00830.
Brian Orelli, Momenta Slowed (Temporarily) [online] The Motley Fool, Nov. 7, 2015 [retrieved on Dec. 28, 2015]. Retrieved from the Internet: <URL://www.fool.com/investing/general/2015/11/07/momenta-slowed- temporarily.aspx>, submitted as Exhibit 1114 on Mar. 9, 2016 in Inter Partes Review Case Nos. IPR2015-00643, IRR2013-00644 and IPR2015-00830.
Carly Helfand, The top 10 best-selling multiple sclerosis drugs of 2013 [online]. FiercePharma, Sep. 9, 2014 [retrieved on May 27, 2015]. Retrieved from the internet:<URL://www.fiercepharma.com/special-reports/top-10-best-selling-multiple-sclerosis-drugs-2013, submitted as Exhibit 1115 on Mar. 9, 2016 in Inter Partes Review Case Nos. IPR2015-00643, IPR2015-00644 and IPR2015-00830.
Tracy Staten, Sanofi tags newly OK'd MS drug Lemtrada at $158K, ready to tout head-to-head Rebif data [online], FiercePharmamarketing, Nov. 17, 2014. [retrieved on May 27, 2015]. Retrieved from the internet: <URL://www.fiercepharmamarketing.com/node/2101/print>, submitted as Exhibit 1116 on Mar. 9, 2016 in Inter Partes Review Case Nos, IPR2015-00643, IPR2015-00644 and IP2015-00830.
Kim Frick et al., Serono to sell Amgen multiple sclerosis drug [Novantrone] in U.S. [online], Firstword Pharma, Nov. 13, 2002 [retrieved on May 27, 2015]. Retrieved from the internet: <URL://www.firstwordpharma.com/print/212958?tsid=17>, submitted as Exhibit 1117 on Mar. 9, 2016 in Inter Partes Review Case Nos. IPR2015-00643, IPR2015-00644 and IPR2015-00830.
Christopher Luzzio & B. Mark Keegan, Multiple Sclerosis Medication [online]; Medscape Reference, Nov. 24, 2014 [retrieved on May 28, 2015]. Retrieved from the internet: <URL://emedicine.medscape.com/article/1146199-medication#1>, submitted as Exhibit 1118 on Mar. 9, 2016 in Inter Partes Review Case Nos. IPR2015-00643, IPR2015-00644 and IPR2015-00830.
IMS Health, U.S. Pharmaceutical Market: Trends Issues & Outlook, Sep. 15, 2013, submitted as Exhibit 1120 on Mar. 9, 2016 in Inter Partes Review Case Nos. IPR2015-00643, IPR2015-00644 and IPR2015-00830.
Jesse David & Marion B. Stewart, Commercial Success: Economic Principles Applied to Patent Litigation, in Economic Damages in Intellectual Property: A Hands-On Guide to Litigation 159-170, Daniel Slottje ed., John Wiley & Sons, Inc. 2006, submitted as

(56) References Cited

OTHER PUBLICATIONS

Exhibit 1121 on Mar. 9, 2016 in inter Partes Review Case Nos. IPR2015-00643, IPR2015-00644 and IPR2015-00830.
Angela Maas, New Copaxone Formulation. Could Help Teva Retain Market Share [online], AIS Health, Feb. 19, 2014 [retrieved on Dec. 31, 2015]. Retrieved from the internet: <URL://aishealth.com/blog/pharmacy-benefit-management/new-copaxone-formulation-could-help-teva-retain-market-share>, submitted as Exhibit 1122 on Mar. 9, 2016 in Inter Partes Review Case Nos. IPR2015-00643, IPR2015-00644 and IPR2015-00630.
Gina Shaw, Glatopa Is Strong Out of the Gate [online], Specialty Pharmacy Continuum (Jul. 22, 2015), Retrieved from the internet: <URL://www.specialtypharmacycontinuum.com/Article/PrintArticle? articleID=33101>, submitted as Exhibit 1124 on Mar. 9, 2016 in Inter Partes Review Case. Nos. IPR2015-00643, IPR2015-00644 and IPR2016-00830.
David Risinger et al., Morgan Stanley Analyst Report: Teva Pharmaceutical industries Ltd. (Mar. 14, 2014), submitted as Exhibit 11.25 on Mar. 9, 2015 in Inter Partes Review Case Nos. IPR2015-00643, IPR2015-00644 and IPR2015-00830.
Organization Disclosures [online], MS Coalitton [retrieved on Mar. 6, 2016], Retrieved from the internet: <URL://www.ms-coalition.orgj/emergingtherapies/disclosures/organization-disclosures>, submitted as Exhibit 1128 on Mar. 9, 2016 in Inter Partes Review Case Nos. IPR2015-00543, IPR2015-00644 and IPR2015-00830.
Alisa Woods, The Costs of Multiple Sclerosis Treatment [online], Everyday Health (Feb. 22, 2016) [retrieved on Mar. 6, 2016], Retrieved from the internet: <URL://www.everydayhealth.com/multiple-sclerosis/treatment/costs-of-ms-treatment/>, submitted as Exhibit 1129 on Mar. 9, 2016 in Inter Partes Review Case Nos. IPR2015-00643, IPR2015-00644 and IPR2015-00830.
Geeta Anand, Through Charities, Drug Makers Help People—and Themselves [online], Wall St. J. (Dec. 1, 2005) [retrieved on Mar. 8, 2016]. Retrieved from the Internet: <URL://www.wsj.com/articles/SB113339802749110822>, submitted as Exhibit 1130 on Mar. 9, 2016 in Inter Partes Review Case Nos. IPR2015-00643, IPR2015-00644 and IPR2015-00830.
Malcolm Gladwell, High Prices: How to think about prescription drugs [online], New Yorker (Oct. 25, 2004) [retrieved on Sep. 8, 2012]. Retrieved from the internet: <URL://www.newyorker.com/magazine/2004/10/25/high-prices>, submitted as Exhibit 1131 on Mar. 9, 2016 in Inter Partes Review Case Nos. IPR2015-00643, IPR2015-00644 and IPR2015-00830.
Ernst R. Berndt et al., An Analysis of the Diffusion of New Antidepressants: Variety, Quality, and Marketing Efforts, 5(1) J. of Mental Health Pol'y and Econs. 3 (2002), submitted as Exhibit 1132 on Mar. 9, 2016 in Inter Partes Review Case Nos. IPR2015-00643, IPR2015-00644 and IPR2015-00830.
Ernst R. Berndt et al., Information, marketing, and pricing in the U.S. antiulcer drug market, 85(2) Am. Econ. Rev. 100 (1995), submitted as Exhibit 1133 on Mar. 9, 2016 in inter Partes Review Case Nos. IPR2015-00643, IPR2015-00644 and IPR2015-00830.
FDA approves new MS treatment regimen developed at Wayne State University by Dr. Omar Khan [online], Division of Research—Research@wayne [retrieved on Mar. 8, 2016]. Retrieved from the Internet: <URL://research.wayne.edu/rwnews/article.php?id=1319>, submitted as Exhibit 1134 on Mar. 9, 2016 in Inter Partes Review Case Nos. IPR2015-00643, IPR2015-00644 and IPR2015-00830.
Order Construing the Terms of U.S. Patent Nos. 8,232,250, 8,399,413, 8,969,302, and 9,155,770, In Re Copaxone 40 mg Consolidated Cases, No. 14-1171-GMS (consolidated) (D. Del. Mar, 7, 2016), ECF No. 214, submitted as Exhibit 1136 on Mar. 9, 2016 in Inter Partes Review Case Nos. IPR2015-00643, IPR2015-00644 and IPR2015-00830.
Stipulation and [Proposed] Order Concerning Claim Construction Dispute, In Re Copaxone 40 mg Consolidated Cases, No. 14-1171-GMS (consolidated) (D. Del. Feb. 12, 2016), ECF No. 194, submitted as Exhibit 1137 on Mar. 9, 2016 in Inter Partes Review Case Nos. IPR2015-00643, IPR2015-00644 and IPR2015-00830.

Transcript of Trial Testimony, *Teva Pharms. USA, Inc.* v. *Sandoz, Inc.*, No. 109-cv-08824 (S.D.N.Y. Sep. 7, 2011), ECF No. 205, submitted as Exhibit 1138 on Mar. 9, 2016 in Inter Partes Review Case Nos. IPR2015-00643, IPR2015-00644 and IPR2015-00830.
Ampyra® Prescribing Information, published Dec. 2014 by Acorda Therapeutics, Inc, submitted as Exhibit 1139 on Mar. 9, 2016 in Inter Partes Review Case Nos. IPR2015-00643, IRR2015-00644 and IPR2015-00830.
Xinke Zhang & Joel W. Hay, Cost-effectiveness of Fingolimod, Teriflunomide, Dimethyl Fumarate and Intramuscular Interferon Beta-1a in Relapsing-remitting Multiple Sclerosis, poster presentation aileqedly at Monday Morning, PND20, ISPOR 19th Annual International Conference, Montreal, Quebec, Canada, allegedly on May 2014, submitted as Exhibit 1101 on Mar. 9, 2016 in Inter Partes Review Case Nos. IPR2015-00643, IPR2015-00644 and IPR2015-00830.
Xinke Zhang & Joel W. Hay, Cost-effectiveness of Fingolimod, Teriflunomide, Dimethyl Fumarate and Intramuscular Interferon Beta-1a in Relapsing-remitting Multiple Sclerosis, poster presentation allegedly at the American Society for Health Economics 5th Biennial Conference, Los Angeles, CA, allegedly on Jun. 2014, submitted as Exhibit 1102 on Mar. 9, 2016 in Inter Partes Review Case Nos. IPR2015-06043, IPR2015-00644 and IPR2015-00830.
3-Times-A-Week Copaxone® 40 Mg [online], Teva [retrieved date unknown]. Retrieved from the internet <URL://www.copaxone.com/about-copaxone/copaxone-40-mg>, submitted as Exhibit 1106 on Mar. 9, 2016 in Inter Partes Review Case Nos. IPR2015-00643, IPR2015-00644 and IPR2015-00830.
10 Disease-modifying Treatments [online], Momentum-MagazineOnline.com; allegedly on Nov. 2013 [retrieved date unknown]. Retrieved from the Internet: <URL://bit.ly/1eVa0jT>, submitted as Exhibit 1119 on Mar. 9, 2016 in Inter Partes Review Case Nos. IPR2015-00643, IPR2015-00644 and IPR2015-00830.
Specialty Maximum Allowable Cost (MAC) [online], Missouri Dep't of Soc. Servs., alleged date Mar. 1, 2016 [retrieved date unknown]. Retrieved from the internet: <URL://dss.mo.gov/mhd/cs/pharmacy/pdf/madspec.pdf>, submitted as Exhibit 1123 on Mar. 9, 2016 in Inter Partes Review Case Nos. IPR2015-00643, 1PR2015-00644 and IPR2015-00830.
Financial Support [online], Teva Neuroscience 2015, [Retrieved allegedly on Dec. 2, 2015]. Retrieved from the internet <URL://www.copaxone.com/shared-solutions/copaxone-savings-and-benefits>, submitted as Exhibit 1126 on Mar. 9, 2016 in Inter Partes Review Case Nos. IPR2015-00643, IPR2015-00644 and IPR2015-00830.
Copaxone [online], Teva Neuroscience 2015, [Retrieved allegedly on Jan. 8, 2016]. Retrieved from the Internet: <URL://www.copaxone.com>, submitted as Exhibit 1127 on Mar. 9, 2016 in Inter Partes Review Case Nos. IPR2015-00643, IPR2015-00644 and IPR2015-00830.
File wrapper of U.S. Appl. No. 11/651,212, dated Jan. 9, 2007 to Mar. 9, 2010, submitted as Exhibit 1135 on Mar. 9, 2016 in Inter Partes Review Case Nos. IPR2019-00643, IPR2015-00644 and IPR2015-00830.
Sixth Updated List of Petitioners' Exhibits, submitted as Notice 76 on Apr. 22, 2016 in Inter Partes Review Case Nos. IPR2015-00643.
Sixth Updated List of Petitioners' Exhibits, submitted as Notice 77 on Apr. 22, 2016 in Inter Partes Review Case Nos. IPR2015-00644.
Sixth Updated List of Petitioners' Exhibits, submitted as Notice 71 on Apr. 22, 2016 in Inter Partes Review Case Nos. IPR2015-00830.
Updated List of Patent Owner's Exhibits, submitted as Notice 73 on Apr. 22, 2016 in Inter Partes Review Case Nos, IPR2015-00643.
Updated List of Patent Owner's Exhibits, submitted as Notice 74 on Apr. 22, 2016 in Inter Partes Review Case Nos. IPR2015-00644.
Updated List of Patent Owner's Exhibits, submitted as Notice 68 on Apr. 22, 2016 in Inter Partes Review Case Nos. IPR2015-00830.
Redacted Expert Report of Ari Green, M.D., dated Apr. 19, 2016, which was prepared in connection with *In Re Copaxone 40 Mg Cases*, Case No. 1:14-cv-1171-GMS (Consolidated) in the United States District Court for District of Delaware.
Redacted Opening Expert Report of Andrew R. Pachner, Ph. D., dated Apr. 19, 2016, which was prepared in connection with *In Re*

(56) References Cited

OTHER PUBLICATIONS

*Copaxone 40 Mg Cases*, Case No. 1:14-cv-1171-GMS (Consolidated) in the United States District Court for District of Delaware.
Redacted Opening Expert Report of Samuel J. Pleasure, M.D., Ph.D., dated Apr. 19, 2016, which was prepared in connection with *In Re Copaxone 40 Mg Case*, Case. No. 1:14-cv-1171-GMS (Consolidated) in the United States District Court for District of Delaware.
Patent Owner Yeda Research & Development Co. Ltd.'s Preliminary Response, dated May 24, 2016, which was filed on May 24, 2016 in connection with *Mylan Pharmaceuticals Inc.* v. *Yeda Research & Development Co. Ltd.*, Post Grant Review of. U.S. Pat. No. 9,155,776 in the United States Patent and Trademark Office Trial and Appeal Board (Case No. PGR2016-00010).
Declaraction of Edward J. Fox, M.D., Ph.D. in Support of Patent Owner Yeda's Preliminary Response, dated May 23, 2016, which was filed on May 24, 2016 as Exhibit 2001 in connection with *Mylan Pharmaceuticals Inc.* v. *Yeda Research & Development Co. Ltd.*, Post Grant Review of U.S. Pat. No. 9,155,776 in the United States Patent and Trademark Office Patent Trial and Appeal Board (Case No. PGR2016-00010).
U.S. Appl. No. 61/274,687, filed Aug. 20, 2009 submitted as Exhibit 2002 on May 24, 2016 in Post Grant Review Case No. PGR2016-00010.
Claim Chart of U.S. Appl. No. 9,155,776, issued Oct. 13, 2015 submitted as Exhibit 2003 on May 24, 2016 in Post Grant Review Case No. PGR2016-00010.
U.S. Appl. No. 13/770,677, filed Feb. 19, 2013 and Preliminary Amendment dated Feb. 19, 2013 filed in connection with U.S. Appl. No. 13/770,677, filed Feb. 19, 2013, submitted together as Exhibit 2004 on May 24, 2016 in Post Grant Review Case No. PGR2016-00010.
Defendant's Initial Joint Invalidity Contentions Regarding U.S. Pat. No. 9,155,776 B2, which was filed in connection with *In Re Copaxone 40 Mg Cases*, Case No. 1:14-cv-1171-GMS (Consolidated) in the United States District Court for District of Delaware, submitted as Exhibit 2005 on May 24, 2016 in Post Grant Review Case No. PGR2016-00010.
U.S. Appl. No. 12/806,684, filed Aug. 19, 2010 and Preliminary Amendment dated Aug. 19, 2010 filed in connection with U.S. Appl. No. 12/806,684, filed Aug. 19, 2010, submitted together as Exhibit 2006 on May 24, 2016 in Post Grant Review Case No. PGR2016-00010.
U.S. Appl. No. 61/337,612, filed Feb. 11, 2010, submitted as Exhibit 2007 on May 24, 2016 in Post Grant Review Case No. PGR2016-00010.
Khan et al., "Three Times Weekly Glatiramer Acetate in Relapsing-Remitting Multiple Sclerosis," Ann. Neurol., 2013; 73:705-713, submitted as Exhibit 2008 on May 24, 2016 in Post Grant Review Case No. PGR2016-00010.
Business Wire, "Teva Announces Top-Line Results from GALA Phase III Trial Evaluating a New Dosage for Glatiramer Acetate Given Three Times Weekly for Relapsing-Remitting Multiple Sclerosis, " dated Jun. 14, 2012, submitted as Exhibit 2009 on May 24, 2016 in Post Grant Review Case No. PGR2016-00010.
Reuters Press Release, "New Data Presented at the 28th ECTRIMS Congress Showcase Teva's Ongoing Commitment to Multiple Sclerosis Research," dated Oct. 8, 2012, submitted as Exibit 2010 on May 24, 2016 in Post Grant Review Case No. PGR2016-00010.
Khan et al., "A phase 3 trial to assess the efficacy and safety of glatiramer acetate injections 40 mg administered 3 times a week compared to placebo," Abstract 166, Multiple Sclerosis Journal 2012; 18(54)509-520, submitted as Exhibit 2011 on May 24, 2016 in Post Grant Review Case No. PGR2016-00010.
U.S. Appl. No, 14/630,326, filed Feb. 24, 2015, and Application Data Sheet dated Feb. 24, 2015 and Preliminary Amendment: dated Feb. 24, 2015, filed in connection with U.S. Appl. No. 14/630,326, filed Feb. 24, 2015, submitted together as Exhibit 2012 on May 24, 2016 in Post Grant Review Case No. PGR2016-00010.
Cobert, et al., "Practical Drug Safety from A to Z," Jones and Bartlett Publishers, 2009, pp, 327-329, submitted as Exhibit 2013 on May 24, 2016 in Post Grant Review Case No. PGR2016-00010.
World Health Organization, "A Practical Handbook on the Pharmacovigilance of Antiretroviral Medicines," 2009, 129-133, submitted as Exhibit 2014 on May 24, 2016 Case No. PGR2016-00010.
Patent Owner's Exhibit List, dated May 24, 2016, submitted as Exhibit 2000 on May 24, 2016 in Post Grant Review Case No. PGR2016-00010.

LOW FREQUENCY GLATIRAMER ACETATE THERAPY

This application is a continuation of U.S. Ser. No. 14/630,326, filed Feb. 24, 2015, which is a continuation of U.S. Ser. No. 13/770, 677, filed Feb. 19, 2013, now U.S. Pat. No. 8,969,302, which is a continuation of U.S. Ser. No. 12/806,684, filed Aug. 19, 2010, now U.S. Pat. No. 8,399,413, which claims the benefit of U.S. Provisional Application Nos. 61/337,612, filed Feb. 11, 2010 and 61/274,687, filed Aug. 20, 2009. the contents of all of which are hereby incorporated by reference in their entirety.

Throughout this application various publications are referenced by their full citations. The disclosures of these publications in their entireties are hereby incorporated by reference into this application in order to more fully describe the state of the art to which this invention pertains.

BACKGROUND OF THE INVENTION

Multiple Sclerosis (MS) is a chronic, debilitating disease of the central nervous system (CNS). MS has also been classified as an autoimmune disease. MS disease activity can be monitored by magnetic resonance imaging (MRI) of the brain, accumulation of disability, as well as rate and severity of relapses.

There are five main forms of multiple sclerosis:
1) Benign Multiple Sclerosis:
Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis.
2) Relapsing-Remitting Multiple Sclerosis (RRMS):
Patients suffering from RRMS experience sporadic exacerbations or relapses, as well as periods of remission. Lesions and evidence of axonal loss may or may not be visible on MRI for patients with RRMS.
3) Secondary Progressive Multiple Sclerosis (SPMS):
SPMS may evolve from RRMS. Patients afflicted with SPMS have relapses, a diminishing degree of recovery during remissions, less frequent remissions and more pronounced neurological deficits than RRMS patients. Enlarged ventricles, which are markers for atrophy of the corpus callosum, midline center and spinal cord, are visible on MRI of patients with SPMS.
4) Primary Progressive Multiple Sclerosis (PPMS):
PPMS is characterized by a steady progression of increasing neurological deficits without distinct attacks or remissions. Cerebral lesions, diffuse spinal cord damage and evidence of axonal loss are evident on the MRI of patients with PPMS.
5) Progressive-Relapsing Multiple Sclerosis (PRMS):
PRMS has periods of acute exacerbations while proceeding along a course of increasing neurological deficits without remissions. Lesions are evident on MRI of patients suffering from PRMS (Multiple sclerosis: its diagnosis, symptoms, types and stages, 2003, albany.net/.about .tjc/multiple-sclerosis.html; What are the Types of Multiple Sclerosis?, 2005, <imaginis.com/multiple-sclerosis/types-of-ms.asp?mode=1>).

Chronic progressive multiple sclerosis is a term used to collectively refer to SPMS, PPMS, and PRMS (Types of Multiple Sclerosis (MS), 2005, <themcfox.com/multiple-sclerosis/types-of-ms/types-of-multi-ple-sclerosis.htm>). The relapsing forms of multiple sclerosis are SPMS with superimposed relapses, RRMS and PRMS.

Glatiramer acetate (GA), a mixture of polypeptides which do not all have the same amino acid sequence, is marketed under the tradename Copaxone®. GA comprises the acetate salts of polypeptides containing L-glutamic acid, L-alanine, L-tyrosine and L-lysine at average molar fractions of 0.141, 0.427, 0.095 and 0.338, respectively. The average molecular weight of Copaxone® is between 5,000 and 9,000 daltons. ("Copaxone", Physician's Desk Reference, (2005), Medical Economics Co., Inc., (Montvale, N.J.), 3115.) Chemically, glatiramer acetate is designated L-glutamic acid polymer with L-alanine, L-lysine, L-tyrosine, acetate (salt).

Its structural formula is:

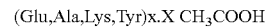

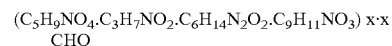

CAS-147245-92-9

Copaxone® ("Copaxone", Full Prescribing Information, (February, 2009), FDA Marketing. Label) (20 mg glatiramer acetate daily injection) is an approved therapy for patients with relapsing remitting multiple sclerosis (RRMS), including patients who have experienced a first clinical episode and have MRI features consistent with multiple sclerosis.

GA has also been disclosed for use in the treatment of other autoimmune diseases (U.S. Patent Publication No. 2002/0055466 A1 (R. Aharoni at al.), inflammatory non-autoimmune diseases (U.S. Patent Publication No. 2005/0014694 A1 (V. Wee Yong et al.); and U.S. Patent Application No. 2002/0077278 A1, published Jun. 20, 2002 (Young et al.)) and other diseases (U.S. Patent Publication Nos. 2003/0004099 A1 and 2002/0037848 A1 (Eisenbach-Schwartz, et al.); U.S. Pat. No. 6,514,938 B1, issued Feb. 4, 2003 (Gad et al.); PCT International Publication No. WO 01/60392, published Aug. 23, 2001 (Gilbert at al.); PCT International. Publication No. WO 00/27417, published May 19, 2000 (Aharoni et al.); and PCT International Publication No. WO 01/97846, published Dec. 27, 2001 (Moses at al.).

The 20 mg/day subcutaneous (s.c.) dose has been shown to reduce the total number of enhancing lesions in MS patients as measured by MRI (G. Comi et al., European/Canadian Multicenter, Double-Blind, Randomized, Placebo-Controlled Study of the Effects of Glatiramer Acetere on Magnetic Resonance Imaging-Measured Disease Activity and Burden in Patients with Relapsing Multiple Sclerosis, Ann. Neurol. 49:290-297 (2001)).

Safety data accumulated for GA in clinical trials shows that the drug product is safe and well tolerated.

Disclosed is an effective low frequency dosage regimen of GA administration to patients suffering from a relapsing form of multiple sclerosis, including patients who have experienced a first clinical episode and have MRI features consistent with multiple sclerosis.

SUMMARY OF THE INVENTION

This invention provides a method of alleviating a symptom of relapsing-remitting multiple sclerosis in a human patient suffering from relapsing-remitting multiple sclerosis or a patient who has experienced a first clinical episode and is determined to be at high risk of developing clinically definite multiple sclerosis comprising administering to the human patient three subcutaneous injections of a therapeutically effective dose of glatiramer acetate over a period of seven days with at least one day between every subcutaneous injection so as to thereby alleviate the symptom of the patient.

This invention also provides a method of increasing the tolerability of GA treatment in a human patient suffering from relapsing-remitting multiple sclerosis or a patient who has experienced a first clinical episode and is determined to be at high risk of developing clinically definite multiple sclerosis which comprises reducing the frequency of subcutaneous injections of a pharmaceutical composition comprising a therapeutically effective dose of glatiramer acetate to three times over a period of seven days with at least one day between every injection.

In another embodiment, the therapeutically effective dose of glatiramer acetate is 40 mg/ml.

This invention also provides a use of glatiramer acetate in the preparation of a medicament for treating relapsing-remitting multiple sclerosis in a human patient suffering from relapsing-remitting multiple sclerosis or a patient who has experienced a first clinical episode and is determined to be at high risk of developing clinically definite multiple sclerosis wherein the administration pattern of the medicament is three subcutaneous injections of a therapeutically effective dose of glatiramer acetate over a period of seven days with at least one day between every subcutaneous injection.

This invention additionally provides a use of glatiramer acetate in the preparation of a medicament for treating relapsing-remitting multiple sclerosis in a human patient suffering from relapsing-remitting multiple sclerosis or a patient who has experienced a first clinical episode and is determined to be at high risk of developing clinically definite multiple sclerosis wherein the medicament is prepared for an administration pattern of three subcutaneous injections of a therapeutically effective dose of glatiramer acetate over a period of seven days with at least one day between every subcutaneous injection.

This invention yet also provides a use of glatiramer acetate in the preparation of a medicament for increasing the tolerability of GA treatment in a human patient suffering from relapsing-remitting multiple sclerosis or a patient who has experienced a first clinical episode and is determined to be at high risk of developing clinically definite multiple sclerosis wherein the administration pattern of the medicament is three subcutaneous injections of a therapeutically effective dose of glatiramer acetate over a period of seven days with at least one day between every subcutaneous injection.

This invention further provides a use of glatiramer acetate in the preparation of a medicament for increasing the tolerability of GA treatment in a human patient suffering from relapsing-remitting multiple sclerosis or a patient who has experienced a first clinical episode and is determined to be at high risk of developing clinically definite multiple sclerosis wherein the medicament is prepared for an administration pattern of three subcutaneous injections of a therapeutically effective dose of glatiramer acetate over a period of seven days with at least one day between every subcutaneous injection.

This invention provides glatiramer acetate for use in treating relapsing-remitting multiple sclerosis in a human patient suffering from relapsing-remitting multiple sclerosis or a patient who has experienced a first clinical episode and is determined to be at high risk of developing clinically definite multiple sclerosis by three subcutaneous injections over a period of seven days with at least one day between every subcutaneous injection.

This invention also provides glatiramer acetate for use in increasing the tolerability of GA treatment in a human patient suffering from relapsing-remitting multiple sclerosis or a patient who has experienced a first clinical episode and is determined to be at high risk of developing clinically definite multiple sclerosis by three subcutaneous injections over a period of seven days with at least one day between every subcutaneous injection.

DETAILED DESCRIPTION OF THE INVENTION

This invention provides a method of alleviating a symptom of relapsing-remitting multiple sclerosis in a human patient suffering from relapsing-remitting multiple sclerosis or a patient who has experienced a first clinical episode and is determined to be at high risk of developing clinically definite multiple sclerosis comprising administering to the human patient three subcutaneous injections of a therapeutically effective dose of glatiramer acetate over a period of seven days with at least one day between every subcutaneous injection so as to thereby alleviate the symptom of the patient.

In another embodiment, there are three injections for every seven days and there must be at least one day between each injection. In a further embodiment, possible injection schedules include Day 1, Day 3, Day 5; Day 1, Day 3, Day 6; Day 1, Day 3, Day 7; Day 1, Day 4, Day 6; Day 1, Day 4, Day 7; Day 1, Day 5, Day 7; Day 2, Day 4, Day 6; Day 2, Day 4, Day 7; Day 2, Day 5, Day 7; or Day 3, Day 5, Day 7.

In an embodiment, alleviating a symptom comprises reducing the frequency of relapses.

In yet another embodiment, alleviating a symptom comprises reducing the mean cumulative number of Gd-enhancing lesions in the brain of the patient.

In another embodiment, alleviating a symptom comprises reducing the mean number of new $T_2$ lesions in the brain of the patient.

In a further embodiment, alleviating a symptom comprises reducing the cumulative number of enhancing lesions on $T_1$-weighted images in the patient.

In another embodiment, alleviating a symptom comprises reducing brain atrophy in the patient.

In another embodiment, alleviating a symptom comprises increasing the time to a confirmed relapse in the patient.

In another embodiment, alleviating a symptom comprises reducing the total number of confirmed relapses in the patient.

In another embodiment, alleviating a symptom comprises reducing the progression of MRI-monitored disease activity in the patient.

In another embodiment, alleviating a symptom comprises reducing total volume of $T_2$ lesions in the patient.

In another embodiment, alleviating a symptom comprises reducing the number of new hypointense lesions on enhanced $T_1$ scans in the patient.

In another embodiment, alleviating a symptom comprises reducing the total volume of hypointense lesions on enhanced $T_1$ scans in the patient.

In another embodiment, alleviating a symptom comprises reducing the level of disability as measured by EDSS Score in the patient.

In another embodiment, alleviating a symptom comprises reducing the change in EDSS Score in the patient.

In another embodiment, alleviating a symptom comprises reducing the change in Ambulation Index in the patient.

In another embodiment, alleviating a symptom comprises reducing the level of disability as measured by EuroQoL (EQ5D) questionnaire in the patient.

In another embodiment, alleviating a symptom comprises reducing the level of disability as measured by the work productivity and activities impairment—General Health (WPAI-GH) questionnaire in the patient.

In an additional embodiment, the pharmaceutical composition is in a prefilled syringe for self administration by the patient.

In yet another embodiment, the therapeutically effective dose of glatiramer acetate is 40 mg/ml. In a further embodiment, the therapeutically effective dose of glatiramer acetate is 40 mg/0.75 ml.

In a further embodiment, the patient has not received glatiramer acetate therapy prior to initiation of the subcutaneous injections.

In an embodiment, the pharmaceutical composition is in the form of a sterile solution.

In another embodiment, the pharmaceutical composition further comprises mannitol.

In yet another embodiment, the pharmaceutical composition has a pH in the range of 5.5 to 8.5.

In an embodiment, the pharmaceutical composition has a pH in the range of 5.5 to 7.0.

In an embodiment the frequency of an immediate post injection reaction or the frequency of an injection site reaction is reduced relative to daily subcutaneous administration of 20 mg glatiramer acetate.

This invention also provides a method of increasing the tolerability of GA treatment in a human patient suffering from relapsing-remitting multiple sclerosis or a patient who has experienced a first clinical episode and is determined to be at high risk of developing clinically definite multiple sclerosis which comprises reducing the frequency of subcutaneous injections of a pharmaceutical composition comprising a therapeutically effective dose of glatiramer acetate to three times over a period of seven days with at least one day between every injection.

In another embodiment, increasing the tolerability of GA treatment in the human patient suffering from a relapsing form of multiple sclerosis comprises reducing the frequency of an immediate post injection reaction.

In yet another embodiment, the immediate post injection reaction is palpitations, feeling hot, flushing, hot flushes, tachycardia, dyspnoea, chest discomfort, chest pain, non-cardiac chest, asthenia, back pain, bacterial infection, chills, cyst, face edema, fever, flu syndrome, infection, injection site erythema, injection site hemorrhage, injection site induration, injection site inflammation, injection site mass, injection site pain, injection site pruritus, injection site urticaria, injection site welt, neck pain, pain, migrane, syncope, tachycardia, vasodilatation, anorexia, diarrhea, gastroenteritis, gastrointestinal disorder, nausea, vomiting, ecchymosis, peripheral edema, arthralgia, agitation, anxiety, confusion, foot drop, hypertonia, nervousness, nystagmus, speech disorder, tremor, vertigo, bronchitis, dyspnea, laryngismus, rhinitis, erythema, herpes simplex, pruritus, rash, skin nodule, sweating, urticaria, ear pain, eye disorder, dysmenorrheal, urinary urgency, or vaginal moniliasis.

In an additional embodiment, increasing the tolerability of GA treatment in the human patient suffering from a relapsing form of multiple sclerosis comprises reducing the frequency of an injection site reaction.

In a further embodiment, the injection site reaction is erythema, hemorrhage, induration, inflammation, mass, pain, pruritus, urticaria, or welt that occurs immediately around the site of injection.

In an embodiment, a single clinical attack includes a clinical episode of optic neuritis, blurring of vision, diplopia, involuntary rapid eye movement, blindness, loss of balance, tremors, ataxia, vertigo, clumsiness of a limb, lack of coordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

In another embodiment, prior to administration the patient has at least 1 cerebral lesion detectable by an MRI scan and suggestive of multiple sclerosis.

In yet another embodiment, the lesion is associated with brain tissue inflammation, myelin sheath damage or axonal damage.

In an additional embodiment, the lesion is a demyelinating white matter lesion visible on brain MRI.

In a further embodiment, the white matter lesions are at least 3 mm in diameter.

This invention also provides a use of glatiramer acetate in the preparation of a medicament for treating relapsing-remitting multiple sclerosis in a human patient suffering from relapsing-remitting multiple sclerosis or a patient who has experienced a first clinical episode and is determined to be at high risk of developing clinically definite multiple sclerosis wherein the administration pattern of the medicament is three subcutaneous injections of a therapeutically effective dose of glatiramer acetate over a period of seven days with at least one day between every subcutaneous injection.

This invention additionally provides a use of glatiramer acetate in the preparation of a medicament for treating relapsing-remitting multiple sclerosis in a human patient suffering from relapsing-remitting multiple sclerosis or a patient who has experienced a first clinical episode and is determined to be at high risk of developing clinically definite multiple sclerosis wherein the medicament is prepared for an administration pattern of three subcutaneous injections of a therapeutically effective dose of glatiramer acetate over a period of seven days with at least one day between every subcutaneous injection.

This invention yet also provides a use of glatiramer acetate in the preparation of a medicament for increasing the tolerability of GA treatment in a human patient suffering from relapsing-remitting multiple sclerosis or a patient who has experienced a first clinical episode and is determined to be at high risk of developing clinically definite multiple sclerosis wherein the administration pattern of the medicament is three subcutaneous injections of a therapeutically effective dose of glatiramer acetate over a period of seven days with at least one day between every subcutaneous injection.

This invention further provides a use of glatiramer acetate in the preparation of a medicament for increasing the tolerability of GA treatment in a human patient suffering from relapsing-remitting multiple sclerosis or a patient who has experienced a first clinical episode and is determined to be at high risk of developing clinically definite multiple sclerosis wherein the medicament is prepared for an administration pattern of three subcutaneous injections of a therapeutically effective dose of glatiramer acetate over a period of seven days with at least one day between every subcutaneous injection.

This invention provides glatiramer acetate for use in treating relapsing-remitting multiple sclerosis in a human patient suffering from relapsing-remitting multiple sclerosis or a patient who has experienced a first clinical episode and is determined to be at high risk of developing clinically definite multiple sclerosis by three subcutaneous injections over a period of seven days with at least one day between every subcutaneous injection.

This invention also provides glatiramer acetate for use in increasing the tolerability of GA treatment in a human patient suffering from relapsing-remitting multiple sclerosis or a patient who has experienced a first clinical episode and is determined to be at high risk of developing clinically definite multiple sclerosis by three subcutaneous injections over a period of seven days with at least one day between every subcutaneous injection.

Definitions

As used herein, immediate post injection reaction (IRPR) refers to a reaction such as, palpitations, feeling hot, flushing, hot flushes, tachycardia, dyspnoea, chest discomfort, chest pain, and non-cardiac chest pain that occurs immediately following injection. Reactions may also include asthenia, back pain, bacterial infection, chills, cyst, face edema, fever, flu syndrome, infection, injection site erythema, injection site hemorrhage, injection site induration, injection site inflammation, injection site mass, injection site pain, injection site pruritus, injection site urticaria, injection site welt, neck pain, pain, migrane, syncope, tachycardia, vasodilatation, anorexia, diarrhea, gastroenteritis, gastrointestinal disorder, nausea, vomiting, ecchymosis, peripheral edema, arthralgia, agitation, anxiety, confusion, foot drop, hypertonia, nervousness, nystagmus, speech disorder, tremor, vertigo, bronchitis, dyspnea, laryngismus, rhinitis, erythema, herpes simplex, pruritus, rash, skin nodule, sweating, urticaria, ear pain, eye disorder, dysmenorrheal, urinary urgency, and vaginal moniliasis.

As used herein, injection site reaction (ISR) refers to a reaction such as erythema, hemorrhage, induration, inflammation, mass, pain, pruritus, urticaria, and welt that occurs immediately around the site of injection.

As used herein, "tolerability" relates to the level of discomfort associated with GA treatment. Tolerability is associated with the frequency and severity of post injection reactions and injection site reactions. Tolerability influences the period that a patient can follow GA treatment.

As used herein, the term Gd-enhancing lesions, refers to lesions that result from a breakdown of the blood-brain barrier, which appear in contrast studies using gandolinium contrast agents. Gandolinium enhancement provides information as to the age of a lesion, as Gd-enhancing lesions typically occur within a six week period of lesion formation.

As used herein, the term $T_1$-weighted MRI images refers to an MR-image that emphasizes $T_1$ contrast by which lesions may be visualized. Abnormal areas in a $T_1$-weigted MRI image are "hypointense" and appear as dark spots. These spots are generally older lesions.

As used herein, the term $T_2$-weighted MRI image, refers to an MR-image that emphasizes $T_2$ contrast by which lesions may be visualized. $T_2$ lesions represent new inflammatory activity.

As used herein, the term "unit dosage" refers to physically discrete units suited as single administration dose for a subject to be treated, containing a therapeutically effective quantity of active compound in association with the required pharmaceutical carrier, e.g., a syringe.

As used herein, clinically isolated syndrome (CIS) refers to 1) a single clinical attack suggestive of MS and 2) at least one lesion suggestive of MS. As an example, the patient has at least 1 cerebral lesion detectable by an MRI scan and suggestive of multiple sclerosis. As an additional example the lesion is associated with brain tissue inflammation, myelin sheath damage or axonal damage. As another example the lesion is a demyelinating white matter lesion visible on brain MRI. In a further example, the white matter lesions are at least 3 mm in diameter.

The term "single clinical attack" is used synonymously with "first clinical episode", "first clinical attack", and "first clinical event" which, for example, presents as a clinical episode of optic neuritis, blurring of vision, diplopia, involuntary rapid eye movement, blindness, loss of balance, tremors, ataxia, vertigo, clumsiness of a limb, lack of coordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

As used herein, the criteria, as defined by Poser et al. Neurology, March 1983, 13 (3): 227-230, used to determine if a subject meets the condition consistent with clinically definite multiple sclerosis (CDMS) are:

Two attacks and clinical evidence of two separate lesions or
Two attacks; clinical evidence of one lesion and paraclinical evidence of another separate lesion.

An attack (also referred to as an exacerbation, flare, or relapse,) is defined clinically as the sudden appearance or worsening of a symptom or symptoms of neurological dysfunction, with or without objective confirmation.

Clinical evidence of a lesion is defined as signs of neurological dysfunction demonstrable by neurological examination. An abnormal sign constitutes clinical evidence even if no longer present, but was recorded in the past by a competent examiner.

Paraclinical evidence of a lesion is defined as the demonstration by means of various tests and procedures of the existence of a lesion of the CNS that has not produced clinical signs but that may or may not have caused symptoms in the past. Such evidence may be derived from the hot-bath test, evoked response studies, neuroimaging, and expert neurological assessment. These tests are considered to be extensions of the neurological examination and not laboratory procedures.

As used herein, the term "glatiramoid" refers a complex mixture of the acetate salts of synthetic polypeptides, non-uniform with respect to molecular weight and sequence.

This invention is illustrated in the Examples section which follows. This section is set forth to aid in an understanding of the invention but is not intended to, and should not be construed to, limit in any way the invention as set forth in the claims which follow thereafter.

EXPERIMENTAL DETAILS

Example 1

A multinational, multicenter, randomized, phase III parallel-group study performed in subjects with Relapsing-Remitting Multiple Sclerosis (RRMS) to assess the efficacy, safety and tolerability of Glatiramer Acetate (GA) injection 40 mg/ml administered three times weekly by subcutaneous injection over placebo in a double-blind design.

Methods

The study is designed to select three days a week for injection. Three injections are administered for every seven days and there must be at least one day between each injection.

Study Duration

Screening phase: 1 month

Placebo Controlled (PC) Phase: 12 months of 40 mg/ml or matching placebo administered three times weekly by subcutaneous injection.

Open Label (OL) Extension: All subjects will continue treatment with the GA 40 mg/ml administered three times a week, until this dose is commercially available for the treatment of relapsing remitting multiple sclerosis (RRMS) patients or until the development of this dose for MS is stopped by the Sponsor.

Study Population

Subjects with RRMS

Number of Subjects 1350 subjects

Study Objective(s)

To assess the efficacy, safety and tolerability of Glatiramer Acetate (GA) injection 40 mg/ml administered three times weekly compared to placebo in a double-blind study design.

Study Design

Eligible subjects are randomized in a 2:1 ratio (40 mg:placebo) and assigned to one of the following three treatment arms:

1. 40 mg s.c. GA three times weekly (900 subjects)
2. Matching placebo three times weekly (450 subjects)

During the PC phase, subjects are evaluated at study sites for a total of 7 scheduled visits at months: −1 (screening), 0 (baseline), 1, 3, 6, 9, and 12 (End of PC phase).

Subjects successfully completing the study are offered the opportunity to enter into an open label extension in which all subjects will continue treatment with 40 mg/ml GA dose. This is done until the 40 mg/ml GA dose is commercially available for the treatment of relapsing remitting multiple sclerosis (RRMS) patients or until the development of this dose regimen is stopped by the Sponsor.

The termination visit of the PC phase will serve as the baseline visit of the OL phase. This phase will include scheduled visits every 3 months for the first 12 months, then scheduled visits every 6 months and will be completed with a termination visit.

During the study, the following assessments are performed (regardless of the treatment assignment) at the specified time points:

Vital signs are measured at each study visit.

A physical examination is performed at months −1 (screening), 0 (baseline) 6, 12 (end of PC phase) and every 6 months thereafter. In addition, a physical examination will be performed at the termination visit of the OL phase.

The following safety clinical laboratory tests are performed:

Complete blood count (CBC) with differential—at all scheduled visits in the PC phase, and every 12 months thereafter. In addition this test will be performed at the termination visit of the OL phase.

Serum chemistry (including electrolytes, creatinine, urea and liver enzymes) and urinalysis—at all scheduled visits in the PC phase, and every 12 months thereafter. In addition this test will be performed at the termination visit of the OL phase.

Serum β-hCG in women of child-bearing potential is performed at months −1 (screening), 0 (baseline), 12 (end of PC phase), and every 12 months thereafter. In addition this test will be performed at the termination visit of the OL phase.

ECG is performed at months −1 (screening), 0 (baseline), 12 (end of PC phase), and every 12 months thereafter. In addition an ECG will be performed at the termination visit of the OL phase.

Chest X-ray is performed at month −1 (screening) if not performed within 6 months prior to screening visit.

Adverse Events (AEs) are monitored throughout the study.

Concomitant Medications are monitored throughout the study.

Neurological evaluations, including Neurostatus [Functional Systems (FS), Expanded Disability Status Scale (EDSS), Ambulation Index (AI)] are performed at months −1 (screening), 0 (baseline), 3, 6, 9, 12 (end of PC phase) and every 6 months thereafter. In addition, a neurological examination are performed at the termination visit of the OL phase.

The general health status is assessed by the EuroQoL (EQ5D) questionnaire at months 0 (baseline) and 12 (end of PC phase).

Additional quality of life parameters are assessed by the WPAI (Work Productivity and Activities Impairment) Questionnaire at month 0 (baseline), 3, 6, 9 and 12 (end of PC phase).

All subjects undergo MRI scans at months 0 (13-7 days prior to baseline visit), 6 and 12 (end of PC phase). Following the results of the PC phase, the Sponsor may decide to perform an MRI scan at the termination visit of the OL phase.

Relapses are confirmed/monitored throughout the study.

Ancillary Studies

Blood samples for determination of anti-GA antibodies are collected for all subjects at months 0 (baseline), 1, 3, 6, 9, 12 (end of PC phase), 18 and 24.

Blood samples for evaluation of PBL proliferation in response to GA, as well as other immunological parameters, are collected in a subset of subjects at months 0 (baseline), 1, 3, 6, and 12 (end of PC phase).

Blood samples for Pharmacogenetic (PGx) analysis are collected for all subjects twice during the study, preferably at month 0 (baseline) and month 1.

The allowed treatment for a multiple sclerosis relapse will be intravenous methylprednisolone 1 gr/day for up to 5 consecutive days.

Re-Consent Criteria

In case of a confirmed diagnosis of MS relapse (as defined in the protocol), or in case of an increase in EDSS of 1.5 points or more, sustained for at least 3 months, during the placebo-controlled phase, the following actions are taken:

The subject is reminded of the current available MS medications/treatments and the opportunity to terminate the study.

The subject is requested to re-sign an informed consent form if he/she chooses to continue to participate in the study, in the same treatment assignment.

The study is closely monitored through the study course by the sponsor's personnel as well as by an external independent data monitoring committee (DMC) in order to ensure subjects' welfare.

Inclusion/Exclusion

Inclusion Criteria

Subjects must have a confirmed and documented MS diagnosis as defined by the Revised McDonald criteria (Ann Neurol 2005: 58:840-846), with a relapsing-remitting disease course.

Subjects must be ambulatory with an EDSS score of 0-5.5 in both screening and baseline visits.

Subjects must be in a relapse-free, stable neurological condition and free of corticosteroid treatment [intravenous (IV), intramuscular (IM) and/or per os (PO)] or ACTH 30 days prior to screening (month −1) and between screening (month -1) and baseline (month 0) visits.

Subjects must have had experienced one of the following:
At least one documented relapse in the 12 months prior to screening, or
At least two documented relapses in the 24 months prior to screening, or
One documented relapse between 12 and 24 months prior to screening with at least one documented $T_1$-Gd enhancing lesion in an MRI performed within 12 months prior to screening.

Subjects must be between 18 and 55 years of age, inclusive.

Women of child-bearing potential must practice an acceptable method of birth control [acceptable methods of birth control in this study include: surgical sterilization, intrauterine devices, oral contraceptive, contraceptive patch, long-acting injectable contraceptive, partner's vasectomy or a double-barrier method (condom or diaphragm with spermicide)].

Subjects must be able to sign and date a written informed consent prior to entering the study.

Subjects must be willing and able to comply with the protocol requirements for the duration of the study.

Exclusion Criteria

Subjects with progressive forms of MS.

Use of experimental or investigational drugs, and/or participation in drug clinical studies within the 6 months prior to screening.

Use of immunosuppressive (including Mitoxantrone (Novantrone®) or cytotoxic agents within 6 months prior to the screening visit.

Previous use of either natalizumab (Tysabri®) or any other monoclonal antibodies within 2 years prior to screening.

Use of cladribine within 2 years prior to screening.

Previous treatment with immunomodulators (including IFNβ 1a and 1b, and IV Immunoglobulin (IVIg) within 2 months prior to screening.

Previous use of GA or any other glatiramoid.

Chronic (more than 30 consecutive days) systemic (IV, PO or IM) corticosteroid treatment within 6 months prior to screening visit.

Previous total body irradiation or total lymphoid irradiation.

Previous stem-cell treatment, autologous bone marrow transplantation or allogenic bone marrow transplantation.

Known human immunodeficiency virus (HIV) positive status.

Pregnancy or breastfeeding.

Subjects with a clinically significant or unstable medical or surgical condition that would preclude safe and complete study participation, as determined by medical history, physical exams, ECG, abnormal laboratory tests and chest X-ray. Such conditions may include hepatic, renal or metabolic diseases, systemic disease, acute infection, current malignancy or recent history (5 years) of malignancy, major psychiatric disorder, history of drug and/or alcohol, abuse and allergies that could be detrimental according to the investigator's judgment.

A known history of sensitivity to Gadolinium.

Inability to successfully undergo MRI scanning.

A known drug hypersensitivity to mannitol.

Route and Dosage Form
Glatiramer Acetate 40 mg in 1 ml for subcutaneous injection in a pre-filled syringe (PFS), administered three times a week.
Matching placebo injection (mannitol in 1 ml WFI) for subcutaneous injection in a pre-filled syringe (PFS).

Outcome Measures

Primary Outcome Measure
The total number of confirmed relapses during the 12 month PC phase.

Secondary Outcome Measure
The number of new $T_2$ lesions at month 12 (end of PC phase) as compared to baseline scan.
The cumulative number of enhancing lesions on $T_1$-weighted images taken at months 6 and 12 (end of PC phase).
Brain atrophy as defined by the percent brain volume change from baseline to month 12 (end of PC phase).

Exploratory Endpoints: The following assessments are presented in an exploratory manner.
The time to the first confirmed relapse during the placebo-controlled phase.
The proportion of relapse-free subjects during the placebo-controlled phase.
The total number of confirmed relapses during the placebo-controlled phase requiring hospitalization and/or IV steroids.
The proportion (%) of subjects with confirmed EDSS progression during the placebo-controlled phase (progression of at least 1 EDSS point sustained for at least 3 months).
Change from baseline to month 12 (end of placebo-controlled phase) in EDSS Score.
Change from baseline to month 12 (end of placebo-controlled phase) in Ambulation Index.
The total volume of $T_2$ lesions at month 12 (end of placebo-controlled phase)
The number of new hypointense lesions on enhanced $T_1$ scans at month 12 (end of placebo-controlled phase) as compared to the baseline scan.
The total volume of hypointense lesions on enhanced $T_1$ scans at month 12 (end of placebo-controlled phase).
Brain atrophy as defined by the percentage change from baseline to month 12 (end of placebo-controlled phase) in normalized gray matter volume and in normalized white matter volume.
The general health status, as assessed by the EuroQoL (EQ5D) questionnaire.
Assessment of the effect of general health and symptom severity on work, using the work productivity and activities impairment General Health (WPAI-GH) questionnaire.

Safety and Tolerability Outcome Measures

Safety
Adverse events
Vital signs
ECG findings
Clinical laboratory parameters

Tolerability
Proportion of subjects (%) who prematurely discontinued from the study, reason of discontinuation and the time to withdrawal.
Proportion of subjects (%) who prematurely discontinued from the study due to AEs and the time to withdrawal.

Statistical Considerations
The sample size considerations for the study are based on the following assumptions:

An individual subject's number of confirmed relapses during a one year period reflects a Poisson process with an individual rate of $\lambda i$, and this individual subject rates $\lambda i$ are exponentially distributed with mean $1/\theta$, where $\theta$ is the population's annualized relapse rate. This approach models the total number of confirmed relapses as an Over Dispersed Poisson distribution.

The expected annualized relapse rate in an untreated subject population is $\theta=0.35$ relapses per year.

Treatment with 40 mg s.c. GA three times weekly reduces the subject population annualized relapse rate by 30% or more when compared to the placebo group. That is, the expected annualized relapse rate of the GA treated populations is $\theta=0.245$ relapses per year or less.

In addition, the following are also incorporated in the sample size calculation:

15% of the subjects drop out during the treatment duration. This drop out rate is taken into account in the calculations, as on the average, a subject who drops out of the study contributes 6 months of exposure to the treatment Hochberg's step-up modification to Bonferroni's method is used to maintain the experiment-wise type-I error when comparing multiple treatment arms to placebo, and the p-values for the IAs are calculated using the O'brien-Fleming alpha spending functions.

A simulation study accounting for the above underlying assumptions used the Quasi-Likelihood (over-dispersed) Poisson Regression (SAS® PROC GENMOD), revealed that a total of 1350 subjects (900 subjects in the 40 mg GA arm, and 450 subjects to the placebo arm) provide approximately 90% power to detect a significant difference in the total number of confirmed relapses as described above.

The analysis of the total numbers of confirmed relapses during the study period is based on baseline adjusted Quasi-Likelihood (over-dispersed) Poisson Regression.

The analysis of the number of new $T_2$ lesions at month 12 and of the cumulative number of enhancing lesions on $T_1$-weighted images taken at months 6 and 12 is based on baseline-adjusted Negative Binomial Regression.

The analysis of Brain Atrophy will be based on Analysis of Covariance (ANCOVA).

Results

Primary Outcome Measure

Treatment with 40 mg s.c. GA three times weekly reduces the subject population annualized relapse rate by 30% or more when compared to the placebo group. Treatment with 40 mg s.c. GA three times weekly is at least as effective as 20 mg s.c. GA daily administration at reducing the subject population annualized relapse rate.

Secondary Outcome Measures

Treatment with 40 mg s.c. GA three times weekly significantly reduces the number of new $T_2$ lesions at month 12. Treatment with 40 mg s.c. GA three times weekly is at least as effective as 20 mg s.c. GA daily administration at reducing the number of new $T_2$ lesions at month 12.

Treatment with 40 mg s.c. GA three times weekly significantly reduces the cumulative number of enhancing lesions on $T_1$-weighted images taken at months 6 and 12. Treatment with 40 mg s.c. GA three times weekly is at least as effective as 20 mg s.c. GA daily administration at reducing the cumulative number of enhancing lesions on $T_1$-weighted images taken at months 6 and 12.

Treatment with 40 mg s.c. GA three times weekly significantly reduces brain atrophy as defined by the percent brain volume change from baseline to month 12. Treatment with 40 mg s.c. GA three times weekly is at least as effective as 20 mg s.c. GA daily administration at reducing brain atrophy as defined by the percent brain volume change from baseline to month 12.

Exploratory Endpoints

Treatment with 40 mg s.c. GA three times weekly significantly increases the time to the first confirmed relapse during the placebo-controlled phase. Treatment with 40 mg s.c. GA three times weekly is at least as effective as 20 mg s.c. GA daily administration at increasing the time to the first confirmed relapse during the placebo-controlled phase.

Treatment with 40 mg s.c. GA three times weekly significantly increases the proportion of relapse-free subjects during the placebo-controlled phase. Treatment with 40 mg s.c. GA three times weekly is at least as effective as 20 mg s.c. GA daily administration at increasing the proportion of relapse-free subjects during the placebo-controlled phase.

Treatment with 40 mg s.c. GA three times weekly significantly increases the proportion of relapse-free subjects during the placebo-controlled phase. Treatment with 40 mg s.c. GA three times weekly is at least as effective as 20 mg s.c. GA daily administration at increasing the proportion of relapse-free subjects during the placebo-controlled phase.

Treatment with 40 mg s.c. GA three times weekly significantly reduces the total number of confirmed relapses during the placebo-controlled phase requiring hospitalization and/or IV steroids. Treatment with 40 mg s.c. GA three times weekly is at least as effective as 20 mg s.c. GA daily administration at reducing the total number of confirmed relapses during the placebo-controlled phase requiring hospitalization and/or IV steroids.

Treatment with 40 mg s.c. GA three times weekly significantly reduces the progression of MRI-monitored disease activity in the patient. Treatment with 40 mg s.c. GA three times weekly is at least as effective as 20 mg s.c. GA daily administration at reducing the progression of MRI-monitored disease activity in the patient.

Treatment with 40 mg s.c. GA three times weekly significantly reduces the total volume of $T_2$ lesions at month 12. Treatment with 40 mg s.c. GA three times weekly is at least as effective as 20 mg s.c. GA daily administration at reducing total volume of $T_2$ lesions at month 12.

Treatment with 40 mg s.c. GA three times weekly significantly reduces the number of new hypointense lesions on enhanced $T_1$ scans at month 12 as compared to the baseline scan. Treatment with 40 mg s.c. GA three times weekly is at least as effective as 20 mg s.c. GA daily administration at reducing the number of new hypointense lesions on enhanced $T_1$ scans at month 12 as compared to the baseline scan.

Treatment with 40 mg s.c. GA three times weekly significantly reduces the total volume of hypointense lesions on enhanced $T_1$ scans at month 12. Treatment with 40 mg s.c. GA three times weekly is at least as effective as 20 mg s.c. GA daily administration at reducing the total volume of hypointense lesions on enhanced $T_1$ scans at month 12.

Treatment with 40 mg s.c. GA three times weekly significantly reduces brain atrophy as defined by the percentage change from baseline to month 12 in normalized gray matter volume and in normalized white matter volume. Treatment with 40 mg s.c. GA three times weekly is at least as effective as 20 mg s.c. GA daily administration at reducing brain atrophy as defined by the percentage change from baseline to month 12 in normalized gray matter volume and in normalized white matter volume.

Treatment with 40 mg s.c. GA three times weekly significantly reduces the level of disability as measured by EDSS Score. Treatment with 40 mg s.c. GA three times weekly is at least as effective as 20 mg s.c. GA daily administration at reducing the level of disability as measured by EDSS Score.

Treatment with 40 mg s.c. GA three times weekly significantly reduces the proportion (%) of subjects with confirmed EDSS progression during the placebo-controlled phase (progression of at least 1 EDSS point sustained for at least 3 months). Treatment with 40 mg s.c. GA three times weekly is at least as effective as 20 mg s.c. GA daily administration at reducing proportion (%) of subjects with confirmed EDSS progression during the placebo-controlled phase, (progression of at least 1 EDSS point sustained for at least 3 months).

Treatment with 40 mg s.c. GA three times weekly significantly reduces the change from baseline to month (end of placebo-controlled phase) in EDSS Score. Treatment with 40 mg s.c. GA three times weekly is at least as effective as 20 mg s.c. GA daily administration at reducing the change from baseline to month 12 (end of placebo-controlled phase) in EDSS Score.

Treatment with 40 mg s.c. GA three times weekly significantly reduces the change from baseline to month 12 (end of placebo-controlled phase) in Ambulation Index. Treatment with 40 mg s.c. GA three times weekly is at least as effective as 20 mg s.c. GA daily administration at reducing the change from baseline to month 12 (end of placebo-controlled phase) in Ambulation Index.

Treatment with 40 mg s.c. GA three times weekly significantly reduces the level of disability as measured by EuroQoL (EQ5D) questionnaire. Treatment with 40 mg s.c. GA three times weekly is at least as effective as 20 mg s.c. GA daily administration at reducing the level of disability as measured by EuroQoL (EQ5D) questionnaire.

Treatment with 40 mg s.c. GA three times weekly significantly reduces the level of disability as measured by the work productivity and activities impairment—General Health (WPAI-GH) questionnaire. Treatment with 40 mg s.c. GA three times weekly is at least as effective as 20 mg s.c. GA daily administration at reducing the level of disability as measured by the work productivity and activities impairment—General Health (WPAI-GH) questionnaire.

Discussion

A significant drawback to GA therapy is the requirement of daily injections, which can be inconvenient. Moreover, in all clinical trials, injection-site reactions were seen to be the most frequent adverse reactions and were reported by the majority of patients receiving GA. In controlled studies, the proportion of patients reporting these reactions, at least once, was higher following treatment with GA (70%) than placebo injections (37%). The most commonly reported injection-site reactions, which were more frequently reported in GA vs. placebo-treated patients, were erythema, pain, mass, puritus, edema, inflammation and hypersensitivity.

However, several obstacles and limitations with potential approaches for addressing the drawbacks exist to current GA therapy. Subcutaneous drug delivery is limited, firstly, by the acceptable injection volume. Typically no more than 1 to 2 ml of solution is permitted (Kansara V, Mitre A, Wu Y, Subcutaneous Delivery. Drug Deliv Technol, June 2009; 9(6):38-42). Secondly, the potential exists for drug degradation at the site of injection resulting in reduced bioavailability. Thirdly, based on the physiochemical properties of the drug, potent compounds may become locally trapped in the interstitial space which can lead to further localized irritation, precipitation of the drug and concentration-dependent adverse effects (Kansara V, Mitra A, Wu Y, Subcutaneous Delivery. Drug Deliv Technol, June 2009; 9(6):38-42). Finally, due to the complex pharmacokinetic behavior of a drug, variation in the frequency of administration is unpredictable and requires empirical testing. For example, although controlled clinical trials have demonstrated the efficacy of IFNβ-1b in the treatment of MS, patient compliance, efficacy and tolerability are affected by the dosage regimen used. Merely increasing the dose of IFNβ-1b is insufficient to increase efficacy, the frequency of administration must also be increased (Luca Durelli, J Neurol (2003) 250 [Suppl 4]).

Accordingly, the subject application discloses an effective low frequency dosage regimen of GA administration to patients suffering from a relapsing form of multiple sclerosis, including patients who have experienced a first clinical episode and have MRI features consistent with multiple sclerosis. Based on the performance of the dosage regimen in these studies, the administration of three s.c. injections over a period of seven days with at least one day between every injection is also expected to work in the treatment of patients who have experienced a clinically isolated syndrome (CIS). This is based on the fact that the 20 mg daily s.c. injection has been shown to work in PCT International Application No. PCT/US2008/013146 (see International Publication No. WO 2009/070298 and also U.S. Patent Application Publication No. US 2009-0149541 A1).

What is claimed is:

1. A method of treatment of a human patient suffering from a relapsing form of multiple sclerosis which consists of a regimen of administering weekly to the human patient on only three days during each week a single subcutaneous injection of a 40 mg dose of glatiramer acetate so as to treat the human patient, wherein the glatiramer acetate is present in 1 ml of a pharmaceutical composition in a prefilled syringe for self administration by the human patient, and the pharmaceutical composition further comprises mannitol and has a pH in the range of 5.5 to 7.0.

2. The method of claim 1, wherein the three days during each week are selected from the group consisting of day 1, day 3 and day 5; day 1, day 3 and day 6; day 1, day 4 and day 6; day 2, day 4 and day 6; day 2, day 4 and day 7; day 2, day 5 and day 7; and day 3, day 5 and day 7.

3. The method of claim 1, wherein the treatment results in reducing the frequency of relapses in the human patient by 30% or more as compared to placebo in a human population.

4. The method of claim 3, wherein the treatment further results in i) reducing the cumulative number of enhancing lesions on T1-weighted images of the human patient, and ii) reducing brain atrophy of the human patient.

5. The method of claim 1, wherein the human patient has not received glatiramer acetate therapy prior to initiation of the treatment.

6. The method of claim 5, wherein the three days during each week are selected from the group consisting of day 1, day 3 and day 5; day 1, day 3 and day 6; day 1, day 4 and day 6; day 2, day 4 and day 6; day 2, day 4 and day 7; day 2, day 5 and day 7; and day 3, day 5 and day 7.

7. The method of claim 5, wherein the treatment results in reducing the frequency of relapses in the human patient by 30% or more as compared to placebo in a human population.

8. The method of claim 7, wherein the treatment further results in i) reducing the cumulative number of enhancing lesions on T1-weighted images of the human patient, and ii) reducing brain atrophy of the human patient.

9. A method of treatment of a human patient suffering from a relapsing form of multiple sclerosis consisting of subcutaneous injections for at least 6 months of 1 ml of a pharmaceutical composition comprising 40 mg/ml of glatiramer acetate on only three days during each week with at least one day without a subcutaneous injection of the pharmaceutical composition between each day on which there is a subcutaneous injection, wherein the pharmaceutical composition is in a prefilled syringe, and wherein the pharmaceutical composition further comprises mannitol and has a pH in the range 5.5 to 7.0.

10. The method of claim 9, wherein during each week the subcutaneous injections are on day 1, day 3 and day 5 of such week; day 1, day 3 and day 6 of such week; day 1, day 4 and day 6 of such week; day 2, day 4 and day 6 of such week; day 2, day 4 and day 7 of such week; day 2, day 5 and day 7 of such week; or day 3, day 5 and day 7 of such week.

11. The method of claim 9, wherein the treatment results in reducing the frequency of relapses in the human patient by 30% or more as compared to placebo in a human population.

12. The method of claim 11, wherein the treatment further results in i) reducing the cumulative number of enhancing lesions on T1-weighted images of the human patient, and ii) reducing brain atrophy of the human patient.

13. The method of claim 9, wherein the human patient has not received glatiramer acetate therapy prior to initiation of the treatment.

14. The method of claim 13, wherein the treatment results in reducing the frequency of relapses in the human patient by 30% or more as compared to placebo in a human population.

15. The method of claim 14, wherein the treatment further results in i) reducing the cumulative number of enhancing lesions on T1-weighted images of the human patient, and ii) reducing brain atrophy of the human patient.

16. A method of treatment of a human patient suffering from a relapsing form of multiple sclerosis which method is more tolerable than and as effective as administration of 20 mg of glatiramer acetate s.c. daily, the method consisting of subcutaneous injections for at least 6 months of 1 ml of a pharmaceutical composition comprising 40 mg/ml of glatiramer acetate on only three days during each week with at least one day without a subcutaneous injection of the pharmaceutical composition between each day on which there is a subcutaneous injection, wherein the pharmaceutical composition is in a prefilled syringe, and wherein the pharmaceutical composition further comprises mannitol and has a pH in the range 5.5 to 7.0, so as to treat the human patient as effectively as, but more tolerably than, administration of 20 mg of glatiramer acetate s.c. daily, wherein the effect is reduction of relapses.

17. The method of claim 4, wherein the treatment further results in reducing a change in EDSS Score of the human patient.

18. The method of claim 8, wherein the treatment further results in reducing a change in EDSS Score of the human patient.

19. The method of claim 12, wherein the treatment further results in reducing a change in EDSS Score of the human patient.

20. The method of claim 15, wherein the treatment further results in reducing a change in EDSS Score of the human patient.

21. The method of claim 1, wherein the treatment results in reduced severity of injection site reactions relative to administration of 20 mg of glatiramer acetate s.c. daily.

22. The method of claim 9, wherein the treatment results in reduced severity of injection site reactions relative to administration of 20 mg of glatiramer acetate s.c. daily.

23. The method of claim 11, wherein the treatment results in reduced severity of injection site reactions relative to administration of 20 mg of glatiramer acetate s.c. daily.

24. The method of claim 1, wherein the treatment results in reduced frequency and severity of both immediate post injection reactions and injection site reactions, relative to administration of 20 mg of glatiramer acetate s.c. daily.

25. The method of claim 9, wherein the treatment results in reduced frequency and severity of both immediate post injection reactions and injection site reactions, relative to administration of 20 mg of glatiramer acetate s.c. daily.

26. The method of claim 11, wherein the treatment results in reduced frequency and severity of both immediate post injection reactions and injection site reactions, relative to administration of 20 mg of glatiramer acetate s.c. daily.

27. The method of claim 12, wherein the treatment results in reduced frequency and severity of both immediate post injection reactions and injection site reactions, relative to administration of 20 mg of glatiramer acetate s.c. daily.

28. The method of claim 13, wherein the treatment results in reduced frequency and severity of both immediate post injection reactions and injection site reactions, relative to administration of 20 mg of glatiramer acetate s.c. daily.

* * * * *